US006929896B2

(12) United States Patent
Yamato et al.

(10) Patent No.: US 6,929,896 B2
(45) Date of Patent: Aug. 16, 2005

(54) ONIUM SALTS AND THE USE THEROF AS LATENT ACIDS

(75) Inventors: Hitoshi Yamato, Takarazuka (JP); Toshikag Asakura, Minoo (JP); Akira Matsumoto, Amagasaki (JP); Masaki Ohwa, Kobe (JP)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 49 days.

(21) Appl. No.: 10/432,263

(22) PCT Filed: Nov. 26, 2001

(86) PCT No.: PCT/EP01/13725

§ 371 (c)(1),
(2), (4) Date: May 21, 2003

(87) PCT Pub. No.: WO02/46507

PCT Pub. Date: Jun. 13, 2002

(65) Prior Publication Data

US 2004/0053158 A1 Mar. 18, 2004

(30) Foreign Application Priority Data

Dec. 4, 2000 (EP) .............................................. 00811147
Jun. 8, 2001 (EP) .............................................. 01810551

(51) Int. Cl.⁷ .............................. G03F 7/004; G03F 7/30
(52) U.S. Cl. .................... 430/270.1; 430/296; 430/302; 430/311; 430/330; 430/910; 430/914; 430/917; 430/921; 430/922
(58) Field of Search .............................. 430/7, 10, 296, 430/270.1, 302, 311, 330, 322, 910, 914, 921, 922, 917

(56) References Cited

U.S. PATENT DOCUMENTS

| 4,965,379 | A | 10/1990 | Ikeda et al. .................. 549/521 |
| 5,314,747 | A | 5/1994 | Malhotra et al. ............ 428/341 |
| 6,620,957 | B1 * | 9/2003 | Tomita et al. ................. 558/20 |

FOREIGN PATENT DOCUMENTS

| EP | 0102450 | 3/1984 |
| EP | 0249139 | 12/1987 |
| EP | 0331988 | 9/1989 |
| EP | 0542523 | 5/1993 |
| EP | 0697632 | 2/1996 |
| EP | 0945475 | 9/1999 |
| EP | 967522 A1 * | 12/1999 ........... G03F/7/004 |
| EP | 1111465 A1 * | 6/2001 ........... G03F/7/038 |
| EP | 1164127 | 12/2001 |
| GB | 1235591 | 6/1971 |
| WO | 01/40167 | 6/2001 |

OTHER PUBLICATIONS

J. V. Crivello, Advances in Polymer Science 62, (1984), pp. 1–48.
H. Ito et al., Polymer Engineering and Science, Dec. 1983, vol. 23, No. 18. pp. 1012–1018.
Derwent Abstr. 90–071933/10 for JP 2025850 (1990).
Derwent Abstr. 90–221337/29 for JP 2150848 (1990).
Derwent Abstr. 94–269405/33 for JP 06199770 (1994).
Derwent Abstr. 93–323224/41 for JP 05232705 (1993).
Derwent Abstr. 94–095255/12 for JP 06043653 (1994).
Derwent Abstr. 96–323579/33 for JP 06123972 (1994).
Derwent Abstr. 96–136256/14 for JP 08027094 (1996).
E. Pongratz et al., Monatshefte für Chemie, vol. 115, pp. 231–242 (1984).
V. A. Budylin et al., Chemistry of Heterocyclic Compounds, vol. 17, No. 11, (1981), pp. 1095–1097.

* cited by examiner

*Primary Examiner*—Amanda C Walke
(74) *Attorney, Agent, or Firm*—Shiela A. Loggins

(57) ABSTRACT

A chemically amplified photoresist composition comprising, (a) a compound which cures upon the action of an acid or a compound whose solubility is increased upon the action of an acid; and (b) as photosensitive acid donor, at least one compound of the formula Ia, Ib, Ic, IIb or IIc wherein $R_1$ is for example $C_1$–$C_5$alkyl, $C_3$–$C_{30}$cycloalkyl, $C_1$–$C_5$haloalkyl, $C_2$–$C_{12}$alkenyl, $C_4$–$C_8$cycloalkenyl, $C_6$–$C_{12}$bicycloalkenyl, phenyl, naphthyl, anthracyl, phenanthryl, or is a heteroaryl radical; all of which are unsubstituted or substituted; optionally some of the substituents form 5- or 6-membered rings with further substituents on the phenyl, naphthyl, anthracyl, phenanthryl, or heteroaryl ring or with one of the carbon atoms of the phenyl, naphtyl, anthracyl, phenanthryl, or heteroaryl ring; $R'_1$ is for example $C_1$–$C_{12}$alkylene, $C_3$–$C_{30}$cycloalkylene, phenylene, naphtylene, diphenylene, or oxydiphenylene, wherein these radicals are unsubstituted or substituted; A and B for example are a direct bond; $Ar_1$ and $Ar_2$ independently of each other for example are phenyl, naphtyl, anthracyl, phenanthryl, or heteroaryl, all of which are unsubstituted or are substituted; $Ar_3$, $Ar_4$ and $Ar_5$ for example have one of the meanings given for $Ar_1$ and $Ar_2$; Y is for example $C_3$–$C_3$–$C_{30}$cycloalkylene, phenylene, naphthylene, diphenylene, or oxydiphenylene, all of which are unsubstituted or substituted.

13 Claims, No Drawings

ONIUM SALTS AND THE USE THEROF AS LATENT ACIDS

The invention relates to new onium salts, chemically amplified photoresist compositions comprising said compounds and to the use of the compounds as latent acids, which can be activated by irradiation with actinic electromagnetic radiation and electron beams.

Diaryliodonium salts and triarylsulfonium salts having non-nucleophilic counter anions such as $BF_4^-$, $PF_6^-$, $AsF_6^-$ and $SbF_6^-$ are well known as suitable photoinitiators for cationic polymerization as described, for example, by J. V. Crivello in Advances in Polymer Science 62, 1–48, (1984). The use of such onium salts for chemically amplified photoresists is described in EP 102450 and Polym. Eng. Sci., 23, 1012 (1983). In EP 249139, Derwent 90-071933/10 (JP-A-2-25850), Derwent 90-221337/29 (JP-A-2-150848), EP 542523 and Derwent 93-323224/41 (JP-A-5-232705) iodonium and sulfonium salts having trifluoromethanesulfonate as the counter anion are described. In Derwent No. 90-071933/10 (JP-A-2-25850), Derwent 90-221337/29 (JP-A-2-150848), Derwent 94-095255/12 (JP-A-6-43653) and Derwent 96-323579/33 (JP-A-6-123972) iodonium and sulfonium salts having toluenesulfonate as the counter anion are disclosed. In Derwent 94-269405/33 (JP-A-6-199770) and Derwent 96-136256/14 (JP-A-8-27094) iodonium and sulfonium salts having dodecylbenzenesulfonate, dodecylsulfate and perfluorooctylsulfonate anions are described.

In the art exists a need for reactive latent acid donors that are thermally and chemically stable and that, after being activated by light, UV-radiation, X-ray irradiation or electron beams, can be used as catalysts for a variety of acid-catalysed reactions, such as polycondensation reactions, acid-catalysed depolymerisation reactions, acid-catalysed electrophilic substitution reactions or the acid-catalysed removal of protecting groups. A particular need exists for latent acid catalysts, producing strong acids, having high stability and good solubility in the field of chemically amplified photoresists.

Surprisingly, it has now been found that specific onium salts, as described below, are well soluble in ordinary resist solvents and especially suitable as catalysts for the aforementioned acid catalyzed reactions. Furthermore, chemically amplified photoresist compositions comprising onium salts of the present invention are thermally stable-even at high bake temp ratures during processing- and provide high photospeed.

The invention accordingly relates to a chemically amplified photoresist composition comprising, (a) a compound which cures upon the action of an acid or a compound whose solubility is in-creased upon the action of an acid; and
(b) as photosensitive acid donor, at least one compound of the formula Ia, Ib, Ic, IIa, IIb or IIc

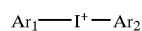
(Ia)

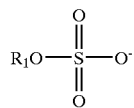

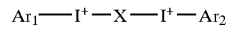
(Ib)

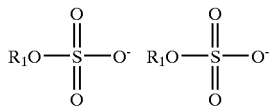

(Ic)

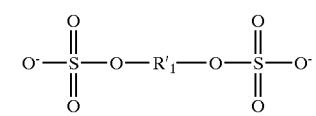

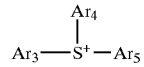
(IIa)

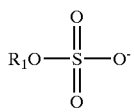

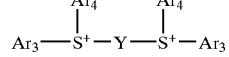
(IIb)

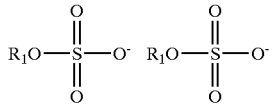

(IIc)

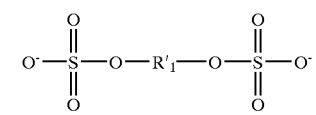

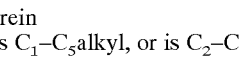

wherein $R_1$ is $C_1$–$C_5$alkyl, or is $C_2$–$C_{12}$alkyl which is interrupted by one or more —O— or —(CO)—, or is $C_3$–$C_{30}$cycloalkyl, or is $C_3$–$C_{30}$cycloalkyl which is interrupted by one or more —O—, —S—, —$NR_6$—, —(CO)—, —O(CO)— or —$NR_8$(CO)—, or is $C_1$–$C_5$haloalkyl, or is $C_2$–$C_{12}$alkenyl, or is $C_4$–$C_8$cycloalkenyl, or is $C_8$–$C_{12}$bicycloalkenyl, all of which are unsubstituted or substituted by one or more $C_1$–$C_5$alkyl, $C_1$–$C_5$haloalkyl; $C_3$–$C_{30}$cycloalkyl which optionally is interrupted by one or more —O—, —S—, —$NR_6$—, —(CO)—, —O(CO)— or —$NR_6$(CO)—; or are substituted by halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_8$(CO)$OR_3$, —$OR_3$, —$NR_4R_5$, —$SR_6$, —$SOR_2$, —$SO_2R_2$ and/or —$OSO_2R_2$;

or $R_1$ is phenyl, or is naphthyl, or is anthracyl or is phenanthryl, or is a heteroaryl radical, all of which are unsubstituted or substituted by one or more $C_1$–$C_5$alkyl; $C_2$–$C_{12}$alkyl which is interrupted by one or more —O—; or are substituted by $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$ (CO)$OR_3$, —$OR_3$, —$NR_4R_5$, —$SR_8$, —$SOR_2$, —$SO_2R_2$ and/or —$OSO_2R_2$; optionally the substituents —(CO)$R_2$, —(CO)$OR_3$, —(CO)$NR_4R_5$, —O(CO)$R_2$, —O(CO)$OR_3$, —O(CO)NR$_4$R$_5$, —NR$_6$(CO)R$_2$, —NR$_6$(CO)OR$_3$, —OR$_3$, —NR$_4$R$_5$, —SR$_8$, —SOR$_2$, —SO$_2$R$_2$ and/or —OSO$_2$R$_2$ form 5- or 6-membered rings, via the radicals R$_2$, R$_3$, R$_4$ R$_5$ and/or R$_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

wherein all radicals R$_1$ optionally additionally are substituted by a group having a —O—C-bond or a —O—Si-bond which cleaves upon the action of an acid;

R'$_1$ is C$_1$–C$_{12}$alkylene; or is C$_2$–C$_{12}$alkylene which is interrupted by one or more C$_3$–C$_{30}$ cycloalkylene, —O—, —S—, —NR$_8$—, —(CO)—, —O(CO)—, —S(CO)—, —NR$_6$(CO)—, —SO—, —SO$_2$—, or —OSO$_2$—; optionally the radicals C$_1$–C$_{12}$alkylene and C$_2$–C$_{12}$alkylene are substituted by one or more C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R'$_1$ is C$_3$–C$_{30}$cycloalkylene, optionally interrupted by one or more —O—, —S—, —NR$_6$—, —(CO)—, —O(CO)—, or —NR$_6$(CO)—, and which is unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_8$, —SOR$_2$, —SO$_2$R$_2$ and/or —OSO$_2$R$_2$;

or R'$_1$ is phenylene, naphthylene,

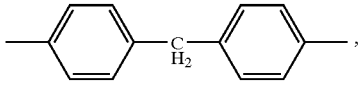

diphenylene, oxydiphenylene or

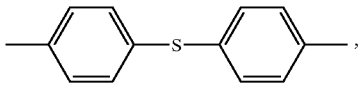

wherein these radicals are unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R'$_1$ is

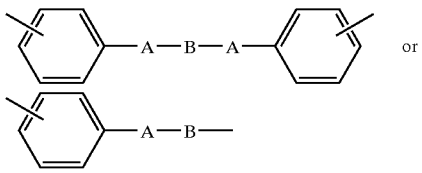 or

A is a direct bond, —O—, —S—, —NR$_6$—, —O(CO)—, —S(CO)—, —NR$_6$(CO)—, —SO—, —SO$_2$— or —OSO$_2$—;

B is a direct bond, C$_1$–C$_{12}$alkylene or C$_2$–C$_{12}$alkylene which is interrupted by one or more —O—, —S—, —NR$_6$—, —O(CO)—, —S(CO)—, —NR$_6$(CO)—, —SO—, —SO$_2$— or —OSO$_2$—, and optionally the radicals C$_1$–C$_{12}$alkylene and C$_2$–C$_{12}$alkylene are substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

R$_2$ is phenyl, or is C$_3$–C$_{30}$cycloalkyl, or is C$_1$–C$_5$alkyl; or is C$_2$–C$_5$alkyl which is interrupted by one or more —O—, or is C$_3$–C$_{30}$cycloalkyl which is interrupted by one or more —O—, —S—, —NR$_6$—, —O(CO)—, or —NR$_6$(CO)—;

all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, —NR$_4$R$_5$, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and/or by C$_1$–C$_4$alkanoyl;

or R$_2$ is hydrogen;

R$_3$ is phenyl, or is C$_3$–C$_{30}$cycloalkyl, or is C$_1$–C$_5$alkyl; or is C$_2$–C$_5$alkyl which is interrupted by one or more —O—; or is C$_3$–C$_{30}$cycloalkyl which is interrupted by one or more —O—, —S—, —NR$_6$—, —O(CO)—, or —NR$_6$(CO)—; or is C$_2$–C$_{18}$alkanoyl, or is benzoyl, or is C$_1$–C$_1$alkylsulfonyl, all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, —NR$_4$R$_5$, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and/or by C$_1$–C$_4$alkanoyl;

or R$_3$ is hydrogen, phenylsulfonyl, (4-methylphenyl)sulfonyl, naphthylsulfonyl, anthracyl-sulfonyl or phenanthrylsulfonyl;

R$_4$, R$_5$ and R$_6$ independently of each other are phenyl, or are C$_3$–C$_{30}$cycloalkyl, or are C$_1$–C$_5$alkyl; or are C$_2$–C$_5$alkyl which is interrupted by one or more —O—; or are C$_3$–C$_{30}$cycloalkyl which is interrupted by one or more —O—, —S—, —NR$_6$—, —O(CO)—, or —NR$_6$(CO)—; or are C$_2$–C$_{18}$alkanoyl, or are benzoyl, or are C$_1$–C$_{18}$alkylsulfonyl, all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and for by C$_1$–C$_4$alkanoyl;

or R$_4$, R$_5$ and R$_6$ independently of each other are hydrogen, phenylsulfonyl, (4-methyl-phenyl)sulfonyl, naphthylsulfonyl, anthracylsulfonyl or phenanthryisulfonyl;

or R$_4$ and R$_5$, together with the nitrogen atom to which they are attached, form a 5-, 6- or 7-membered ring which optionally is interrupted by —O— or by —NR$_6$—;

Ar$_1$ and Ar$_2$ independently of each other are phenyl, or are naphthyl, or are anthracyl, or are phenanthryl, or are heteroaryl, all of which are unsubstituted or are substituted by one or more C$_1$–C$_{12}$alkyl, C$_1$–C$_5$haloalkyl, C$_3$–C$_{30}$cycloalkyl;

$C_3$–$C_{30}$cycloalkyl which is interrupted by one or more —O—, —S—, —$NR_6$—, —O(CO)—, or —$NR_6$(CO)—; or are substituted by halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$, optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

or $Ar_1$ and $Ar_2$, if appropriate together with $C_1$–$C_2$alkylene, —O—, —S—, —$NR_6$—, or —(CO)—, form a fused ring; wherein all radicals $Ar_1$ and $Ar_2$ optionally additionally are substituted by a group having a —O—C-bond or a —O—Si-bond which cleaves upon the action of an acid;

$Ar_3$, $Ar_4$ and $Ar_5$ have one of the meanings given for $Ar_1$ and $Ar_2$ or are or $Ar_3$, $Ar_4$ and $Ar_5$ independently of each other are $C_1$–$C_{12}$alkyl; or are $C_2$–$C_{12}$alkyl which is interrupted by one or more —O—; or are $C_1$–$C_5$haloalkyl; or are $C_3$–$C_{30}$cycloalkyl which optionally is interrupted by one or more —O—, —S—, —$NR_6$—, —O(CO)—, -or —$NR_6$(CO)—;

all of which are unsubstituted or substituted by one or more $C_1$–$C_{12}$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or $Ar_3$ and $Ar_4$, if appropriate together with $C_1$–$C_2$alkylene, —O—, —S—, —$NR_6$—, —(CO)—, form a fused ring;

or $Ar_3$ and $Ar_4$, if appropriate together with $C_1$–$C_2$alkylene, —O—, —S—, —$NR_6$—, —(CO)—, form a 5-, 6-, or 7-membered ring;

wherein all radicals $Ar_3$, $Ar_4$ and $Ar_5$ optionally additionally are substituted by a group having a —O—C-bond or a —O—Si-bond which cleav s upon the action of an acid;

$Ar_6$ is phenyl, or is naphthyl, or is anthracyl, or is phenanthryl or is heteroaryl, all of which are unsubstituted or substituted by one or more $C_1$–$C_5$ alkyl; $C_2$–$C_{12}$alkyl which is interrupted by one or more —O—; or by $C_1$–$C_5$haloalkyl, $C_3$–$C_{30}$cycloalkyl, halogen, —$NO_2$, —CN, phenyl, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$, optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl, naphthyl, anthracyl, phenanthryl or heteroaryl ring or with one of the carbon atoms of the phenyl, naphthyl, anthracyl, phenanthryl or heteroaryl ring;

X is phenylene, or is naphthylene, or is

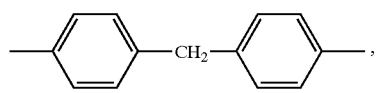

or is diphenylene, or is oxydiphenylene or is

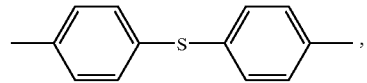

all of which are unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or X is ![benzene]—A—B—A—![benzene]— ; and

Y has one of the meanings given for X, or is $C_1$–$C_{12}$alkylene; or $C_2$–$C_{12}$alkylene which is interrupted by one or more $C_3$–$C_{30}$cycloalkylene, —O—, —S—, —$NR_6$—, —(CO)—, —O(CO)—, —S(CO)—, —$NR_6$(CO)—, —SO—, —$SO_2$—, or —$OSO_2$—; wherein the $C_1$–$C_{12}$alkylene and $C_2$–$C_{12}$alkylene are unsubstituted or substituted by one or more $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or Y is $C_3$–$C_{30}$cycloalkylene which optionally is interrupted by one or more —O—, —S—, —$NR_6$—, —(CO)—, —O(CO)—, or —$NR_6$(CO)—, and which is unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$.

$C_1$–$C_{12}$Alkyl is linear or branched and is, for example, $C_1$–$C_5$- or $C_1$–$C_5$-alkyl. Examples are methyl, ethyl, propyl, isopropyl, n-butyl, sec-butyl, isobutyl, tert-butyl, pentyl, hexyl, heptyl, 2,4,4-trimethylpentyl, 2-ethylhexyl, octyl, nonyl, decyl, undecyl and dodecyl, preferably $C_1$–$C_5$-alkyl, such as methyl, isopropyl or butyl.

$C_2$–$C_{12}$Alkyl, which is interrupted once or several times by —O—, is interrupted, for example, from one to five times, for example from one to three times or once or twice, by non-successive —O—. Accordingly, resulting structural units are for example: —O(CH$_2$)$_2$OH, —O(CH$_{22}$OCH$_3$, —O(CH$_2$CH$_2$O)$_2$CH$_2$CH$_3$, —CH$_2$—O—CH$_3$, —CH$_2$CH$_2$—O—CH$_2$CH$_3$, —[CH$_2$CH$_2$O]$_y$—CH$_3$, wherein y=1–5, —(CH$_2$CH$_2$O)$_5$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$.

$C_3$–$C_{30}$Cycloalkyl is a mono- or polycyclic aliphatic ring, for example a mono-, bi- or tricyclic aliphatic ring, e.g. $C_3$–$C_{20}$-, $C_3$–$C_{18}$-, $C_3$–$C_{12}$-, $C_3$–$C_{10}$cycloalkyl. Examples of monocyclic rings are cyclopropyl, cyclobutyl, cyclopentyl, cyclohexyl, or cycloheptyl, especially cyclopentyl and cyclohexyl. Examples of polycyclic rings are perhydroanthracyl, perhydrophenanthryl, perhydronaphthyl, perhydrofluorenyl, perhydrochrysenyl, perhydropicenyl, adamantyl, bicyclo-[1.1.1]pentyl, bicyclo[4.2.2]decyl, bicyclo[2.2.2]octyl, bicyclo[3.3.2]decyl, bicyclo[4.3.2] undecyl, bicyclo[4.3.3]dodecyl, bicyclo[3.3.3]undecyl, bicyclo[4.3.1decyl, bicyclo[4.2.1]nonyl, bicyclo[3.3.1]

nonyl, bicyclo[3.2.1]octyl and the like. Also "spiro"-cycloalkyl compounds are covered by the definition $C_3$–$C_{30}$cycloalkyl in the present context, e.g. spiro[5.2]octyl, spiro[5.4]decyl, spiro[5.5]undecyl. More examples of polycyclic cycloalkyl groups, which are subject of the respective definition in the compounds of the present invention are listed in EP 878738, pages 11 and 12, wherein to the formulae (1)–(46) a bond to achieve the "yl" has to be added. The person skilled in the art is aware of this fact.

In general, the cycloaliphatic rings may form repeating structural units.

$C_3$–$C_{30}$Cycloalkyl which is interrupted by one or more —O—, —S—, —NR$_6$—, —O(CO)—, —SCO—, —NR$_6$CO—, —SO—, —SO$_2$—, —OSO$_2$— is a mono- or polycyclic aliphatic ring which is interrupted by one or more —O—, —S—, —NR$_6$—, —O(CO)—, —SCO—, —NR$_6$CO—, —SO—, —SO$_2$—, —OSO$_2$—, for example,

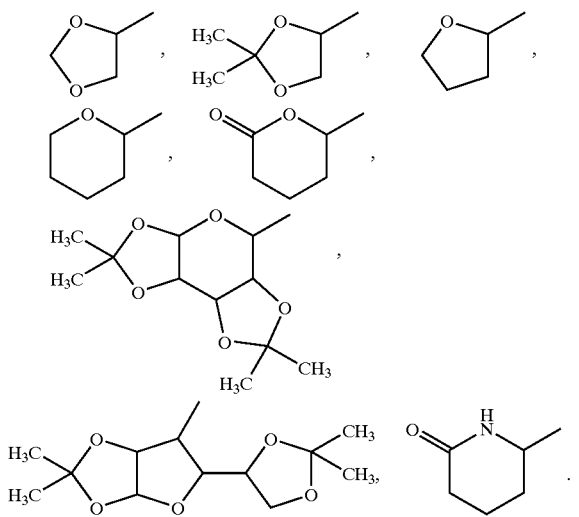

$C_2$–$C_{12}$Alkenyl radicals may be mono- or polyunsaturated, linear or branched and are for example $C_2$–$C_8$-, $C_2$–$C_6$- or $C_2$–$C_4$alkenyl. Examples are allyl, methallyl, vinyl, 1,1-dimethylallyl, 1-butenyl, 3-butenyl, 2-butenyl, 1,3-pentadienyl, 5-hexenyl or 7-octenyl, especially allyl or vinyl.

$C_4$–$C_8$Cycloalkenyl, may have one or more double bonds and is for example $C_4$–$C_6$-cycloalkenyl or $C_6$–$C_8$-cycloalkenyl. Examples are cyclobutenyl, cyclopentenyl, cyclohexenyl or cyclooctenyl, especially cyclopentenyl and cyclohexenyl, preferably cyclohexenyl.

$C_6$–$C_{12}$Bicycloalkenyl refers to a bicyclic alkenyl group, which may possess one or more double bonds and wherein the double bonds are either situated in the same ring, but may also be situated in both rings. If several double bonds are present in the bicyclus, the double bonds are conjugated or non-conjugated, preferably the double bonds are conjugated. Examples are bicyclo[4.2.4]dodec-3,7-dien-5-yl, bicyclo[4.2.4]dodec-3-en-5-yl, bicyclo[4.2.4]dodec-4-en-6-yl, bicyclo[4.2.31]non-3-en-5-yl, bicyclo[4.2.3]-non-4-en-6-yl, bicyclo[4.2.3]-non-7-en-8-yl, bicyclo[4.2.3]-non-8-en-7-yl, wherein the examples are referring to the following numbering

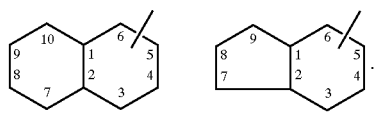

$C_2$–$C_{12}$Alkylene is linear or branched and is, for example, $C_2$–$C_8$-, $C_2$–$C_6$- or $C_2$–$C_4$-alkylene. Examples are ethylene, propylene, butylene, pentylene, hexylene, heptylene, octylene, nonylene, decylene, undecylene and dodecylene. Preferred is $C_1$–$C_8$alkylene, especially $C_1$–$C_6$alkylene, preferably $C_1$–$C_4$alkylene, such as methylene or butylene.

Substituted phenyl carries from one to five, for example one, two or three, especially one or two, substituents on the phenyl ring. The substitution is preferably in the 4-, 3,4-, 3,5- or 3,4,5-position of the phenyl ring.

When the radicals naphthyl, phenanthryl, heteroaryl and anthracyl are substituted by one or more radicals, they are, for example, mono- to penta-substituted, for example mono-, di- or tri-substituted, especially mono- or di-substituted.

When R$_1$ is a phenyl radical substituted by OR$_3$, NR$_4$R$_5$ and/or by SR$_6$ and the substituents OR$_3$, NR$_4$R$_5$ and/or SR$_6$ form 5- or 6-membered rings, via the radicals R$_3$, R$_4$, R$_5$ and/or R$_6$, with other substituents on the phenyl ring or with one of the carbon atoms of the phenyl ring, for, example the following structural units are obtained

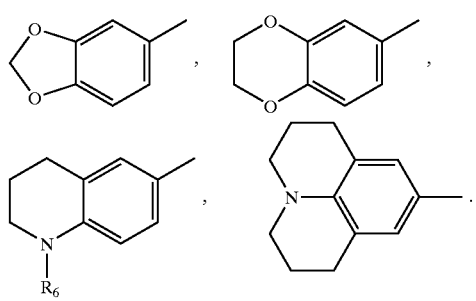

In the present application, the term "heteroaryl" denotes unsubstituted and substituted radicals, for example 3-thienyl, 2-thienyl,

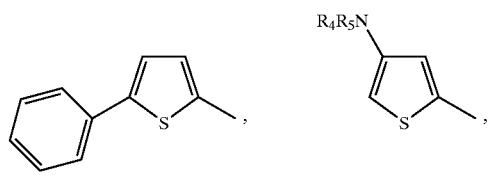

wherein R$_4$ and R$_5$ are as defined above, thianthrenyl, isobenzofuranyl, xanthenyl, phenoxanthiinyl,

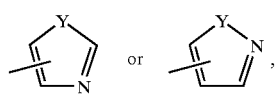

wherein Y is S, O or NR$_6$ and R$_6$ is as defined above. Examples thereof are pyrazolyl, thiazolyl, oxazolyl, isothiazolyl or isoxazolyl. Also included are, for example, furyl, pyrrolyl, 1,2,4-triazolyl,

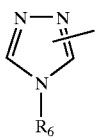

or 5-membered ring heterocycles having a fused-on aromatic group, for example benzimidazolyl, benzothienyl, benzofuranyl, benzoxazolyl and benzothiazolyl.

Other examples of "heteroaryls" are pyridyl, especially 3-pyridyl,

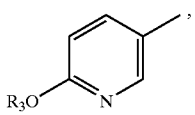

wherein $R_3$ is as defined above, pyrimidinyl, pyrazinyl, 1,3,5-triazinyl, 2,4-, 2,2- or 2,3-diazinyl, indolizinyl, isoindolyl, indolyl, indazolyl, purinyl, isoquinolyl, quinolyl, phenoxazinyl or phenazinyl. In this application, the term heteroaryin also denotes the radicals thioxanthyl, xanthyl,

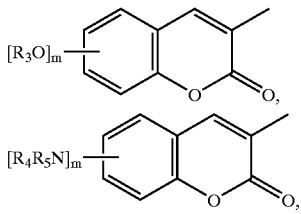

wherein m is 0 or 1 and $R_3$, $R_4$, $R_5$ are as defined above,

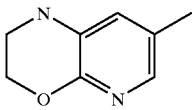

or anthraquinonyl. Each of the heteroaryls may carry the substituents indicated above or in claim 1.

$C_1$–$C_4$Alkanoyl is, for example, formyl, acetyl, propionyl or butanoyl, especially acetyl.

$C_1$–$C_4$Alkoxy is, for example, methoxy, ethoxy, propoxy and butoxy, it being possible for the alkyl radicals in alkoxy groups having more than two carbon atoms also to be branched.

$C_1$–$C_4$Alkylthio is for example, methylthio, ethylthio, propylthio and butylthio, it being possible for the alkyl radicals in alkylthio groups having more than two carbon atoms also to be branched.

$C_2$–$C_4$Alkoxycarbonyl is ($C_1$–$C_3$alkyl)-O—C(O)—, wherein $C_1$–$C_3$alkyl is as defined above up to the appropriate number of carbon atoms. Examples are methoxycarbonyl, ethoxycarbonyl or propoxycarbonyl, it being possible for the alkyl radicals in alkoxy groups having more than two carbon atoms also to be branched.

$C_1$–$C_4$Haloalkyl is $C_1$–$C_4$-alkyl mono- or polysubstituted by halogen, $C_1$–$C_4$-alkyl being, for example, as defined above. There are, for example, from one to three or one or two halogen substituents at the alkyl radical. Examples are chloromethyl, trichloromethyl, trifluoromethyl, 2-bromopropyl, especially trifluoromethyl or trichlorom thyl.

$C_2$–$C_4$Haloalkanoyl is ($C_1$–$C_3$haloalkyl)-C(O)—, wherein $C_1$–$C_3$haloalkyl is as defined above up to the appropriate number of carbon atoms. Examples are chloroacetyl, trichloroacetyl, trifluoroacetyl, pentafluoropropionyl or 2-bromopropionyl, especially trifluoroacetyl or trichloroacetyl.

Halobenzoyl is benzoyl which is mono- or polysubstituted by halogen and/or $C_1$–$C_5$haloalkyl, $C_1$–$C_4$-haloalkyl being as defined above. Examples are pentafluorobenzoyl, trichlorobenzoyl, trifluoromethylbenzoyl, especially pentafluorobenzoyl.

Halogen is fluorine, chlorine, bromine or iodine, especially chlorine or fluorine, preferably fluorine.

Oxydiphenylene is

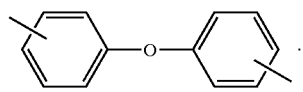

When $R_4$ and $R_5$ together with the nitrogen atom to which they are bonded form a 5-, 6- or 7-membered ring that may be interrupted by —O— or by —$NR_6$—, for example the following structures are obtained

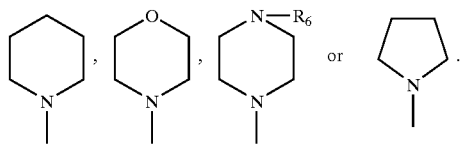

The definitions $C_1$–$C_4$allkylsulfonyl, phenylsulfonyl, (4-methylphenyl)sulfonyl refer to the corresponding radicals $C_1$–$C_4$alkyl, phenyl and 4-methylphenyl, as described in detail above, being linked to a sulfonyl group (—$SO_2$—).

The definitions $C_1$–$C_4$alkylsulfonyloxy, phenylsulfonyloxy, (4-methylphenyl)sulfonyloxy refer to the corresponding radicals $C_1$–$C_4$alkyl, phenyl and 4-methylphenyl (R), as described in detail above, being linked to a sulfonyloxy group

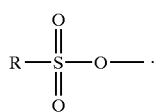

Groups having a —O—C-bond or a —O—Si-bond which cleaves upon the action of an acid, and being substituents of the radical $R_1$ are acid cleavable groups which increase the solubility of the compounds of formula Ia, IIa, Ib, IIb, Ic or IIc in the alkaline developer after reaction with an acid. This effect is for example described in U.S. Pat. No. 4,883,740.

Examples of groups suitable as substitutents on the radical $R_1$ are for example known orthoesters, trityl and benzyl groups, tert.-butyl esters of carboxylic acids, tert.-butyl carbonates of phenols or silyl ethers of phenols, e.g. —OSI$(CH_3)_3$,

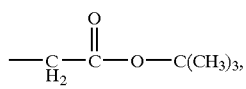     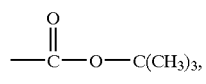

-continued

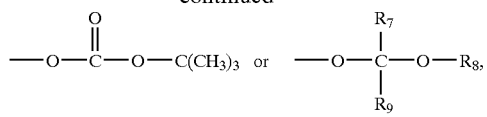 or 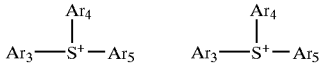

wherein $R_7$ and $R_8$ independently of one another are hydrogen, $C_1$–$C_5$alkyl, $C_3$–$C_8$-cycloalkyl, phenyl-$C_1$–$C_3$-alkyl, or $R_7$ and $R_8$ together are $C_2$–$C_5$alkylene, and $R_9$ is unsubstituted or halogen-substitued $C_1$–$C_5$alkyl, unsubstituted or halogen-substitued $C_3$–$C_8$cycloalkyl, or phenyl-$C_1$–$C_3$-alkyl, or, if $R_7$ and $R_8$ together are no $C_2$–$C_5$alkylene, $R_9$ and $R_8$ together may be $C_2$–$C_5$alkylene, which may be interrupted by an —O-atom or an —S-atom.

The terms "and/or" or "or/and" in the claims are meant to express that not only one of the defined alternatives (substituents) may be present, but also several of the defined alternatives (substituents) together, namely mixtures of different alternatives (substituents).

The term "at least" is meant to define one or more than one, for example one or two or three, preferably one or two.

The term "optionally" is used in the sense of "it is also possible that . . . ".

Most of the compounds of the formulae Ia, Ib, Ic, IIa, IIb and IIc are novel.

The invention therefore also pertains to novel compounds of formula Ia, Ib, Ic, IIa, IIb or IIc

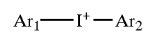 (Ia)

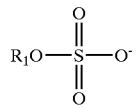

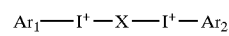 (Ib)

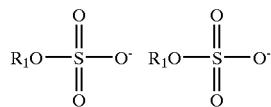

 (Ic)

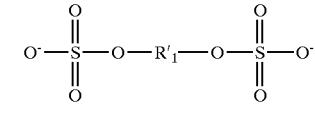

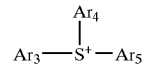 (IIa)

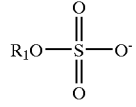

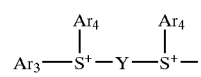 (IIb)

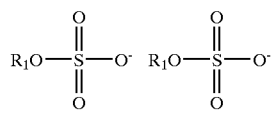

(IIc)

$Ar_3$—$S^+$—$Ar_5$ with $Ar_4$ above ; $Ar_3$—$S^+$—$Ar_5$ with $Ar_4$ above $O^-$—$S(=O)_2$—$O$—$R'_1$—$O$—$S(=O)_2$—$O^-$ wherein
$R_1$ is $C_1$–$C_5$alkyl, or is $C_2$–$C_{12}$alkyl which is interrupted by one or more —O— or —(CO)—, or is $C_3$–$C_{13}$cycloalkyl, or is $C_3$–$C_{30}$cycloalkyl which is interrupted by one or more —O—, —S—, —$NR_6$—, —(CO)—, —O(CO)— or —$NR_6$(CO)—, or is $C_1$–$C_5$haloalkyl, or is $C_2$–$C_{12}$alkenyl, or is $C_4$–$C_8$cycloalkenyl, or is $C_6$–$C_{12}$bicycloalkenyl,
all of which are unsubstituted or substituted by one or more $C_1$–$C_5$alkyl, $C_1$–$C_5$haloalkyl; $C_3$–$C_{30}$cycloalkyl which optionally is interrupted by one or more —O—, —S—, —$NR_6$—, —(CO)—, —O(CO)— or —$NR_6$(CO)—; or are substituted by halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;
or $R_1$ is phenyl, or is naphthyl, or is anthracyl or is phenanthryl, or is a heteroaryl radical, all of which are unsubstituted or substituted by one or more $C_1$–$C_5$alkyl; $C_2$–$C_{12}$alkyl which is interrupted by one or more —O—; or are substituted by $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;
optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;
wherein all radicals $R_1$ optionally additionally are substituted by a group having a —O—C-bond or a —O—Si-bond which cleaves upon the action of an acid;
$R'_1$ is $C_1$–$C_{12}$alkylene; or is $C_2$–$C_{12}$alkylene which is interrupted by one or more $C_3$–$C_{30}$cycloalkylene, —O—, —S—, —$NR_8$—, —(CO)—, —O(CO)—, —S(CO)—, —$NR_6$(CO)—, —SO—, —$SO_2$—, or —$OSO_2$—;
optionally the radicals $C_1$–$C_{12}$alkylene and $C_2$–$C_{12}$alkylene are substituted by one or more $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;
or $R'_1$ is $C_3$–$C_{30}$cycloalkylene, optionally interrupted by one or more —O—, —S—, —$NR_6$—, —(CO)—, —O(CO)—, or —$NR_6$(CO)—, and which is unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_1$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or R'₁ is phenylene, naphthylene,

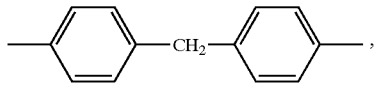

diphenylene, oxydiphenylene

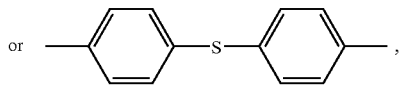

wherein these radicals are unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or R'₁ is

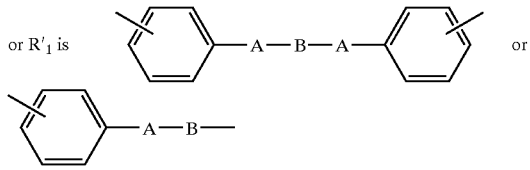

or

A is a direct bond, —O—, —S—, —$NR_6$—, —O(CO)—, —S(CO)—, —$NR_6$(CO)—, —SO—, —$SO_2$— or —$OSO_2$—;

B is a direct bond, $C_1$–$C_{12}$alkylene or $C_2$–$C_{12}$alkylene which is interrupted by one or more —O—, —S—, —$NR_6$—, —O(CO)—, —S(CO)—, —$NR_6$(CO)—, —SO—, —$SO_2$— or —$SO_2$—, and optionally the radicals $C_1$–$C_{12}$alkylene and $C_2$–$C_{12}$alkylene are substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_5$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

$R_2$ is phenyl, or is $C_3$–$C_{30}$cycloalkyl, or is $C_1$–$C_5$alkyl; or is $C_2$–$C_5$alkyl which is interrupted by one or more —O—, or is $C_3$–$C_{30}$cycloalkyl which is interrupted by one or more —O—, —S—, —$NR_8$—, —O(CO)—, or —$NR_6$(CO)—;

all of which are unsubstituted or substituted by phenyl, OH, $C_1$–$C_5$alkyl, $C_1$–$C_5$haloalkyl, $C_3$–$C_{30}$cycloalkyl, halogen, —$NO_2$, —CN, $C_1$–$C_4$alkoxy, phenoxy, phenoxycarbonyl, phenylthio, phenylthiocarbonyl, —$NR_4R_5$, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;
or $R_2$ is hydrogen;

$R_3$ is phenyl, or is $C_3$–$C_{30}$cycloalkyl, or is $C_1$–$C_5$alkyl; or is $C_2$–$C_5$alkyl which is interrupted by one or more —O—; or is $C_3$–$C_{30}$cycloalkyl which is interrupted by one or more —O—, —S—, —$NR_6$—, —O(CO)—, or —$NR_6$(CO)—; or is $C_2$–$C_{18}$alkanoyl, or is benzoyl, or is $C_1$–$C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, —$NO_2$, —CN, $C_1$–$C_4$alkoxy, phenoxy, phenoxycarbonyl, phenylthio, phenylthiocarbonyl, —$NR_4R_5$, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;
or $R_3$ is hydrogen, phenylsulfonyl, (4-methylphenyl)sulfonyl, naphthylsulfonyl, anthracylsulfonyl or phenanthrylsulfonyl;

$R_4$, $R_5$ and $R_6$ independently of each other are phenyl, or are $C_3$–$C_{30}$cycloalkyl, or are $C_1$–$C_5$alkyl; or are $C_2$–$C_5$alkyl which is interrupted by one or more —O—; or are $C_3$–$C_{30}$cycloalkyl which is interrupted by one or more —O—, —S—, —$NR_6$—, —O(CO)—, or —$NR_6$(CO)—;
or are $C_2$–$C_{18}$alkanoyl, or are benzoyl, or are $C_1$–$C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, —$NO_2$, —CN, $C_1$–$C_4$alkoxy, phenoxy, phenoxycarbonyl, phenylthio, phenylthiocarbonyl, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;
or $R_4$, $R_5$ and $R_6$ independently of each other are hydrogen, phenylsulfonyl, (4-methylphenyl)sulfonyl, naphthylsulfonyl, anthracylsulfonyl or phenanthrylsulfonyl;
or $R_4$ and $R_5$, together with the nitrogen atom to which they are attached, form a 5-, 6- or 7-membered ring which optionally is interrupted by —O— or by —$NR_6$—;

$Ar_1$ and $Ar_2$ independently of each other are phenyl, or are naphthyl, or are anthracyl, or are phenanthryl, or are heteroaryl, all of which are unsubstituted or are substituted by one or more $C_1$–$C_{12}$alkyl, $C_1$–$C_5$haloalkyl, $C_3$–$C_{30}$cycloalkyl; $C_3$–$C_{30}$cycloalkyl which is interrupted by one or more —O—, —S—, —$NR_6$—, —O(CO)—, or —$NR_6$(CO)—; or are substituted by halogen, —$NO_2$, —ON, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$, optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$, $R_5$ and/or $R_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;
or $Ar_1$ and $Ar_2$, if appropriate together with $C_1$–$C_2$alkylene, —O—, —S—, —$NR_6$—, or —(CO)—, form a fused ring;

wherein all radicals $Ar_1$ and $Ar_2$ optionally additionally are substituted by a group having a —O—C-bond or a —O—Si-bond which cleaves upon the action of an acid;

$Ar_3$, $Ar_4$ and $Ar_5$ have one of the meanings given for $Ar_1$ and $Ar_2$ or are or $Ar_3$, $Ar_4$ and $Ar_5$ independently of each other are $C_1$–$C_{12}$alkyl; or are $C_2$–$C_{12}$alkyl which is interrupted by one or more —O—; or are $C_1$–$C_5$haloalkyl; or are $C_3$–$C_{30}$cycloalkyl which optionally is interrupted by one or more —O—, —S—, —$NR_6$—, —O(CO)—, -or —$NR_6$(CO)—;

all of which are unsubstituted or substituted by one or more $C_1$–$C_{12}$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)

NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;
or Ar$_3$ and Ar$_4$, if appropriate together with C$_1$–C$_2$alkylene, —O—, —S—, —NR$_6$—, —(CO)—, form a fused ring;
or Ar$_3$ and Ar$_4$, if appropriate together with C$_1$–C$_2$alkylene, —O—, —S—, —NR$_6$—, —(CO)—, form a 5-, 6-, or 7-membered ring;
wherein all radicals Ar$_3$, Ar$_4$ and Ar$_5$ optionally additionally are substituted by a group having a —O—C-bond or a —O—Si-bond which cleaves upon the action of an acid;
Ar$_6$ is phenyl, or is naphthyl, or is anthracyl, or is phenanthryl or is heteroaryl, all of which are unsubstituted or substituted by one or more C$_1$–C$_5$ alkyl; C$_2$–C$_{12}$alkyl which is interrupted by one or more —O—; or by C$_1$–C$_5$haloalkyl, C$_3$–C$_{30}$cycloalkyl, halogen, —NO$_2$, —CN, phenyl, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$, optionally the substituents —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$ form 5- or 6-membered rings, via the radicals R$_2$, R$_3$, R$_4$ R$_5$ and/or R$_6$, with further substituents on the phenyl, naphthyl, anthracyl, phenanthryl or heteroaryl ring or with one of the carbon atoms of the phenyl, naphthyl, anthracyl, phenanthryl or heteroaryl ring;
X is phenylene, or is naphthylene, or is

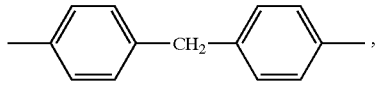

or is diphenylene, or
is oxydiphenylene or is

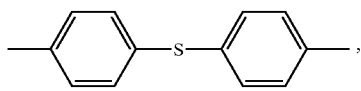

all of which are unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_1$, —SOR$_2$, —SO$_2$R$_2$ and/or —OSO$_2$R$_2$;

or X is 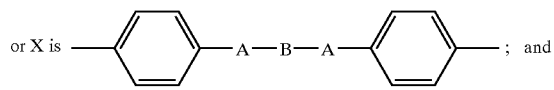 ; and

Y has one of the meanings given for X,
or is C$_1$–C$_{12}$alkylene; or C$_2$–C$_{12}$alkylene which is interrupted by one or more C$_3$–C$_{30}$cycloalkylene, —O—, —S—, —NR$_6$—, —(CO)—, —O(CO)—, —S(CO)—, —NR$_6$(CO)—, —SO—, —SO$_2$—, or —OSO$_2$—;
wherein the C$_1$–C$_{12}$alkylene and C$_2$–C$_{12}$alkylene are unsubstituted or substituted by one or more C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_5$, —O(CO)NR$_4$R$_5$, —NR$_6$(CO)R$_2$, —NR$_6$(CO)OR$_3$, —OR$_3$, —NR$_4$R$_6$, —SR$_6$, —SOR$_2$, —SO$_2$R$_2$ and/or —OSO$_2$R$_2$;
or Y is C$_3$–C$_{30}$cycloalkylene which optionally is interrupted by one or more —O—, —S—, —NR$_6$—, —(CO)—, —O(CO)—, or —NR$_6$(CO)—, and which is unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;
provided that
(i) if at least one Ar$_3$, Ar$_4$ and Ar$_5$ is methyl, then R$_1$ is not methyl, and
(ii) if at least one Ar$_3$, Ar$_4$ and Ar$_5$ is ethyl, then R$_1$ is not ethyl.

Onium sulfates (of formulae Ia, Ib, Ic, IIa, IIb and IIc) can generally be prepared by ionexchange reaction, for example, between the desired onium (iodonium and sulfonium) chloride, bromide, iodide, hydrogen sulfate, tetrafluoroborate, tosylate or methanesulfonate and the desired sulfate salts having ammonium, tetramethylammonium, sodium, lithium, potassium or silver as cation.

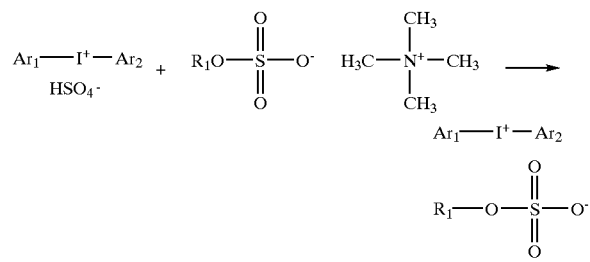

R$_1$, Ar$_1$ and Ar$_2$ are defined as described above.

These reactions usually are carried out in an inert solvent, for example water, methanol, ethanol, methylene chloride, acetone, methyl ethyl ketone, chloroform, chlorobenzene, tert-butyl methyl ether, di-iso-propyl ether, ethyl acetate, hexane, toluene, tetrahydrofuran (THF), dimethylformamide (DMF) or mixture of such solvents. The combination of solvents, for example water and methylene chloride, affords a two phase system. Such two phase systems are also suitable for the ion-exchange reaction. These reactions are well known to those skilled in the art, and are generally carried out at temperatures in the range of 0 to 120° C., preferably 20 to 80° C.

The onium salts required as starting materials can be obtained by a variety of methods described, for instance, by J. V. Crivello in Advances in Polymer Science 62, 1–48, (1984). For example, the desired iodonium salts can be prepared by coupling of two aryl compounds with iodyl sulfate in sulfuric acid, coupling of two aryl compounds with an iodate in acetic acid/acetic anhydride/sulfuric acid, coupling of two aryl compounds with iodine(III) acylate in the presence of an acid, condensation of an aryl iodoso diacetate or an aryl iodoxy compound with another aryl compound in the presence of an acid. Another example is the condensation of a iodoaryl compound with another aryl compound in peroxodisulfate/sulfuric acid as is described in JP-A-59-163330. The desired sulfonium salts can, for example, be prepared by reaction of an aryl compound with sulfur monochloride in the presence of chlorine and Lewis acid, reaction of an aryl Grignard reagent with a diaryl sulfoxide, condensation of a diaryl sulfoxide with an aryl compound in the presence of an acid, or the reaction of a diaryl sulfide with a diaryliodonium salt in the presence of a copper(II) salt.

The sulfate salts required as starting materials can be obtained by a variety of methods described in standard chemistry textbooks (for instance in Comprehensive Organic Chemistry, Vol. 3, Pergamon, 1979), for example, the sulfation of alkenes and alcohols. Sulfuric acid, sulfur trioxide and its amine and ether adducts, chlorosulfuric acid, and sulfamic acid are the common sulfating reagents. One of the most convinient methods is, for example the reaction of alcohol with a sulfur trioxide/amine complex in inert solvents like DMF, THF, methylene chloride, acetone, methyl ethyl ketone, chloroform, chlorobenzene, tert-butyl methyl ether, di-iso-propyl ether, ethyl acetate, hexane, toluene or mixtures of such solvents. These reactions are generally carried out at temperatures in the range of 0 to 120° C., preferably 20 to 80° C.

Interesting are compounds of the formula Ia, Ib, Ic, IIa, IIb and IIc, wherein $Ar_1$ and $Ar_2$ independently of each other are phenyl, which is unsubstituted or substituted by one or more $C_1-C_{12}$alkyl, $C_1-C_5$haloalkyl, $C_3-C_{30}$cycloalkyl; by $C_3-C_{30}$cycloalkyl which is interrupted by one or more —O—, —S—, —NR_6—, —O(CO)—, or —NR_6(CO)—; or is substituted by halogen, —NO_2, —CN, —Ar_6, —(CO)R_2, —(CO)OR_3, —(CO)NR_4R_5, —O(CO)R_2, —O(CO)OR_3, —O(CO)NR_4R_5, —NR_4(CO)R_2, —NR_6(CO)OR_3, —OR_3, —NR_4R_5, —SR_6, —SOR_2, —SO_2R_2 and/or —OSO_2R_2, optionally the substituents —(CO)R_2, —(CO)OR_3, —(CO)NR_4R_5, —O(CO)R_2, —O(CO)OR_3, —O(CO)NR_4R_5, —NR_6(CO)R_2, —NR_6(CO)OR_3, —OR_3, —NR_4R_6, —SR_6, —SOR_2, —SO_2R_2 and/or —OSO_2R_2 form 5- or 6-membered rings, via the radicals $R_2, R_3, R_4 R_5$ and/or $R_6$, with further substituents on the phenyl ring or with one of the carbon atoms of the phenyl ring;

wherein all radicals $Ar_1$ and $Ar_2$ optionally additionally are substituted by a group having a —O—C-bond or a —O—Si-bond which cleaves upon the action of an acid;

$Ar_3$, $Ar_4$ and $Ar_5$ independently of each other are phenyl, which is unsubstituted or substituted by one or more $C_1-C_{12}$alkyl, $C_1-C_5$haloalkyl; $C_3-C_{30}$cycloalkyl optionally interrupted by one or more —O—, —S—, —NR_6—, —O(CO)—, or —NR_6(CO)—; or is substituted by halogen, —NO_2, —CN, —Ar_6, —(CO)R_2, —(CO)OR_3, —(CO)NR_4R_5, —O(CO)R_2, —O(CO)OR_3, —O(CO)NR_4R_5, —NR_6(CO)R_2, —NR_6(CO)OR_3, —OR_3, —NR_4R_5, —SR_6, —SOR_2, —SO_2R_2 and/or —OSO_2R_2, optionally the substituents —(CO)R_2, —(CO)OR_3, —(CO)NR_4R_5, —O(CO)R_2, —O(CO)OR_3, —O(CO)NR_4R_5, —NR_6(CO)R_2, —NR_6(CO)OR_3, —OR_3, —NR_4R_5, —SR_6, —SOR_2, —SO_2R_2 and/or —OSO_2R_2 form 5- or 6-membered rings, via the radicals $R_2, R_3, R_4 R_5$ and/or $R_6$, with further substituents on the phenyl ring or with one of the carbon atoms of the phenyl ring;

wherein all radicals $Ar_3$, $Ar_4$ and $Ar_5$ optionally additionally are substituted by a group having a —O—C-bond or a —O—Si-bond which cleaves upon the action of an acid;

X and Y independently of one another are phenylene,

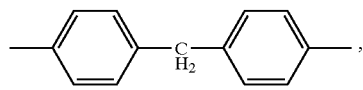

diphenylene, oxydiphenylene or

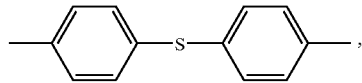

wherein these radicals are unsubstituted or substituted by one or more $C_1-C_5$alkyl, $C_1-C_5$haloalkyl, $C_3-C_{30}$cycloalkyl, halogen, —NO_2, —CN, —Ar_6, —(CO)R_2, —(CO)OR_3, —(CO)NR_4R_5, —O(CO)R_2, —O(CO)OR_3, —O(CO)NR_4R_5, —NR_6(CO)R_2, —NR_6(CO)OR_3, —OR_3, —NR_4R_5, —SR_6, —SOR_2, —SO_2R_2 and/or —OSO_2R_2; and all other radicals are as defined above.

Interesting are further compositions comprising compounds of formula Ia, Ib, Ic, IIa, IIb and IIc, as well as the compounds of formula Ia, Ib, Ic, IIa, IIb and IIc as such, wherein $R_1$ is $C_1-C_5$ alkyl which is unsubstituted or is substituted by one or more; $C_3-C_8$cycloalkyl which optionally is interrupted by one or more —O—, —O(CO)—, or —NR_6(CO)—; or is substituted by halogen, —Ar_6, —(CO)R_2, —(CO)OR_3, and/or —O(CO)R_2;

or $R_1$ is phenyl, which is unsubstituted or substituted by one or more $C_1-C_5$ alkyl, $C_1-C_5$haloalkyl, halogen, —NO_2, —CN, —Ar_6, —(CO)R_2, —O(CO)R_2, —NR_6(CO)R_2, —OR_3, —NR_4R_5, —SR_6, —SO_2R_2 and/or —OSO_2R_2; optionally the substituents, —(CO)R_2, —O(CO)R_2, —NR_6(CO)R_2, —OR_3, —NR_4R_5, —SR_6, —SO_2R_2 and/or —OSO_2R_2 form 5- or 6-membered rings, via the radicals $R_2, R_3, R_4, R_5$ and/or $R_6$, with further substituents on the phenyl ring or with one of the carbon atoms of the phenyl ring;

or $R_1$ is naphthyl, which is unsubstituted or substituted by one or more $C_1-C_5$alkyl, $C_1-C_5$haloalkyl, halogen, and/or —OR_3;

wherein all radicals $R_1$ optionally additionally are substituted by a group having a —O—C-bond or a —O—Si-bond which cleaves upon the action of an acid;

$R'_1$ is $C_1-C_{12}$alkylene or $C_2-C_{12}$alkylene which is interrupted by one or more $C_3-C_{30}$cycloalkylene, —O—, —O(CO)—, or —NR_6(CO)—;

or $R'^1$ is $C_3-C_{30}$cycloalkylene which optionally is interrupted by one or more —O—, —O(CO)— or —NR_6(CO)—;

or $R'_1$ is phenylene, naphthylene;

$R_2$ is phenyl, or is $C_3-C_{30}$cycloalkyl, or is $C_1-C_5$alkyl, all of which are unsubstituted or substituted by phenyl, OH, $C_1-C_5$alkyl, $C_1-C_5$haloalkyl, $C_3-C_{30}$cycloalkyl, halogen, $C_1-C_4$alkoxy and/or phenoxy;

$R_3$ is phenyl, or is $C_3-C_{30}$cycloalkyl, or is $C_1-C_5$alkyl; or is $C_2-C_5$alkyl which is interrupted by one or more —O—; or is $C_3-C_{30}$cycloalkyl which is interrupted by one or more —O—, —O(CO)—, or —NR_6(CO)—; or is $C_2-C_{18}$alkanoyl, or is benzoyl, or is $C_1-C_{18}$alkylsulfonyl; all of which are unsubstituted or substituted by phenyl, OH, $C_1-C_5$alkyl, $C_1-C_5$haloalkyl, $C_3-C_{30}$cycloalkyl, halogen and/or $C_1-C_4$alkoxy;

or $R_3$ is hydrogen, phenylsulfonyl, (4-methylphenyl)sulfonyl or naphthylsulfonyl;

$R_4$, $R_5$ and $R_6$ independently of each other are phenyl, or are $C_3-C_{30}$cycloalkyl, or are $C_1-C_5$alkyl; or are $C_2-C_5$alkyl which is interrupted by one or more —O—; or are $C_3-C_{30}$cycloalkyl which is interrupted by one or more —O—, —O(CO)—, or —NR_6(CO)—; or are $C_2-C_{18}$alkanoyl, or are benzoyl, or are $C_1-C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, and/or $C_1$–$C_4$alkoxy;

or $R_4$ and $R_5$ independently of each other are hydrogen, phenylsulfonyl, (4-methylphenyl)sulfonyl or naphthylsulfonyl;

or $R_4$ and $R_5$, together with the nitrogen atom to which they are attached, form a 5-, 6- or 7-membered ring which optionally is interrupted by —O— or by —$NR_6$—;

$Ar_1$, $Ar_2$, $Ar_3$, $Ar_4$ and $Ar_5$ independently of each other are phenyl, which is unsubstituted or substituted by one or more $C_1$–$C_{12}$alkyl, $C_1$–$C_5$haloalkyl, $C_3$–$C_{30}$cycloalkyl, halogen, —O(CO)$R_2$, —O(CO)O$R_3$, —O(CO)$NR_4R_5$, —O$R_3$, and/or —S$R_6$;

wherein all radicals $Ar_1$, $Ar_2$, $Ar_3$, $Ar_4$ and $Ar_5$ optionally additionally are substituted by a group having a —O—C-bond or a —O—Si-bond which cleaves upon the action of an acid;

$Ar_6$ is phenyl, which is unsubstituted or substituted by one or more $C_1$–$C_{12}$alkyl, $C_1$–$C_5$haloalkyl, $C_3$–$C_{30}$cycloalkyl, halogen, —O(CO)$R_2$, —O(CO)O$R_3$, —O(CO)$NR_4R_6$, —O$R_3$, and/or —S$R_6$; and X and Y independently of one another are phenylene,

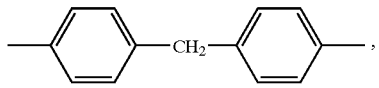

diphenylene, oxydiphenylene or

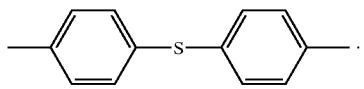

Preferred are compounds of the formula Ia, Ic or IIa, wherein $R_1$ is $C_1$–$C_5$alkyl, $C_1$–$C_{30}$haloalkyl or $C_3$–$C_{30}$cycloalkyl, all of which are unsubstituted or substituted by one or more $C_1$–$C_5$alkyl, —$Ar_6$, —(CO)$R_2$, or by $C_3$–$C_{30}$cycloalkyl, which optionally is interrupted by one or more —O—;

or $R_1$ is phenyl or naphthyl, unsubstituted or substituted by $C_1$–$C_5$alkyl, halogen, —(CO)$R_2$ or —O$R_3$;

$R'_1$ is $C_3$–$C_{30}$cycloalkylene or phenylene;

$R_2$ is phenyl, $C_1$–$C_5$alkyl or hydrogen;

$R_3$ is $C_1$–$C_5$alkyl;

$Ar_1$ and $Ar_2$ independently of each other are phenyl which is unsubstituted or substituted by $C_1$–$C_{12}$alkyl;

$Ar_3$, $Ar_4$ and $Ar_5$ have one of the meanings given for $Ar_1$ and $Ar_2$; and $Ar_6$ is phenyl, naphthyl, anthracyl or heteroaryl, all of which are unsubstituted or substituted by $NO_2$, $C_1$–$C_5$alkyl, or $C_2$–$C_{12}$alkyl which is interrupted by one or more —O—.

Interesting are also compounds of the formula Ia, Ic and IIa, wherein $R_1$ is $C_1$–$C_5$alkyl, unsubstituted or substituted by —$Ar_6$, or is $C_2$–$C_{12}$alkyl which is interrupted by —(CO)—;

or $R_1$ is phenyl, unsubstituted or substituted by $C_1$–$C_5$alkyl or halogen;

$R'_1$ is $C_3$–$C_{30}$cycloalkylene or phenylene;

$Ar_1$ and $Ar_2$ independently of each other are phenyl which is unsubstituted or substituted by $C_1$–$C_{12}$alkyl; and $Ar_3$, $Ar_4$ and $Ar_5$ have one of the meanings given for $Ar_1$ and $Ar_2$.

The compounds of the formula Ia, Ib, Ic, IIa, IIb and IIc can be used as photosensitive acid donors in photocurable compositions. Accordingly, subject of the invention also is a composition comprising (a) a compound which cures upon the action of an acid or a compound whose solubility is increased upon the action of an acid; and (b) as photosensitive acid donor, at least one compound of the formula Ia, Ib, Ic, IIa, IIb or IIc as defined above.

The compounds of formulae Ia, Ib, Ic, IIa, IIb or IIc can be used as photosensitive acid donors in a photoresist. Resist systems can be prepared by image-wise irradiation of systems comprising compounds of formulae Ia, Ib, Ic, IIa, IIb or IIc, followed by a developing step.

A chemically amplified photoresist is understood to be a resist composition wherein the radiation sensitive component provides a catalytic amount of acid which subsequently catalyses a chemical reaction of at least one acid-sensitive component of the resist. Resulting is the induction of a solubility difference between the irradiated and non-irradiated areas of the resist. Because of the catalytic nature of this process one acid molecule can trigger reactions at multiple sites as it diffuses through the reactive polymer matrix, from one reaction site to the next, as long as it is not trapped or destroyed by any secondary reaction. Therefore, a small acid concentration is sufficient to induce a high difference in the solubility between exposed and unexposed areas in the resist. Thus, only a small concentration of the latent acid compound is necessary. As a result, resists with high contrast and high transparency at the exposure wavelength in optical imaging can be formulated, which in turn produce steep, vertical image profiles at high photosensitivity. However, as a result of this catalytic process, it is required that the latent acid catalysts are chemically and thermally very stable (as long as not irradiated) in order not to generate acid during resist storage or during processing, which—in most cases—requires a post exposure bake step to start or to complete the catalytic reaction which leads to the solubility differential. It is also required to have good solubility of the latent catalysts in the liquid resist formulation and the solid resist film to avoid any particle generation which would interfere with the application of these resists in microelectronic manufacturing processes.

Preferred photoresist compositions, comprise the preferred compounds of formula Ia, Ib, Ic, IIa, IIb and. IIc as described above.

Particularly preferred are photoresist compositions comprising at least one compound of the formula Ia, Ib, Ic, IIa, IIb and/or IIc, wherein $R_1$ is $C_1$–$C_5$alkyl which is unsubstituted or substituted by one or more; $C_3$–$C_8$cycloalkyl, which optionally is interrupted by one or more —O—, —O(CO)—, or —$NR_6$(CO)—; or is subtituted by halogen, —$Ar_6$, —(CO)$R_2$, —(CO)O$R_3$, and/or —O(CO)$R_2$;

or $R_1$ is phenyl, which is unsubstituted or substituted by one or more $C_1$–$C_5$alkyl, $C_1$–$C_5$haloalkyl, halogen, —$NO_2$, —CN, —$Ar_6$, —(CO)$R_2$, —O(CO)$R_2$, —$NR_6$(CO)$R_2$, —O$R_3$, —$NR_4R_5$, —S$R_6$, —$SO_2R_2$ and/or —$OSO_2R_2$, optionally the substituents, —(CO)$R_2$, —O(CO)$R_2$, —$NR_6$(CO)$R_2$, —O$R_3$, —$NR_4R_5$, —S$R_6$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl ring or with one of the carbon atoms of the phenyl ring;

or $R_1$ is naphthyl, which is unsubstituted or substituted by one or more $C_1$–$C_5$alkyl, $C_1$–$C_5$haloalkyl, halogen, and/or —O$R_3$;

wherein all radicals $R_1$ optionally additionally are substituted by a group having a —O—C-bond or a —O—Si-bond which cleaves upon the action of an acid;

$R'_1$ is $C_1$–$C_{12}$alkylene; or $C_2$–$C_{12}$alkylene which is interrupted by one or more $C_3$–$C_{30}$cycloalkylene, —O—, —O(CO)—, or —$NR_6$(CO)—;

or R'$_1$ is C$_3$–C$_{30}$cycloalkylene, optionally interrupted by one or more —O—, —O(CO)— or —NR$_6$(CO)—;

or R'$_1$ is phenylene, or naphthylene;

R$_2$ is phenyl, or is C$_3$–C$_{30}$cycloalkyl, or is C$_1$–C$_5$alkyl, all of which are unsubstituted or substituted by phenyl, OH, C$_1$–C$_5$alkyl, C$_1$–C$_5$haloalkyl, C$_3$–C$_{30}$cycloalkyl, halogen, C$_1$–C$_4$alkoxy and/or phenoxy;

R$_3$ is phenyl, or is C$_3$–C$_{30}$cycloalkyl, or is C$_1$–C$_5$alkyl; or is C$_2$–C$_5$alkyl which is interrupted by one or more —O—; or is C$_3$–C$_{30}$cycloalkyl which is interrupted by one or more —O—, —O(CO)—, or —NR$_6$(CO); or is C$_2$–C$_{18}$alkanoyl, or is benzoyl, or is C$_1$–C$_{18}$alkylsulfonyl; all of which are unsubstituted or are substituted by phenyl, OH, C$_1$–C$_5$alkyl, C$_1$–C$_5$haloalkyl, C$_3$–C$_{30}$cycloalkyl, halogen and/or C$_1$–C$_4$alkoxy;

or R$_3$ is hydrogen, phenylsulfonyl, (4-methylphenyl)sulfonyl or naphthylsulfonyl;

R$_4$ and R$_6$ independently of each other are phenyl, or are C$_3$–C$_{30}$cycloalkyl, or are C$_1$–C$_5$alkyl;

or are C$_2$–C$_5$alkyl which is interrupted by one or more —O—; or are C$_3$–C$_{30}$cycloalkyl which is interrupted by one or more —O—, —O(CO)—, or —NR$_6$(CO)—; or are C$_2$–C$_5$alkanoyl, or are benzoyl, or are C$_1$–C$_{18}$alkylsulfonyl, all of which are unsubstituted or are substituted by phenyl, OH, C$_1$–C$_5$alkyl, C$_1$–C$_5$haloalkyl, C$_3$–C$_{30}$cycloalkyl, halogen and/or C$_1$–C$_4$alkoxy;

or R$_4$ and R$_5$ independently of each other are hydrogen, phenylsulfonyl, (4-methylphenyl)sulfonyl or naphthylsulfonyl;

or R$_4$ and R$_5$, together with the nitrogen atom to which they are attached, form a 5-, 6- or 7-membered ring which optionally is interrupted by —O— or by —NR$_6$—;

R$_8$ is phenyl, or is C$_3$–C$_{30}$cycloalkyl, or is C$_1$–C$_5$alkyl; or is C$_2$–C$_5$alkyl which is interrupted by one or more —O—; or is C$_3$–C$_{30}$cycloalkyl which is interrupted by one or more —O—, —O(CO)—, or —NR$_6$(CO)—; or is C$_2$–C$_{18}$alkanoyl, or is benzoyl, or is C$_1$–C$_{18}$alkylsulfonyl, all of which are unsubstituted or are substituted by phenyl, OH, C$_1$–C$_5$alkyl, C$_1$–C$_5$haloalkyl, C$_3$–C$_{30}$cycloalkyl, halogen and/or C$_1$–C$_4$alkoxy;

or R$_8$ is hydrogen, phenylsulfonyl, (4-methylphenyl)sulfonyl or naphthylsulfonyl;

Ar$_1$, Ar$_2$ Ar$_3$, Ar$_4$ and Ar$_5$ independently of each other are phenyl, which is unsubstituted or substituted by one or more C$_1$–C$_{12}$alkyl, C$_1$–C$_5$haloalkyl, C$_3$–C$_{30}$cycloalkyl, halogen, —O(CO)R$_2$, —O(CO)OR$_3$, —O(CO)NR$_4$R$_5$, —OR$_3$, and/or —SR$_6$;

wherein the radicals Ar$_1$, Ar$_2$ Ar$_3$, Ar$_4$ and Ar$_5$ optionally additionally are substituted by a group having a —O—C-bond or a —O—Si-bond which cleaves upon the action of an acid;

Ar$_6$ is phenyl, which is unsubstituted or substituted by one or more C$_1$–C$_{12}$alkyl, C$_1$–C$_5$haloalkyl, C$_3$–C$_{30}$cycloalkyl, halogen, —O(CO)R$_2$, —O(CO)OR$_3$, —O(CO)NR$_4$R$_5$, —OR$_3$, and/or —SR$_6$; and X and Y independently of one another are phenylene,

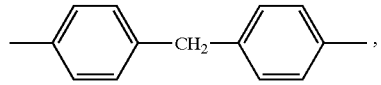

diphenylene, oxydiphenylene or

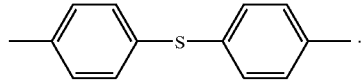

In other preferred compositions according to the invention the radicals R$_1$, Ar$_1$, Ar$_2$, Ar$_3$, Ar$_4$ and/or Ar$_5$ are substituted by a group having a —O—C-bond or a —O—Si-bond which cleaves upon the action of an acid.

The difference in resist solubility between irradiated and non-irradiated sections that occurs as a result of the acid-catalysed reaction of the resist material during or after irradiation of the resist may be of two types depending upon which further constituents are present in the resist. If the compositions according to the invention comprise components that increase the solubility of the composition in the developer after irradiation, the resist is positive.

The invention accordingly relates to a chemically amplified positive photoresist.

If, on the other hand, the components of the formulation reduce the solubility of the composition after irradiation, the resist is negative.

The invention accordingly relates also to a chemically amplified negative photoresist.

A monomeric or polymeric compound which—in the unexposed areas—reduces the dissolution rate of an additionally present alkaline soluble binder resin in the resist formulation and which is essentially alkali-insoluble in the unexposed areas so that the resist film remains in the unexposed area after development in alkaline solution, but which is cleaved in the presence of acid, or is capable of being rearranged, in such a manner that its reaction product becomes soluble in th alkaline developer is referred to hereinafter as dissolution inhibitor.

The invention includes, as a special embodiment a chemically amplified positive alkaline-developable photoresist composition, comprising (a1) at least one polymer having acid-labile groups which decompose in the presence of an acid and increase the solubility of the resist film in an aqueous alkaline developer solution in the exposed area and (b) at least one compound of formula Ia, Ib, Ic, IIa, IIb or IIc.

A further embodiment of the invention is a chemically amplified positive alkaline-developable photoresist composition, comprising (a2) at least one monomeric or oligomeric dissolution inhibitor having at least one acid-labile-group which decomposes in the presence of acid and increases the solubility in an aqueous alkaline developer solution and at least one alkali-soluble polymer and, (b) at least one compound of formula Ia, Ib, Ic, IIa, IIb or IIc.

Another specific embodiment of the invention resides in a chemically amplified positive alkaline-developable photoresist composition, comprising (a1) at least one polymer having acid labile groups which decompose in the presence of an acid and increase the solubility in an alkaline developer in the exposed area;

(a2) a monomeric or oligomeric dissolution inhibitor, having at least one acid labile group, which decomposes in the presence of an acid and increase the alkaline solubility in the exposed area;

(a3) an alkali-soluble monomeric, oligomeric or polymeric compound at a concentration which still keeps the resist film in the unexposed area essentially insoluble in the alkaline developer, and (b) at least one compound of formula Ia, Ib, Ic, IIa, IIb or IIc.

The invention therefore pertains to a chemically amplified photoresist composition, comprising
(a1) at least one polymer having an acid-labile group which decomposes, in the presence of an acid to increase the solubility in aqueous alkaline developer solution and/or
(a2) at least one monomeric or oligomeric dissolution inhibitor having an acid-labile group which decomposes in the presence of an acid to increase the solubility in aqueous alkaline developer solution and/or
(a3) at least one alkali-soluble monomeric, oligomeric or polymeric compound; and
(b) as photosensitive acid donor, at least on e compound of formula Ia, Ib, Ic, IIa, IIb or IIc.

The compositions may comprise additionally to the component (b) other photosensitive acid donors and/or (c) other additives.

Such chemically amplified positive resist systems are described, for example, in E. Reich-manis, F. M. Houlihan, O. Nalamasu, T. X. Neenan, Chem. Mater. 1991, 3, 394; or in C. G. Willson, "Introduction to Microlithography, 2nd. Ed.; L. S. Thompson, C. G. Willson, M. J. Bowden, Eds., Amer. Chem. Soc., Washington D.C., 1994, p. 139.

Suitable examples of acid-labile groups which decompose in the presence of an acid to produce aromatic hydroxy groups, carboxylic groups, keto groups and aldehyde groups and increase the solubility in aqueous alkaline developer solution are, for example, alkoxyalkyl ether groups, tetrahydrofuranyl ether groups, tetrahydropyranyl ether groups, tert.-alkyl ester groups, trityl ether groups, silyl ether groups, alkyl carbonate groups as for example tert.-butyl-oxycarbonyloxy-, trityl ester groups, silyl ester groups, alkoxymethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like.

The polymer having functional groups capable of decomposing by the action of an acid to enhance solubility of the resist film comprising this polymer in an alkaline developing solution, which can be incorporated in the positive resist according to the present invention, may have the acid-labile groups in the backbone and/or side chains thereof, preferably in side chains thereof.

The polymer having acid-labile groups suitable for the use in the present invention can be obtained with a polymer analogous reaction where the alkaline soluble groups are partially or completely converted into the respective acid labile groups or directly by (co)-polymerization of monomers which have the acid labile groups already attached, as is for instance disclosed in EP 254853, EP 878738, EP 877293, JP-A-2-25850, JP-A-3-223860, and JP-A-4-251259.

The polymers which have acid labile groups pendant to the polymer backbone, in the present invention preferably are polymers which have, for example, silylether, acetal, ketal and alkoxyalkylester groups (called "low-activation energy blocking groups") which cleave completely at relatively low post exposure bake temperatures (typically between room temperature and 110° C.) and polymers which have, for example, tert-butylester groups or tert.-butyl-oxycarbonyl (TBOC) groups or other ester groups which contain a secondary or tertiary carbon atom next to the oxygen atom of the ester bond (called "high-activation energy blocking groups") which need higher bake temperatures. (typically >110° C.) in order to complete the deblocking reaction in the presence of acid. Hybrid systems can also be applied, wherein, both, high activation energy blocking groups as well as low activation energy blocking groups are present within one polymer. Alternatively, polymer blends of polymers, each utilizing a different blocking group chemistry, can be used in the photosensitive positive resist compositions according to the invention.

Preferred polymers which have acid labile groups are polymers and co-polymers comprising the following distinct monomer types:
1) monomers that contain acid-labile groups which decompose in the presence of an acid to increase the solubility in aqueous alkaline developer solution and
2) monomers that are free of acid labile groups and free of groups that contribute to the alkaline solubility and/or
3) monomers that contribute to aqueous alkaline solubility of the polymer.

Examples of monomers of type 1) are:
non-cyclic or cyclic secondary and tertiary-alkyl (meth) acrylates such as butyl acrylate, including t-butyl acrylate, butyl methacrylate, including t-butyl methacrylate, 3-oxocyclohexyl (meth)acrylate, tetrahydropyranyl (meth)acrylate, 2-methyl-adamantyl (meth)acrylate, cyclohexyl (meth)acrylate, norbornyl (meth)acrylate, (2-tetrahydropyranyl)oxynorbonylalcohol acrylates, (2-tetrahydropyranyl) oxymethyltricyclododecanemethanol methacrylates, trimethylsilylmethyl (meth)acrylate, (2-tetrahydropyranyl) oxynorbonylalcohol acrylates, (2-tetrahydropyranyl) oxymethyltricyclododecanemethanol methacrylates, trimethylsilylmethyl (meth)acrylate o-/m-/p-(3-oxocyclohexyloxy)styrene, o-/m-/p-(1-methyl-1-phenylethoxy)styrene, o-/m-/p-tetrahydropyranyloxystyrene, o-/m-/p-adamantyloxystyrene, o-/m-/p-cyclohexyloxystyrene, o-/m-/p-norbornyloxystyrene, non-cyclic or cyclic alkoxycarbonylstyrenes such as o-/m-/p-butoxycarbonylstyrene, including p-t-butoxycarbonylstyrene, o-/m-/p-(3-oxocyclohexyloxycarbonyl)-styrene, o-/m-/p-(1-methyl-1-phenylethoxycarbonyl)styrene, o-/m-/p-tetrahydropyranyloxycarbonylstyrene, o-/m-/p-adamantyloxycarbonylstyrene, o-/m-/p-cyclohexyloxycarbonylstyrene, o-/m-/p-norbornyloxycarbonylstyrene, non-cyclic or cyclic alkoxycarbonyloxystyrenes such as o-/m-/p butoxycarbonyloxystyrene, including p t-butoxycarbonyloxystyrene, o-/m/-/p-(3-oxocyclohexyloxycarbonyloxy)styrene, o-/m-/p (1-methyl-1-phenylethoxycarbonyloxy)-styrene, o-/m-/p-tetrahydropyranyloxycarbonyloxystyrene, o-/m-/p-adamantyloxycarbonyloxystyrene, o-/m-/p-cyclohexyloxycarbonyloxystyrene, o-/m-/p-norbornyloxycarbonyloxystyrene, non-cyclic or cyclic alkoxycarbonylalkoxystyrenes such as o/m/p-butoxycarbonylmethoxystyrene, p-t-butoxycarbonylmethoxystyrene, o-/m-/p-(3-oxocyclohexyloxycarbonylmethoxy)-styrene, o-/m-/p-(1-methyl-1-phenylethoxycarbonylmethoxy)styrene, o-/m-/p-tetrahydropyranyloxycarbonylmethoxystyrene, o-/m-/p-adamantyloxycarbonylmethoxystyrene, o-/m-/p-cyclohexyloxycarbonylmethoxystyrene, o-/m-/p-norbornyloxycarbonylmethoxystyrene, trimethylsiloxystyrene, dimethyl(butyl)siloxystyrene, unsaturated alkyl acetates such as isopropenyl acetate and the derivatives of thereof.

Monomers of type 1) bearing low activation energy acid labile groups include, for example, p- or m-(1-methoxy-1-methylethoxy)-styrene, p- or m-(1-methoxy-1- methylethoxy)-methyl-styrene p- or m-(1-methoxy-1-methylpropoxy)styrene, p- or m-(1-methoxy-1-methylpropoxy) methylstyrene, p- or m-(1-methoxyethoxy)-styrene, p- or m-(1-methoxyethoxy)-methylstyrene, p- or m-(1-ethoxy-1-methylethoxy)styrene, p- or m-(1-ethoxy-1-methylethoxy)-methylstyrene, p- or m-(1-ethoxy-1-methylpropoxy)styrene, p- or m-(1-ethoxy-1-methylpropoxy)-methylstyrene, p- or m-(1-ethoxyethoxy) styrene, p- or m-(1-ethoxyethoxy)-methylstyrene, p-(1-ethoxyphenyl-ethoxy)styrene, p- or m-(1-n-propoxy-1-metylethoxy)styrene, p- or m-(1-n-propoxy-1-metylethoxy)-methylstyrene, p- or m-(1-n-propoxyethoxy) styrene, p- or m-(1-n-propoxyethoxy)-methylstyrene, p- or m-(1-isopropoxy-1-methylethoxy)styrene, p- or m-(1-isopropoxy-1-methylethoxy)-methylstyrene, p- or m-(1-isopropoxyethoxy)styrene, p- or m-(1-isopropoxyethoxy)-methylstyrene/, p- or m-(1-isopropoxy-1-methylporpoxy) styrene, p- or m-(1-isopropoxy-1-methylporpoxy)-methylstyrene, p- or m-(1-isopropoxyporpoxy)styrene, p- or m-(1-isopropoxyporpoxy)-methylstyrene, p- or m-(1-n-butoxy-1-methylethoxy)styrene, p- or m-(1-n-butoxyethoxy)styrene, p- or m-(1-isobutoxy-1-methylethoxy)styrene, p- or m-(1-tert-butoxy-1-methylethoxy)styrene, p- or m-(1-n-pentoxy-1-methylethoxy)styrene, p- or m-(1-isoamyloxy-1-methylethoxy)styrene, p- or m-(1-n-hexyloxy-1-methylethoxy)styrene, p- or m-(1-cyclohexyloxy-1-methylethoxy)styrene, p- or m-(1-trimethylsilyloxy-1-methylethoxy)styrene, p- or m-(1-trimethylsilyloxy-1-methylethoxy)-methylstyrene, p- or m-(1-benzyloxy-1-methylethoxy)styrene, p- or m-(1-benzyloxy-1-methylethoxy)-α-methylstyrene, p- or m-(1-methoxy-1-methylethoxy)styrene/,p- or m-(1-methoxy-1-methylethoxy)-α-methylstyrene, p- or m-(1-trimethylsilyloxy-1-methylethoxy)styrene p- or m-(1-trimethylsilyloxy-1-methylethoxy)-methylstyrene. Other examples of polymers having alkoxyalkylester acid labile groups are given in U.S. Pat. No. 5,225,316 and EP 829766. Examples of polymers with acetal blocking groups are given in U.S. Pat. No. 5,670,299, EP 780732, U.S. Pat. Nos. 5,627,006, 5,558,976, 5,558,971, 5,468,589, EP 704762, EP 769206, EP 342498, EP 553737 and described in ACS Symp. Ser. 614, Microelectronics Technology, pp. 35–55 (1995) and J. Photopolymer Sci. Technol. Vol. 10, No. 4 (1997), pp. 571–578, as well as in J. Photo-polym. Sci. Technol. Vol. 12, no. 4 (1999), pp. 591–600. The polymer used in the present invention is not limited thereto.

With respect to polymers having acetal groups as acid-labile groups, it is possible to incorporate acid labile crosslinks as described in H.-T. Schacht, P. Falcigno, N. Muenzel, R. Schulz, and A. Medina, ACS Symp. Ser. 706 (Micro- and Nanopatterning Polymers), p. 78–94, 1997; H.-T. Schacht, N. Muenzel, P. Falcigno, H. Hofzwarth, and J. Schneider, J. Photopolymer Science and Technology, Vol. 9, (1996), 573–586. This crosslinked system is preferred from the standpoint of heat resistance of the resist patterns.

Monomers with high activation energy acid labile groups are, for example, p-tert.-butoxycarbonyloxystyrene, tert.-butyl-acrylate, tert.-butyl-methacrylate, 2-methyl-2-adamantyl-methacrylate, isobornyl-methacrylate.

Examples of comonomers according to type 2) are:
aromatic vinyl monomers, such as styrene, α-methylstyrene, acetoxystyrene, α-methylnaphthylene, acenaphthylene, vinyl alicyclic compounds such as vinyl norbornane, vinyl adamantane vinyl cyclohexane, alkyl (meth) acrylates such as methyl methacrylate, acrylonitrile, vinylcyclohexane, vinylcyclohexanol, as well as maleic anhydride.

Examples of comonomers according to type 3) are:
vinyl aromatic compounds such as hydroxystyrene, acrylic acid compounds such as methacrylic acid, ethylcarbonyloxystyrene and derivatives of thereof. These polymers are described, for example, in U.S. Pat. Nos. 5,827,634, 5,625,020, 5,492,793, 5,372,912, EP 660187, U.S. Pat. No. 5,679,495, EP 813113 and EP 831369. The polymer used in the present invention is not limited thereto.

The content of acid labile monomers in the polymer may vary over a wide range and depends on the amount of the other comonomers and the alkaline solubility of the deprotected polymer. Typically, the content of monomers with acid labile groups in the polymer is between 5 and 60 mol %. If the content is too small, too low development rates and residues of the resist in the exposed areas result. If the content of acid labile monomers is too high, resist patterns are poorly defined (eroded) after development and narrow features cannot be resolved anymore and/or the resist looses its adhesion to the substrate during development. Preferably the copolymers which have acid labile groups have a $M_W$ of from about 3,000 to about 200,000, more preferably from about 5,000 to about 50,000 with a molecular weight distribution of about 3 or less, more preferably a molecular weight distribution of about 2 or less. Non-phenolic polymers, e.g. a copolymer of an alkyl acrylate such as t-butyl acrylate or t-butyl-methacrylate and a vinyl alicyclic compound, such as a vinyl norbonanyl or vinyl cyclohexanol compound, also may be prepared by such free radical polymerization or other known procedures and suitably will have a $M_W$ of from about 8,000 to about 50,000, and a molecular weight distribution of about 3 or less.

Other comonomers may suitably be added in an appropriate amount for the purpose of controlling the glass transition point of the polymer and the like.

In the present invention a mixture of two or more polymers having acid-labile groups may be used. For example, use may be made of a mixture of a polymer having acid-labile groups, which are cleaved very easily, such as acetal groups or tetrahydropyranyloxy groups and a polymer having acid-cleavable groups, that are less easily cleaved, such as for example tertiary alkyl ester groups. Also, acid cleavable groups of different size can be combined by blending two or more polymers having different acid cleavable groups, such as a tert-butyl-ester group and 2-methyl-adamantyl group or an 1-ethoxy-ethoxy group and a tetrahydropyranyloxy group. A mixture of a non-crosslinked resin and a crosslinked resin may also be used. The amount of these polymers in the present invention is preferably from 30 to 99% by weight, more preferably from 50 to 98% by weight, based on the total amount of all solid components. An alkali-soluble resin or monomeric or oligomeric compound having no acid-labile groups may be further incorporated into the composition in order to control the alkali solubility.

Examples of polymer blends with polymers having different acid-labile groups are given in EP 780732, EP 679951 and U.S. Pat. No. 5,817,444.

Preferably monomeric and oligomeric dissolution inhibitors (a2) are used in the present invention.

The monomeric or oligomeric dissolution inhibitor having the acid-labile group for use in the present invention is a compound which has at least one acid-labile group in the molecular structure, which decomposes in the presence of acid to increase the solubility in aqueous alkaline developer solution. Examples are alkoxymethyl ether groups, tetrahydrofuranyl ether groups, tetrahydropyranyl ether groups, alkoxyethyl ether groups, trityl ether groups, silyl ether groups, alkyl carbonate groups, trityl ester groups, silyl ester groups, alkoxyrnethyl ester groups, vinyl carbamate groups, tertiary alkyl carbamate groups, trityl amino groups, cumyl ester groups, acetal groups, ketal groups, tetrahydropyranyl ester groups, tetrafuranyl ester groups, tertiary alkyl ether groups, tertiary alkyl ester groups, and the like. The molecular weight of the acid-decomposable dissolution inhibitive compound for use in the present invention is 3,000 or lower, preferably from 100 to 3,000, more preferably from 200 to 2'500.

Examples of monomeric and oligomeric dissolution inhibitors having acid-labile groups are described as formulae (I) to (XVI) in EP 0831369. Other suitable dissolution inhibitors having acid-labile groups are shown in U.S. Pat. Nos. 5,356,752, 5,037,721, 5,0155,54, JP-A-1-289946, JP-A-1-289947, JP-A-2-2560, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A-4-1651, JP-A-11260, JP-A-4-12356, JP-A-4-123567, JP-A-1-289946, JP-A-3-128959, JP-A-3-158855, JP-A-3-179353, JP-A-3-191351, JP-A-3-200251, JP-A-3-200252, JP-A-3-200253, JP-A-3-200254, JP-A-3-200255, JP-A-3-259149, JA-3-279958, JP-A-3-279959, JP-A-4-1650, JP-A41651, JP-A-11260, JP-A-4-12356, JP-A-4-12357 and Japanese Patent Applications Nos. 3-33229, 3-230790,3-320438, 4-254157, 4-52732, 4-103215, 4-104542, 4-107885, 4-107889, 4-152195, 4-254157, 4-103215, 4-104542, 4-107885, 4-107889, and 4-152195.

The composition can also contain polymeric dissolution inhibitors, for example, polyacetals as described for example in U.S. Pat. No. 5,354,643 or poly-N,O-acetals for example those described in U.S. Pat. No. 5,498,506, either in combination with an alkaline soluble polymer, or in combination with a polymer containing acid labile groups which increase the solubility of the resist film in the developer after exposure, or with a combination of both types of polymers.

In the case where the dissolution inhibitor having acid-labile groups is used in the present invention in combination with the onium salts of formula Ia, Ib, Ic, IIa, IIb or IIc, the alkali-soluble polymer and/or the polymer having acid-labile groups, the amount of the dissolution inhibitor is from 3 to 55% by weight, preferably from 5 to 45% by weight, most preferably from 10 to 35% by weight, based on the total amount of all solid components of the photosensitive composition.

A polymer soluble in an aqueous alkali solution (a3) is preferably used in the present invention. Examples of these polymers include novolak resins, hydrogenated novolak resins, acetone-pyrogallol resins, poly(o-hydroxystyrene), poly(m-hydroxystyrene), poly(p-hydroxystyrene), hydrogenated poly(hydroxystyrene)s, halogen- or alkyl-substituted poly(hydroxystyrene)s, hydroxystyrene/N-substituted maleimide copolymers, o/p- and m/p-hydroxystyrene copolymers, partially o-alkylated poly(hydroxystyrene)s, (e.g., o-methylated, o-(1-methoxy)ethylated, o-(1-ethoxy)ethylated, o-2-tetrahydropyranylated, and o-(t-butoxycarbonyl)methylated poly(hydroxystyrene)s having a degree of substitution of from 5 to 30 mol % of the hydroxyl groups], o-acylated poly(hydroxystyrene)s [e.g., o-acetylated and o-(t-butoxy)carbonylated poly(hydroxystyrene)s having a degree of substitution of from 5 to 30 mol % of the hydroxyl groups], styrene/maleic anhydride copolymers, styrene/hydroxystyrene copolymers, α-methylstyrene/hydroxystyrene copolymers, carboxylated methacrylic resins, and derivatives thereof. However, the alkali-soluble polymer for use in the present invention should not be construed as being limited to these examples.

Especially preferred alkali-soluble polymers (a3) are novolak resins, poly(o-hydroxystyrene), poly(m-hydroxystyrene), poly(p-hydroxystyrene), copolymers of the respective hydroxystyrene monomers, for example, with p-vinylcyclohexanol, alkyl-substituted poly(hydroxystyrene)s, partially o- or m-alkylated and o- or m-acylated poly(hydroxystyrene)s, styrene/hydroxystyrene copolymer, and α-methylstyrene/hydroxystyrene copolymers. The novolak resins are obtained by addition-condensing one or more given monomers as the main ingredient with one or more aldehydes in the presence of an acid catalyst.

Examples of monomers useful in preparing alkaline soluble resins include hydroxylated aromatic compounds such as phenol, cresols, i.e., m-cresol, p-cresol, and o-cresol, xylenols, e.g., 2,5-xylenol, 3,5-xylenol, 3,4-xylenol, and 2,3-xylenol, alkoxyphenols, e.g., p-methoxyphenol, m-methoxyphenol, 3,5-dimethoxyphenol, 2-methoxymethylphenol, m-ethoxyphenol, p-ethoxyphenol, m-propoxyphenol, p-propoxyphenol, m-butoxyphenol, and p-butoxyphenol, dialkylphenols, e.g., 2-methyl-4-isopropylphenol, and other hydroxylated aromatics including m-chlorophenol, p-chlorophenol, o-chlorophenol, dihydroxybiphenyl, bisphenol A, phenyl-phenol, resorcinol, and naphthol. These compounds may be used alone or as a mixture of two or more thereof. The main monomers for novolak resins should not be construed as being limited to the above examples.

Examples of the aldehydes-for polycondensation with phenolic compounds to obtain novolaks include formaldehyde, p-formaldehyde, acetaldehyde, propionaldehyde, benzaldehyde, phenylacetaldehyde, α-phenylpropionaldehyde, β-phenylpropionaldehyde, o-hydroxybenzaldehyde, m-hydroxybenzaldehyde, p-hydroxybenzaldehyde, o-chlorobenzaldehyde, m-chlorobenzaldehyde, p-chlorobenzaldehyde, o-nitrobenzaldehyde, m-nitrobenzaldehyde, o-methylbenzaldehyde, m-methylbenzaldehyde, p-methylbenzaldehyde, p-ethylbenzaldehyde, p-n-butylbenzaldehyde, furfural, chloroacetaldehyde, and acetals derived from these, such as chloroacetaldehyde diethyl acetal. Preferred of these is formaldehyde.

These aldehydes may be used alone or in combination of two or more thereof. Examples of the acid catalyst include hydrochloric acid, sulfuric acid, formic acid, acetic acid, and oxalic acid.

The weight-average molecular weight of the thus-obtained novolak resin suitably is from 1,000 to 30,000. If the weight-average molecular weight thereof is lower than 1,000, the film reduction at unexposed parts during development is liable to be large. If the weight-average molecular weight there of exceeds 50,000, the developing rate may be too low. The especially preferred range of the molecular weight of the novolak resin is from 2,000 to 20,000.

The poly(hydroxystyrene)s and derivatives and copolymers thereof shown above as alkali-soluble polymers other than novolak resins each have a weight-average molecular weight of 2,000 or higher, preferably from 4,000 to 200,000, more preferably from 5,000 to 50,000. From the standpoint of obtaining a polymer film having improved heat resistance, the weight-average molecular weight thereof is desirably at least 5,000 or higher.

Weight-average molecular weight in the context of the present invention is meant to be the one determined by gel permeation chromatography and calibrated for with polystyrene standard.

In the present invention the alkali-soluble polymers may be used as a mixture of two or more thereof. In the case where a mixture of an alkali-soluble polymer and the polymer having groups which decompose by the action of an acid to enhance solubility in an alkaline developing solution is used, the addition amount of the alkali-soluble polymer is preferably up to 80% by weight, more preferably up to 60% by weight, most preferably up to 40% by weight, based on the total amount of the photosensitive composition (excluding the solvent). The amount exceeding 80% by weight is undesirable because the resist pattern suffers a considerable decrease in thickness, resulting in poor images and low resolution.

In the case where an alkali-soluble polymer is used together with a dissolution inhibitor, without the polymer having groups which decompose by the action of an acid, to enhance solubility in an alkaline developing solution, the amount of the alkali-soluble polymer is preferably from 40% to 90% by weight, more preferably from 50 to 85% by weight, most preferably 60 to 80% by weight. If the amount thereof is smaller than 40% by weight, undesirable results such as reduced sensitivity are caused. On the other hand, if it exceeds 90% by weight, the resist pattern suffers a considerable decrease in film thickness, resulting in poor resolution and image reproduction.

The content of the onium salts of formula Ia, Ib, Ic, IIa, IIb or IIc, (component (b)) in the positive resist according to the present invention is preferably between 0.01% to 20% by weight, based on the total amount of all solid components in the photoresist.

The use of the onium salts according to the invention in chemically amplified systems, which operates on the principle of the removal of a protecting group from a polymer, generally produces a positive resist. Positive resists are preferred over negative resists in many applications, especially because of their higher resolution. There is, however, also interest in producing a negative image using the positive resist mechanism, in order to combine the advantages of the high degree of resolution of the positive resist with the properties of the negative resist. This can be achieved by introducing a so-called image-reversal step as described, for example, in EP 361906. For this purpose, the image-wise irradiated resist material is before the developing step treated with, for example, a gaseous base, thereby image-wise neutralizing the acid which has been produced. Then, a second irradiation, over the whole area, and thermal aftertreatment are carried out and the negative image is then developed in the customary manner.

Acid-sensitive components that produce a negative resist characteristically are especially compounds which, when catalysed by an acid (e.g. the acid formed during irradiation of the compounds of formulae Ia, Ib, Ic, IIa, IIb or IIc), are capable of undergoing a crosslinking re-action with themselves and/or with one or more further components of the composition. Compounds of this type are, for example, the known acid-curable resins, such as, for example, acrylic, polyester, alkyd, melamine, urea, epoxy and phenolic resins or mixtures thereof. Amino resins, phenolic resins and epoxy resins are very suitable. Acid-curable resins of this type are generally known and are described, for example, in "Ullmann's Encyclopädie der technischen Chemie" [Ullmanns Enceclopedia of Technical Chemistry], 4th Edition, Vol. 15 (1978), p. 613–628. The crosslinker components should generally be present in a concentration of from 2 to 40, preferably from 5 to 30, percent by weight, based on the total solids content of the negative resist composition.

The invention thus includes, as a special embodiment, chemically amplified negative, alkali-developable photoresists, comprising (a4) an alkali-soluble resin as binder (a5) a component that when catalysed by an acid undergoes a crosslinking reaction with itself and/or with the binder, and (b) as photosensitive acid donor an onium salts of formula Ia, Ib, Ic, IIa, IIb or IIc.

The composition may comprise additionally to the component (b) other photosensitive acid donors and/or (c) other additives.

Especially preferred as acid-curable resins (a5) are amino resins, such as non-etherified or etherified melamine, urea, guanidine or biuret resins, especially methylated melamine resins or butylated melamine resins, corresponding glycolurils and urones. By "resins" in this context, there are to be understood both customary technical mixtures, which generally also comprise oligomers, and pure and high purity compounds. N,N',N''-Hexa(methoxymethyl) melamine and tetramethoxymethyl glucoril and N,N'-dimethoxymethylurone are the acid-curable resins given the greatest preference.

The concentration of the compound of formula Ia, Ib, Ic, IIa, IIb or IIc in negative resists in general is from 0.1 to 30, preferably up to 20, percent by weight, based on the total solids content of the compositions. From 1 to 15 percent by weight is especially preferred.

Where appropriate, the negative compositions may comprise a film-forming polymeric binder (a4). This binder is preferably an alkali-soluble phenolic resin. Well suited for this purpose are, for example, novolaks, derived from an aldehyde, for example acetaldehyde or furfuraldehyde, but especially from formaldehyde, and a phenol, for example unsubstituted phenol, mono- or di-chlorosubstituted phenol, such as p-chlorophenol, phenol mono- or di-substituted by $C_1$–$C_9$alkyl, such as o-, m- or p-cresol, the various xylenols, p-tert-butylphenol, p-nonylphenol, p-phenylphenol, resorcinol, bis(4-hydroxyphenyl)methane or 2,2-bis(4-hydroxyphenyl)propane. Also suitable are homo- and co-polymers based on ethylenically unsaturated phenols, for example homopolymers of vinyl- and 1-propenyl-substituted phenols, such as p-vinylphenol or p-(1-propenyl) phenol or copolymers of these phenols with one or more ethylenically unsaturated materials, for example styrene and styrene derivatives. The amount of binder should generally be from 30 to 95 percent by weight or, preferably, from 40 to 80 percent by weight.

An especially preferred negative resist composition comprises from 0.5 to 15 percent by weight of an onium salt of formula Ia, Ib, Ic, IIa, IIb or IIc (component (b)), from 40 to 99 percent by weight of a phenolic resin as binder (component (a4)), for example one of those mentioned above, and from 0.5 to 30 percent by weight of a melamine resin (component (a5)) as crosslinking agent, the percentages relating to the solids content of the composition. With novolak or especially with polyvinyl phenol as binder, a negative resist having especially good properties is obtained.

Onium salts can also be used as acid generators, which can be activated photochemically, for the acid-catalysed crosslinking of, for example, poly(glycidyl)methacrylates in negative resist systems. Such crosslinking reactions are described, for example, by Chae et al. in *Pollimo* 1993, 17(3), 292.

The positive and the negative resist compositions may comprise in addition to the photosensitive acid donor compound of formula Ia, Ib, Ic, IIa, IIb or IIc further photosensitive acid donor compounds (b1), further additives (c), other photoinitiators (d), and/or sensitizers (e). Therefore, subject of the invention also are chemically amplified resist compositions as described above, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

Onium salts of the present invention in the positive and negative resist can also be used together with other, known photolatent acids (b1), for example, onium salts, 6-nitrobenzylsulfonates, bis-sulionyl diazomethane compounds, cyano group-containing oximesulfonate compounds., etc. Examples of known photolatent acids for chemically amplified resists are described in U.S. Pat. Nos. 5,731,364, 5,800,964, EP 704762, U.S. Pat. Nos. 5,468,589, 5,558,971, 5,558,976 and particularly in EP 794457 and EP 795786.

If a mixture of photolatent acids is used in the resist compositions according to the invention, the weight ratio of onium salts of formula Ia, Ib, Ic, IIa, IIb or IIc to the other photolatent acid (b1) in the mixture is preferably from 1:99 to 99:1.

Examples of photolatent acids which are suitable to be used in admixture with the compounds of formula Ia, Ib, Ic, IIa, IIb or IIc are (1) onium salt compounds, for example, Iodonium salts, sulfonium salts, phosphonium salts, diazonium salts, pyridinium salts. Preferred are diphenyliodonium triflate, diphenyliodonium pyrenesulfonate, diphenyliodonium dodecylbenzenesulfonate, triphenylsulfonium triflate, triphenylsulfonium hexafluoroantimonate, diphenyliodonium hexafluoroantimonate, triphenylsulfonium naphthalenesulfonate, (hydroxyphenyl) benzylmethylsulfonium toluenesulfonate and the like. Particularly preferred are triphenylsulfonium triflate, diphenyliodonium hexafluoroantimonate.

(2) halogen-containing compounds haloalkyl group-containing heterocyclic compounds, haloalkyl group-containing hydrocarbon compounds and the like. Preferred are (trichloromethyl)-s-triazine derivatives such as phenyl-bis(trichloromethyl)-s-triazine, methoxyphenyl-bis(trichloromethyl)-s-triazine, naphthyl-bis-(trichloromethyl)-s-triazine and the like; 1.1-bis(4-chlorophnyl)-2,2,2-trichloroethane; and the like.

(3) sulfone compounds, for example

β-ketosulfones, β-sulfonylsulfones and their α-diazo derivatives and the like. Preferred are phenacylphenylsulfone, mesitylphenacylsulfone, bis(phenylsulfonyl)methane, bis(phenylsulfonyl)diazomethane.

(4) sulfonate compounds, for example alkylsulfonic acid esters, haloalkylsulfonic acid esters, arylsulfonic acid esters, iminosulfonates, imidosulfonates and the like. Preferred imidosulfonate compounds are, for example, N-(trifluoromethlsulfonyloxy)succinimide, N-(trifluoromethylsulfonyloxy)phthalimide, N-(trifluoromethylsulfonyloxy)naphthylimide, N-(trifluoromethylsulfonyloxy)diphenylmaleimide, N-(trifluoromethylsulfonyloxy)-bicyclo-[2,2,1]-hept-5-ene-2,3-dicarboximide, N-(trifluoromethylsulfonyloxy)-7-oxabicyclo-[2,2,1]-hept-5-ene-2,3-dicarboximide, N-(trifluoromethylsulfonyloxy)7-oxabicyclo-[2,2,1]-hept-5-ene-2,3-dicarboximide, N-(trifluoromethylsulfonyloxy)-bicyclo-[2,2,1]-heptan-5,6-oxy-2,3-dicarboximide, N-(camphanylsulfonyloxy)succinimide, N-(camphanylsulfonyloxy)phthalimide, N-(camphanylsulfonyloxy)naphthylimide, N-(camphanylsulfonyloxy)diphenylmaleimide, N-(camphanylsulfonyloxy)bicyclo-[2,2,1]-hept-5-ene-2,3-dicarboximide, N-(camphanylsulfonyloxy)-7-oxabicyclo-[2,2,1]-hept-5-ene-2,3-dicarboximide, N-(camphanylsulfonyloxy)-7-oxabicyclo-[2,2,1]hept-5-ene-2,3-dicarboximide, N-(camphanylsulfonyloxy)-bicyclo-2,2,1]-heptan-5,6-oxy-2,3-dicarboximide, N-(4-methylphenylsulfonyloxy)succinimide, N-(4-methylphenylsulfonyloxy)phthalimide, N-(4-methylphenylsulfonyloxy)naphthylimide, N-(4-methylphenylsulfonyloxy)naphthylimide, N-(4-methylphenylsulfonyloxy)diphenylmaleimide, N-(4-methylphenylsulfonyloxy)-bicyclo-[2,2,1]-hept-5-ene-2,3-dicarboximide, N-(4-methylphenylsulfonyloxy)-7-oxabicyclo-[2,2,1]-hept-5-ene-2,3-dicarboximide, N-(4-methylphenylsulfonyloxy)-bicyclo-[2,2,1]-heptan-5,6-oxy-2,3-dicarboximide, N-(2-trifluoromethylphenylsulfonyloxy)succinimide, N-(2-trifluoromethylphenylsulfonyloxy)naphthylimide, N-(2-trifluoromethylphenylsulfonyloxy)diphenylmaleimide, N-(2-trifluoromethylphenylsulfonyloxy)-bicyclo-[2,2,1]-hept-5-ene-2,3-dicarboximide, N-(2-trifluoromethylphenylsulfonyloxy)-7-oxabicyclo-[2,2,1]-hept-5-ene-2,3-dicarboximide, N-(2-trifluoromethylphenylsulfonyloxy)-bicyclo-[2,2,1]-heptan-5,6-oxy-2,3-dicarboximide and the like.

Other suitable sulfonate compounds preferably are, for example, benzoin tosylate, pyrogallol tristriflate, pyrogallomethanesulfonic acid triester, nitorobenzyl-9,10-diethyoxyanthracene-2-sulfonate, α-(4-toluenesulfonyloxyimino)-benzyl cyanide, α-(4-toluenesulfonyloxyimino)-4-methoxybenzyl cyanide, α-(4-toluenesulfonyloxyimino)-2-thienylmethyl cyanide, α-(methanesulfonyloxyimino)-1-cyclohexenylacetonitrile, α-(butylsulfonyloxyimino)-1-cyclopentenylacetonitrile, (4-methylsufonyloxyimino-cyclohexa-2,5-dienylidene)-phenyl-acetonitdle, (5-methylsulfonyloxyimino-5H-thiophen-2-ylidene)-phenyl-acetonitrile, (5-methylsulfonyloxyimino-5H-thiophen-2-ylidene)-(2-methylphenyl)-acetonitrile, (5-propylsulfonyloxyimino-5H-thiophen-2-ylidene)-(2-methylphenyl)-acetonitrile, (5-(4-methylbenzenesulfonyloxyimino)-5H-thiophen-2-ylidene)-(2-methylphenyl)-acetonitrile, (5-methylsulfonyloxyimino-5H-thiophen-2-ylidene)-(2-chlorophenyl)-acetonitrile, 2,2,2-trifluoro-1-(4-methoxyphenyl)-ethanone oxime-O-methylsulfonate, 2,2,2-trifluoro-1-(4-methoxyphenyl)-ethanone oxime-O-propylsulfonate, 2,2,2-trifluoro-1-(4-methoxyphenyl)-ethanone oxime-O-(10-camphorylsulfonate), 1,3-bis{4-(2,2,2-trifluoro-1-methylsulfonyloxyimino-ethyl)-phenoxy}-propane, 1,3-bis{4-(2,2,2-trifluoro-1-propylsulfonyloxyimino-ethyl)-phenoxy}-propane, 1,3-bis[4-{2,2,2-trifluoro-1-(10-camphor-ylsulfonyloxy)imino-ethyl)-phenox]}-propane, 1,3-bis{4-(2,2,2-trifluoro-1-benzylsulfonyloxyimino-ethyl)-phenoxy}-propane, and the like.

In the radiation sensitive resin composition of this invention, particularly preferred sulfonate compounds include pyrogallolmethanesulfonic acid triester, N-(trifluoromethylsulfonyloxy)bicyclo-[2,2,1]-hept-5-ene-2,3-dicarboximide, N-(camphanylsulfonyloxy) naphthylimide, N-(2-trifluoromethylphenylsulfonyloxy) phthalimide, N-(trifluoromethylsulfonyloxy)-bicyclo-[2,2,1]-hept-5-ene-2,3-dicarboximide, N-(camphanylsulfonyloxy)naphthylimide, N-(2-trifluoromethyl-phenylsulfonyloxy)phthalimide and the like.

(5) Quinonediazide compounds, for example
1,2-quinonediazidesulfonic acid ester compounds of polyhydroxy compounds. Preferred are compounds having a 1,2-quinonediazidesulfonyl group, e.g. a 1,2-benzoquinonediazide-4-sulfonyl group, a 1,2-naphthoquinonedlazide-4-sulfonyl group, a 1,2-naphthoquinonediazide-5-sulfonyl group, a 1,2-naphthoquinonediazide-6-sulfonyl group or the like. Particularly preferred are compounds having a 1,2-naphthoquinonediazide-4-sulfonyl group or a 1,2-naphthoquinonediazide-5-sulfonyl group. In particular suitable are 1,2-quinonediazidesulfonic acid esters of (poly)hydroxyphenyl aryl ketones such as 2,3,4-trihydroxybenzophenone, 2,4,6-trihydroxybenzophenone, 2,3,4,4'-tetrahydroxybenzophenone, 2,2',3,4-tetrahydroxybenzophenone, 2,3,4,4'-tetrahydroxybenzophenone, 2,2',4,4'-tetrahydroxybenzophenone 2,2',3,4,4'-pentahydroxybenzophenone, 2,2'3,2,6'-pentahydroxybenzophenone, 2,3,3',4,4'5'-hexahydroxybenzophenone, 2,3',4,4',5'6-hexahydroxybenzophenone and the like; 1,2-quinonediazidesulfonic acid esters of bis-[(poly)hydroxyphenyl]alkanes such as bis(4-hydroxyphenyl)ethane, bis(2,4-dihydroxyphenyl)ethane, 2,2-bis(4-hydroxyphenyl)propane, 2,2-bis(2,4-dihydroxyphenyl)propane, 2,2-bis-(2,3,4-tridroxyphenyl)propane and the like; 1,2-quinonediazidesulfonic acid esters of (poly)hydroxyphenylalkanes such as 4,4'-dihydroxytriphenylmethane, 4,4'4"-trihydroxytriphenylmethane, 4,4'5,5'-tetramethyl-2,2'2"-trihydroxytriphenylmethane, 2,2,5,5'-tetramethyl-4,4',4"-trihydroxytdphenylmethane, 1,1,1-tris(4-hydroxyphenyl)ethane, 1,1-bis(4-hydroxyphenyl)-1-phenylethane, 1,1-bis(4-hydroxyphenyl)-1-(4-[1-(hydroxyphenyl)-1-methylethyl]phenyl)ethane and the like; 1,2-quinonediazidesulfonic acid esters of (poly)hydroxyphenylflavans such as 2,4,4-trimethyl-2',4',7-trihydroxy-2-phenylflavan, 2,4,4-trimethyl-2',4',5',6,7-pentahydroxy-2-phenylflavan and the like.

The positive and negative photoresist composition of the present invention may optionally contain one or more additives (c) customarily used in photoresists in the customary amounts known to a person skilled in the art, for example, dyes, pigments, plasticizers, surfactants, flow improvers, wetting agents, adhesion promoters, thixotropic agents, colourants, fillers, solubility accelerators, acid-amplifier, photosensitizers and organic basic compounds.

Examples for organic basic compounds which can be used in the resist composition of the present invention are compounds which are stronger bases than phenol, in particular, nitrogen-containing basic compounds. These compounds may be ionic, like, for example, tetraalkylammonium salts or non-ionic. Preferred organic basic compounds are nitrogen-containing basic compounds having, per molecule, two or more nitrogen atoms having different chemical environments. Especially preferred are compounds containing both at least one substituted or unsubstituted amino group and at least one nitrogen-containing ring structure, and compounds having at least one alkylamino group. Examples of such preferred compounds include guanidine, aminopyridine, amino alkylpyridines, aminopyrrolidine, indazole, imidazole, pyrazole, pyrazine, pyrimidine, purine, imidazoline, pyrazoline, piperazine, aminomorpholine, and aminoalkylmorpholines. Suitable are both, the unsubstituted compounds or substituted derivatives thereof. Preferred substituents include amino, aminoalkyl groups, alkylamino groups, aminoaryl groups, arylamino groups, alkyl groups alkoxy groups, acyl groups acyloxy groups aryl groups, aryloxy groups, nitro, hydroxy, and cyano. Specific examples of especially preferred organic basic compounds include guanidine, 1,1-dimethylguanidine, 1,1,3,3-tetramethylguanidine, 2-aminopyridine, 3-aminopyridine, 4-aminopyridine, 2-dimethylaminopyridine, 4-dimethylaminopyridine, 2-diethylaminopyridine, 2-(aminomethyl)-pyridine, 2-amino-3-methylpyridine, 2-amino-4-methylpyridine, 2-amino-5-methylpyridine, 2-amino-6-methylpyridine, 3-aminoehtylpyridine, 4-aminoethylpyndine, 3-aminopyrrolidine, piperazine, N-(2-aminoethyl)piperazine, N-(2-aminoethyl)piperidine, 4-amino-2,2,6,6-tetramethylpiperidine, 4-piperidinopiperidine, 2-imimopiperidine, 1-(2-aminoethyl)pyrrolidine, pyrazole, 3-amino-5-methylpyrazole, 5-amino-3-methyl-1-p-tolylpyrazole, pyrazine, 2-(aminomethyl)-5-methylpyrazine, pyrimidine, 2,4-diaminopyrimidine, 4,6-dihydroxypyrimidine, 2-pyrazoline, 3-pyrazoline, N-aminomorpholine, and N-(2-aminoethyl)morpholine.

Other examples of suitable organic basic compounds are described in DE 4408318, U.S. Pat. Nos. 5,609,989, 5,556,734, EP 762207, DE 4306069, EP 611998, EP 813113, EP 611998, and U.S. Pat. No. 5,498,506. However, the organic basic compounds suitable in the present invention are not limited to these examples.

The nitrogen-containing basic compounds may be used alone or in combination of two or more thereof. The added amount of the nitrogen-containing basic compounds is usually from 0.001 to 10 parts by weight, preferably from 0.01 to 5 parts by weight, per 100 parts by weight of the photosensitive resin composition (excluding the solvent). If the amount thereof is smaller than 0.001 part by weight, the effects of the present invention cannot be obtained.

On the other hand, if it exceeds 10 parts by weight, reduced sensitivity and impaired develop-ability at unexposed parts are liable to be caused.

The composition can further contain a basic organic compound which decomposes under actinic radiation ("suicide base") such as for example described in EP 710885, U.S. Pat. Nos. 5,663,035, 5,595,855, 5,525,453, and EP 611998.

Examples of dyes (c) suitable for the compositions of the present invention are oil-soluble dyes and basic dyes, e.g. Oil Yellow #101, Oil Yellow #103, Oil Pink #312, Oil Green BG, Oil Blue BOS, Oil Blue #603, Oil Black BY, Oil Black BS, Oil Black T-505 (all manufactured by Orient Chemical Industries Ltd., Japan), crystal violet (CI42555), methyl violet (CI 42535), rhodamine B (CI 45170B), malachite green (CI 42000), and methylene blue (CI52015).

Spectral sensitizers (e) may be further added to sensitize the photo latent acid to exhibit absorption in a region of longer wavelengths than far ultaviolet, whereby the photosensitive composition of the present invention can, for example, be rendered sensitive to an l-line or g-line radiation. Examples of suitable spectral sensitizers include benzophenones, p,p'-tetramethyldiaminobenzophenone, p,p'-tetraethylethylaminobenzophenone, thioxanthone, 2-chlorothioxanthone, 4-propoxy-2-chloro-thioxanthone, anthrone, anthracene, 9,10-diethoxyanthracene, 2-ethyl-9,10-dimethoxyanthracene, pyrene, perylene, phenothiazine, benzil, ac-ridine orange, benzoflavin, cetoflavin T, 9,10-diphenylanthracene, 9-fluorenone, acetophenone, phenanthrene, 2-nitrofluorene, 5-nitroacenaphthene, benzoquinone, 2-chloro-4-nitroaniline, N-acetyl-p-nitroaniline, p-nitroaniline, N-acetyl-4-nitro-1-naphthylamine, picramide, anthraquinone, 2-ethylanthraquinone, 2-tert-butylanthraquinone, 1,2- benzanthraquinone, 3-methyl-1,3-diaza-1,9-benzanthrone, dibenzalacetone, 1,2-naphthoquinone, 3-acylcoumarin derivatives, 3,3'-carbonyl-bis(5,7-dimethoxycarbonylcoumarin), 3-(aroylmethylene) thiazolines, eosin, rhodamine, erythrosine, and coronene. However, the suitable spectral sensitizers are not limited to these examples.

These spectral sensitizers can be used also as light absorbers for absorbing the far ultraviolet emitted by a light source. In this case, the light absorber reduces light reflection from the substrate and lessens the influence of multiple reflection within the resist film, thereby diminishing the effect of standing waves.

Further suitable additives (c) are "acid-amplifiers", compounds that accelerate the acid formation or enhance the acid concentration. Such compounds may also be used in combination with the onium salts of the formulae Ia, Ib, Ic, IIa, IIb or IIc according to the invention in positive or negative resists, or in imaging systems as well as in all coating applications. Such acid amplifiers are described e.g. in Arimitsu, K. et al. J. Photopolym. Sci. Technol. 1995, 8, pp 43; Kudo, K. et al. J. Photopolym. Sci. Technol. 1995, 8, pp 45; Ichimura, K. et al. Chem: Letters 1995, pp 551.

Usually, for the application to a substrate of the photosensitive composition of the present invention, the composition is dissolved in an appropriate solvent. Preferred examples of these solvents include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, 2-ethoxyethyl acetate, 2-ethoxyethanol, diethyl glycol dimethyl ether, ethylene glycol monoethyl ether acetate, propylene glycol monorhethyl ether, propylene glycol monomethyl ether acetate, toluene, ethyl acetate, methyl lactate, ethyl lactate, methyl methoxypropionate, ethyl ethoxypropionate, methylpyruvate, ethyl pyruvate, propyl pyruvate, N,N-dimethylformamide, dimethyl sulfoxide, N-methylpyrrolidone, and tetrahydrofuran. These solvents may be used alone or as mixtures. Preferred examples of the solvents are esters, such as 2-methoxyethyl acetate, ethylene glycolmonoethyl ether acetate, propylene glycol monomethyl ether acetate, methyl methoxypropionate, ethyl ethoxypropionate, and ethyl lactate. Use of such solvents is advantageous because the onium salts represented by formulae Ia, Ib, Ic, IIa, IIb or IIc according to the present invention have good compatibility therewith and better solubility therein.

A surfactant can be added to the solvent. Examples of suitable surfactants include nonionic surfactants, such as polyoxyethylene alkyl ethers, e.g. polyoxyethylene lauryl ether, polyoxyethylene stearyl ether, polyoxyethylene acetyl ether, and polyoxyethylene oleyl ether; polyoxyethylene alkylaryl ethers, e.g. polyoxyethylene, octylphenol ether and polyoxyethylene nonylphenol ether; polyoxyethylene/polyoxypropylene block copolymers, sorbitan/fatty acid esters, e.g. sorbitan monolaurate, sorbitan monopalmitate, sorbitan monostearate, sorbitan monooleate, sorbitan trioleate; fluorochemical surfactants such as F-top EF301, EF303, and EF352 (manufactured by New Akita Chemical Company, Japan). Megafac F171 nad F17.3 (manufactured by Dainippon Ink & Chemicals, Inc,. Japan), Fluorad FC 430 and FC431 (manufactured by Sumitomo #M Ltd., Japan), Asahi Guard AG710 and Surflon S-382, SC101, SC102, SC103, SC104, SC105, and SC106 (manufactured by Asahi Grass Col, Ltd., Japan); organosiloxane polymer KP341 (manufactured by Shin-Etsu Chemical Co., Ltd., Japan); and acrylic or methacrylic (co)polymers Poly-flow Now.75 and NO.95 (manufactured by Kyoeisha Chemical Co., Ltd., Japan). The added amount of the surfactant usually is 2 parts by weight or lower, desirably 0.1 part by weight or lower, per 100 parts by weight of the solid components of the composition of the present invention. The surfactants may be added alone or in combination of two or more thereof.

The solution is uniformly applied to a substrate by means of known coating methods, for example by spin-coating, immersion, knife coating, curtain coating techniques, brush application, spraying and roller coating. It is also possible to apply the photosensitive layer to a temporary, flexible support and then to coat the final substrate by coating transfer (laminating).

The amount applied (coating thickness) and the nature of the substrate (coating substrate) are dependent on the desired field of application. The range of coating thicknesses can in principle include values from approximately 0.01 $\mu$m to more than 100 $\mu$m.

After the coating operation generally the solvent is removed by heating, resulting in a layer of the photoresist on the substrate. The drying temperature must of course be lower than the temperature at which certain components of the resist might react or decompose. In general, drying temperatures should are in the range from 60 to 160° C.

The resist coating is then irradiated image-wise. The expression "image-wise irradiation" includes irradiation in a predetermined pattern using actinic radiation, i.e. both irradiation through a mask containing a predetermined pattern, for example a transparency, a chrome mask or a reticle, and irradiation using a laser beam or electron beam that writes directly onto the resist surface, for example under the control of a computer, and thus produces an image. Another way to produce a pattern is by interference of two beams or images as used for example in holographic applications. It is also possible to use masks made of liquid crystals that can be addressed pixel by pixel to generate digital images, as is, for example described by A. Bertsch; J. Y. Jezequel; J. C. Andre in Journal of Photochemistry and Photobiology A: Chemistry 1997,107 pp. 275–281 and by K. P. Nicolay in Offset Printing 1997, 6, pp. 34–37.

After the irradiation and, if necessary, thermal treatment, the irradiated sites (in the case of positive resists) or the non-irradiated sites (in the case of negative resists) of the composition are removed in a manner known per se using a developer.

In order to accelerate the catalytic reaction and hence the development of a sufficient difference in solubility between the irradiated and unirradiated sections of the resist coating in the developer, the coating is preferably heated before being developed. The heating can also be carried out or begun during the irradiation. Temperatures of from 60 to 160° C. are preferably used. The period of time depends on the heating method and, if necessary, the optimum period can be determined easily by a person skilled in the art by means of a few routine experiments. It is generally from a few seconds to several minutes. For example, a period of from 10 to 300 seconds is very suitable when a hotplate is used and from 1 to 30 minutes when a convection oven is used. It is important for the latent acid donors according to the invention in the unirradiated sites on the resist to be stable under those processing conditions.

The coating is then developed, the portions of the coating that, after irradiation, are more soluble in the developer being removed. If necessary, slight agitation of the workpiece, gentle brushing of the coating in the developer bath or spray developing can accelerate that process step. The aqueous-alkaline developers customary in resist technology may, for example, be used for the development. Such developers comprise, for example, sodium or potassium hydroxide, the corresponding carbonates, hydrogen carbonates, silicates or metasilicates, but preferably metal-free bases, such as ammonia or amines, for example ethylamine, n-propylamine, diethylamine, di-n-propylamine, triethylamine, methyl diethylamine, alkanolamines, for example dimethyl ethanolamine, triethanolamine, quaternary ammonium hydroxides, for example tetramethylammonium hydroxide or tetraethylammonium hydroxide. The developer solutions are generally up to 0.5 N, but are usually diluted in suitable manner before use. For example solutions having a normality of approximately 0.1–0.3 are well suited. The choice of developer depends on the nature of the photocurable surface coating, especially on the nature of the binder used or of the resulting photolysis products. The aqueous developer solutions may, if necessary, also comprise relatively small amounts of wetting agents and/or organic solvents. Typical organic solvents that can be added to the developer fluids are, for example, cyclohexanone, 2-ethoxyethanol, toluene, acetone, isopropanol and also mixtures of two or more of these solvents. A typical aqueous/organic developer system is based on Butylcellosolve$^{RTM}$/water.

Subject of the invention also is a process for the preparation of a photoresist by
(1) applying to a substrate a composition as described above;
(2) post apply baking the composition at temperatures between 60° C. and 160° C.;
(3) image-wise irradiating with light of wavelengths between 150 nm and 1500 nm;
(4) optionally post exposure baking the composition at temperatures between 60° C. and 160° C.; and
(5) developing with a solvent or with an aqueous alkaline developer.

Preferred is a process, wherein the image-wise irradiation is carried out with monochromatic or polychromatic radiation in the wavelength range from 157 to 450 nm, in particular in the range from 190 to 260 nm.

The photoresist compositions can be used on all substrates and with all exposure techniques known to the person skilled in the art. For example, semiconductor substrates can be used, such as silicon, gallium arsenide, germanium, indium antimonide; furthermore substrates covered by oxide or nitride layers, such as silicon dioxide, silicon nitride, titanium nitride, siloxanes, as well as metal substrates and metal coated substrates with metals such as aluminium, copper, tungsten, etc. The substrate can also be coated with polymeric materials, for example with organic antireflective coatings, insulation layers and dielectric coatings from polymeric materials prior to coating with the photoresist.

The photoresist layer can be exposed by all common techniques, such as direct writing, i.e. with a laser beam or projection lithography in step-and repeat mode ore scanning mode, or by contact printing through a mask.

In case of projection lithography a wide range of optical conditions can be used such as coherent, partial coherent or incoherent irradiation. This includes off-axis illumination techniques, for example annular illumination and quadrupol illumination where the radiation is allowed to pass only certain regions of the lens, excluding the lens center.

The mask used to replicate the pattern can be a hard mask or a flexible mask. The mask can include transparent, semitransparent and opaque patterns. The pattern size can include also patterns which are at or below the resolution limit of the projection optics and placed on the mask in a certain way in order to modify the aerial image, intensity and phase modulation of the irradiation after having passed the mask. This includes phase shift masks and halftone phase shift masks.

The patterning process of the photoresist composition can be used to generate patterns of any desired geometry and shape, for example dense and isolated lines, contact holes, trenches, dots, etc.

The photoresists according to the invention have excellent lithographic properties, in particular a high sensitivity, and high resist transparency for the imaging radiation.

Possible areas of use of the composition according to the invention are as follows: use as photoresists for electronics, such as etching resists, electroplating resists or solder resists, the manufacture of integrated circuits or thin film transistor-resist (TFT); the manufacture of printing plates, such as offset printing plates or screen printing stencils, use in the etching of mouldings or in stereolithography or holography techniques. The coating substrates and processing conditions vary accordingly.

The compositions according to the invention are also outstandingly suitable as coating compositions for substrates of all types, including wood, textiles, paper, ceramics, glass, plastics, such as polyesters, polyethylene terephthalate, polyolefins or cellulose acetate, especially in the form of films, but especially for coating metals, such as Ni, Fe, Zn, Mg, Co or especially Cu and Al, and also Si, silicon oxides or nitrides, to which an image is to be applied by means of image-wise irradiation.

The invention relates also to the use of compounds of formula Ia, Ib, Ic, IIa, IIb or IIc as photo-latent acid donors in compositions that can be crosslinked under the action of an acid and/or as dissolution enhancers in compositions wherein the solubility is increased under the action of an acid.

Subject of the invention further is a process of crosslinking compounds that can be crosslinked under the action of an acid, which method comprises adding a compound of formula Ia, Ib, Ic, IIa, IIb and/or tic to the above-mentioned compounds and irradiating imagewise or over the whole area with light having a wavelength of 150–1500 nm.

The invention relates also to the use of compounds of formulae Ia, Ib, Ic, IIa, IIb or IIc as photosensitive acid donors in the preparation of surface coatings, printing inks, printing plates, dental compositions, colour filters, resists or image-recording materials, or image-recording materials for recording holographic images, as well as to a process for the preparation of of surface coatings, printing inks, printing plates, dental compositions, colour filters, resist materials or image-recording materials, or image-recording materials for recording holographic images.

Subject of the invention is also the use of compounds of formulae Ia, Ib, Ic, IIa, IIb or IIc as photosensitive acid donors in the preparation of colour filters or chemically amplified resist materials.

As already mentioned above, in photocrosslinkable compositions, onium salts act as latent curing catalysts: when irradiated with light they release acid which catalyses the crosslinking reaction. In addition, the acid released by the radiation can, for example, catalyse the removal of suitable acid-sensitive protecting groups from a polymer structure, or the cleavage of polymers containing acid-sensitive groups in the polymer backbone. Other applications are, for example, colour-change systems based on a change in the pH or in the solubility of, for example, a pigment protected by acid-sensitive protecting groups.

Onium salts according to the present invention can also be used to produce so-called "print-out" images when the compound is used together with a colourant that changes colour when the pH changes, as described e.g. in JP Hei 4328552-A or in U.S. Pat. No. 5,237,059. Such color-change systems can be used according to EP 199672 also to monitor goods that are sensitive to heat or radiation.

In addition to a colour change, it is possible during the acid-catalysed deprotection of soluble pigment molecules (as described e.g. in EP 648770, EP 648817 and EP 742255) for the pigment crystals to be precipitated; this can be used in the production of colour filters as described e.g. in EP 654711 or print out images and indicator applications, when the colour of the latent pigment precursor differs from that of the precipitated pigment crystal.

Compositions using pH sensitive dyes or latent pigments in combination with onium salts can be used as indicators for electromagnetic radiation, such as gamma radiation, electron beams, UV- or visible light, or simple throw away dosimeters. Especially for light, that is invisible to the human eye, like UV- or IR-light, such dosimeters are of interest.

Finally, onium salts that are sparingly soluble in an aqueous-alkaline developer can be rendered soluble in the developer by means of light-induced conversion into the free acid, with the result that they can be used as solubility enhancers in combination with suitable film-forming resins.

Resins which can be crosslinked by acid catalysis and accordingly by the photolatent acids of formula Ia, Ib, Ic, IIa, IIb or IIc are, for example, mixtures of polyfunctional alcohols or hydroxy-group-containing acrylic and polyester resins, or partially hydrolysed polyvinylacetals or polyvinyl alcohols with polyfunctional acetal derivatives. Under certain conditions, for example the acid-catalysed self-condensation of acetal-functionalised resins is also possible.

Suitable acid-curable resins in general are all resins whose curing can be accelerated by acid catalysts, such as aminoplasts or phenolic resole resins. These resins are for example melamine, urea, epoxy, phenolic, acrylic, polyester and alkyd resins, but especially mixtures of acrylic, polyester or alkyd resins with a melamine resin. Also included are modified surface-coating resins, such as acrylic-modified polyester and alkyd resins. Examples of individual types of resins that are covered by the expression acrylic, polyester and alkyd resins are described, for example, in Wagner, Sarx, Lackkunstharze (Munich, 1971), pp. 86–123 and pp. 229–238, or in Ullmann, Encyclopädie der techn. Chemie, 4th Ed., Vol. 15 (1978), pp. 613–628, or Ullmann's Encyclopedia of Industrial Chemistry, Verlag Chemie, 1991, Vol. 18, p. 360 ff., Vol. A19, p. 371 ff.

In coating applications the surface coating preferably comprises an amino resin. Examples thereof are etherified or non-etherified melamine, urea, guanidine or biuret resins. Acid catalysis is especially important in the curing of surface coatings comprising etherified amino resins, such as methylated or butylated melamine resins (N-methoxymethyl- or N-butoxymethyl-melamine) or methylated/butylated glycolurils. Examples of other resin compositions are mixtures of polyfunctional alcohols or hydroxy-group-containing acrylic and polyester resins, or partially hydrolysed polyvinyl acetate or polyvinyl alcohol with polyfunctional dihydropropanyl derivatives, such as derivatives of 3,4-dihydro-2H-pyran-2-carboxylic acid. Polysiloxanes can also be crosslinked using acid catalysis. These siloxane group-containing resins can, for example, either undergo self-condensation by means of acid-catalysed hydrolysis or be crosslinked with a second component of the resin, such as a polyfunctional alcohol, a hydroxy-group-containing acrylic or polyester resin, a partially hydrolysed polyvinyl acetal or a polyvinyl alcohol. This type of polycondensation of polysiloxanes is described, for example, in J. J. Lebrun, H. Pode, Comprehensive Polymer Science, Vol. 5, p. 593, Pergamon Press, Oxford, 1989. Other cationically polymerisable materials that are suitable for the preparation of surface coatings are ethylenically unsaturated compounds polymerisable by a cationic mechanism, such as vinyl ethers, for example methyl vinyl ether, isobutyl vinyl ether, trimethylolpropane trivinyl ether, ethylene glycol divinyl ether; cyclic vinyl ethers, for example 3,4-dihydro-2-formyl-2H-pyran (dimeric acrolein) or the 3,4-dihydro-2H-pyran-2-carboxylic acid ester of 2-hydroxymethyl-3,4-dihydro-2H-pyran; vinyl esters, such as vinyl acetate and vinyl stearate, mono- and di-olefins, such as α-methylstyrene, N-vinylpyrrolidone or N-viylcarbazole.

For certain purposes, resin mixtures having monomeric or oligomeric constituents containing polymerisable unsaturated groups are used. Such surface coatings can also be cured using compounds of formula Ia, Ib, Ic, IIa, IIb or IIc. In that process, radical polymerisation initiators or photoinitiators can additionally be used. The former initiate polymerisation of the unsaturated groups during heat treatment, the latter during UV Irradiation.

The invention also relates to a composition comprising
(a) a compound which cures upon the action of an acid or a compound whose solubility is increased upon the action of an acid; and
(b) as photosensitive acid donor, at least one compound of the formula Ia, Ib, IIc, IIa, IIb or tic as described above.

The compounds of formulae Ia, Ib, Ic, IIa, IIb or IIc respectively, are generally added to the compositions in an amount from 0.1 to 30% by weight, for example from 0.5 to 10% by weight, especially from 1 to 5% by weight.

According to the invention, the compounds of formula Ia, Ib, Ic, IIa, IIb or IIc can be used together with further photosensitive acid donor compounds (b1), further photoinitiators (d), sensitisers (e) and/or additives (c).

Suitable photosensitive acid donor compounds (b1), sensitizers (e) and addtives (c) are described above.

Examples of additional photoinitiators (d) are radical photoinitiators, such as those from the class of the benzophenones, acetophenone derivatives, such as a-hydroxycycloalkylphenyl ketone, dialkoxyacetophenone, a-hydroxy- or a-amino-acetophenone, 4-aroyl-1,3-dioxolans, benzoin alkyl ethers and benzil ketals, monoacylphosphine oxides, bisacylphosphine oxides or titanocenes. Examples of especially suitable additional photoinitiators are: 1-(4-dodecyl-benzoyl)-1-hydroxy-1-methyl-ethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methylethane, 1-[4-(acryloyloxyethoxy)-benzoyl]-1-hydroxy-1-methyl-ethane, diphenyl ketone, phenyl-1-hydroxycyclohexyl ketone, (4-morpholinobenzoyl)-1-benzyl-1-dimethylamino-propane, 1-(3,4-dimethoxyphenyl)-2-benzyl-2-dimethylamino-butan-1-one, (4-methylthiobenzoyl)-1-methyl-1-morpholino-ethane, benzil dimethyl ketal, bis (cyclopentadienyl)-bis(2,6-difluoro-3-pyrryl-phenyl) titanium, 2,4,6-trmethylbenzoyldiphenylphosphine oxide, bis(2,6-dimethoxybenzoyl)-(2,4,4-trimethyl-pentyl)-phosphine oxide, bis(2,4,6-trimethylbenzoyl)-2,4-dipentyloxyphenyl-phosphine oxide or bis(2,4,6-trimethylbenzoyl)phenyl-phosphine oxide. Further suitable additional photoinitiators are to be found in U.S. Pat. No. 4,950,581, column 20, line 35 to column 21, line 35. Other examples are trihalomethyltriazine derivatives or hexaarylbisimidazolyl compounds. Further examples for additional photoinitiators are borate compounds, as for example described in U.S. Pat. No. 4,772,530, EP 775706, GB 2307474, GB 2307473 and GB 2304472. The borate compounds preferably are used in combination with electron acceptor compounds, such as, for example dye cations, or thioxanthone derivatives.

Further examples of additional photoinitiators ate peroxide compounds, e.g. benzoyl peroxide (other suitable peroxides are described in U.S. Pat. No. 4,950,581, col. 19, 1.17–25) or cationic photoinitiators, such as aromatic sulfonium or iodonium salts, such as those to be found in U.S. Pat. No. 4,950,581, col. 18, 1.60 to col. 19, 1.10, or cyclopentadienyl-arene-iron(II) complex salts, for example ($\eta^6$-isopropylbenzene)($\eta^5$-cyclopentadienyl)-iron(II) hexafluorophosphate.

The surface coatings may be solutions or dispersions of the surface-coating resin in an organic solvent or in water, but they may also be solventless. Of special interest are surface coatings having a low solvent content, so-called "high solids surface coatings", and powder coating compositions. The surface coatings may be clear lacquers, as used, for example, in the automobile industry as finishing lacquers for multilayer coatings. They may also comprise pigments and/or fillers, which may be inorganic or organic compounds, and metal powders for metal effect finishes.

The surface coatings may also comprise relatively small amounts of special additives customary in surface-coating technology, for example flow improvers, thixotropic agents, leveling agents, antifoaming agents, wetting agents, adhesion promoters, light stabilisers, antioxidants, or sensitisers.

UV absorbers, such as those of the hydroxyphenyl-benzotriazole, hydroxyphenyl-benzophenone, oxalic acid amide or hydroxyphenyl-s-triazine type may be added to the compositions according to the invention as light stabilisers. Individual compounds or mixtures of those compounds can be used with or without the addition of sterically hindered amines (HALS).

Examples of such UV absorbers and light stabilisers are
1. 2-(2'-Hydroxyphenyl)-benzotriazoles, such as 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)phenyl)-benzotriazole, 2-(3',5'-di-t-butyl-2'-hydroxyphenyl)-5-chloro-benzotriazole, 2-(3'-tert-butyl-2'-hydroxy-5'-methylphenyl)-5-chloro-benzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis-(a,a-dimethylbenzyl)-2'-hydroxyphenyl)-benzotriazole, mixture of 2-(3'-tert-butyl-2'-hydroxy-5'-(2-octyloxycarbonylethyl)phenyl)-5-chloro-benzotriazole, 2-(3'-tert-butyl-5'-[2-(2-ethyl-hexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2(3'-tert-butyl-2'-hydroxy-5'-(2-methoxycarbonylethyl)phenyl)-benzotriazole, 2-(3'-tert-butyl-2'-hydroxy-5'-(2-octyloxycarbonylethyl)phenyl)-benzotriazole, 2-(3'-tert-butyl-5'-[2-(2-ethylhexyloxy)carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)phenyl-benzotriazole, 2,2'-methylene-bis[4-(1,1,3,3-tetramethylbutyl)-6-benzotriazol-2-yl-phenol]; transesterification product of 2-[3'-tert-butyl-5'-(2-methoxycarbonylethyl)-2'-hydroxyphenyl]-benzotriazole with polyethylene glycol 300; (R—CH$_2$CH$_2$—COO(CH$_2$)$_3$12-wherein R=3'-tert-butyl-4'-hydroxy-5'-2H-benzotriazol-2-yl-phenyl.
2. 2-Hydroxybenzophenones, such as the 4-hydroxy, 4-methoxy, 4-octyloxy, 4-decyloxy, 4-dodecyloxy, 4-benzyloxy, 4,2',4'-trihydroxy or 2'-hydroxy-4,4'-dimethoxy derivative.
3. Esters of unsubstituted or substituted benzoic acids, such as 4-tert-butyl-phenyl salicylate, phenyl salicylate, octylphenyl salicylate, dibenzoylresorcinol, bis(4-tert-butylbenzoyl)resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butylhydroxybenzoic acid octadecyl ester, 3,5-di-tert-butyl-4-hydroxybenzoic acid 2-methyl-4,6-di-tert-butylphenyl ester.
4. Acrylates, such as a-cyano-b,b-diphenylacrylic acid ethyl ester or isooctyl ester, a-carbo-methoxy-cinnamic acid methyl ester, a-cyano-b-methyl-p-methoxy-cinnamic acid methyl ester or butyl ester, a-carbomethoxy-p-methoxy-cinnamic acid methyl ester, N-(b-carbometh-oxy-b-cyanovinyl)-2-methyl-indoline.
5. Sterically hindered amines, such as bis(2,2,6,6-tetramethyl-piperidyl)sebacate, bis(2,2,6,6-tetramethyl-piperidyl)succinate, bis(1,2,2,6,6-pentamethylpiperidyl)sebacate, n-butyl-3,5-di-tert-butyl-4-hydroxybenzyl-malonic acid bis(1,2,2,6,6-pentamethylpiperidyl) ester, condensation product of 1-hydroxyethyl-2,2,6,6-tetramethyl-4-hydroxypiperidine and succinic acid, condensation product of N,N'-bis(2,2,6,6-tetramethyl-4-piperidyl)hexamethylenediamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1,2-ethanediyl)-bis(3,3,5,5-tetramethyl-piperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, condensation product of N,N'-bis(2,2,6,6-tetra-methyl-4-piperidyl)hexa-methylenediamine and 4-morpholino-2,6-dichloro-1,3,5-triazine, condensation product of 2-chloro-4,6-di(4-n-butylamino-2,2,6,6-tetramethylpiperidyl)-1,3,5-triazine and 1,2-bis(3-amino-propylamino)ethane, condensation product of 2-chloro-4,6-di(4-n-butylamino-1,2,2,6,6-pentamethylpipendyl)-1,3,5-triazine and 1,2-bis(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl) pyrrolidine-2,5-dione, 3-dodecyl-1-(1,2,2,6,6-pentamnethyl-4-piperidyl)-pyrrolidine-2,5-dione.
6. Oxalic acid diamides, such as 4,4'-dioctyloxy-oxanilide, 2,2'-diethoxy-oxanilide, 2,2'-di-octyloxy-5,5'-di-tert-butyl-oxanilide, 2,2'-didodecyloxy-5,5'-di-tert-butyl-oxanilide, 2-ethoxy-2-ethyl-oxanilide, N,N'-bis(3-dimethylaminopropyl)oxalamide, 2-ethoxy-5-tert-butyl-2'-ethyloxanilide and a mixture thereof with 2-ethoxy-2'-ethyl-5,4'-di-tert-butyl-oxanilide, mixtures of o- and p-methoxy- and of o- and p-ethoxy-di-substituted oxanilides.
7. 2-(2-Hydroxyohenyl)-1,3,5-trdazines, such as 2,4,6-tris(2-hydroxy-4-octyloxyphenyl)-1,3,5-triazine, 2-(2-hydroxy-4-octyloxyphenyl)-4,6-bis(2,4-dimethylphenyl)-

1,3,5-triazine, 2-(2,4-di-hydroxyphenyl)4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-[2-hydroxy-4-(2-hydroxy-3-butyloxy-propyloxy)phenyl]-4,6-bis(2,4-dimethyl-phenyl)-1,3,5-triazine, 2-[2-hydroxy-4-(2-hydroxy-3-octyloxy-propyloxy)phenyl]4,6-bis(2,4-dimethylphenyl)-1,3,5-triazine, 2-(4-dodecyl-/tridecyl-oxy-(2-hydroxypropyl)oxy-2-hydroxy-phenyl]-4,6-bis(2,4-dimethylphenyl)-1,3,5-triazine.

8. Phosphites and phosphonites, such as triphenyl phosphite, diphenyl alkyl phosphites, phenyl dialkyl phosphites, tris(nonylphenyl) phosphite, trilauryl phosphite, trioctadecyl phosphite, distearyl-pentaerythritol diphosphite, tris (2,4-di-tert-butylphenyl) phosphite, diisodecylpentaerythritol diphosphite, bis(2,4-di-tert-butylphenyl) pentaerythritol diphosphite, bis(2,6-di-tert-butyl-4-methylphenyl)pentaerythritol diphosphite, bis-isodecyloxy-pentaerythritol diphosphite, bis(2,4-di-tert-butyl-6-methylphenyl)pentaerythritol diphosphite, bis-(2,4,6-tri-tert-butylphenyl)pentaerythritol diphosphite, tristearyl-sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3,2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite, bis(2,4-di-tert-butyl-6-methylphenyl)ethyl phosphite.

Such light stabilisers can also be added, for example, to an adjacent surface-coating layer from which they gradually diffuse into the layer of stoving lacquer to be protected. The adjacent surface-coating layer may be a primer under the stoving lacquer or a finishing lacquer over the stoving lacquer.

It is also possible to add to the resin, for example, photosensitisers which shift or increase the spectral sensitivity so that the irradiation period can be reduced and/or other light sources can be used. Examples of photosensitisers are aromatic ketones or aromatic aldehydes (as described, for example, in U.S. Pat. No. 4,017,652), 3-acyl-coumarins (as described, for example, in U.S. Pat. No. 4,366,228, EP 738928, EP 22188), keto-coumarines (as described e.g. in U.S. Pat. No. 5,534,633, EP 538997, JP 8272095-A), styryl-coumarines (as described e.g. in EP 624580), 3-(aroylmethylene)-thiazolines, thioxanthones, condensed aromatic compounds, such as perylene, aromatic amines (as described, for example, in U.S. Pat. No. 4,069,954 or WO 96/41237) or cationic and basic colourants (as described, for example, in U.S. Pat. No. 4,026,705), for example eosine, rhodanine and erythrosine colourants, as well as dyes and pigments as described for example in JP 8320551-A, EP 747771, JP 7036179-A, EP 619520, JP 6161109-A, JP 6043641, JP 6035198-A, WO 93/15440, EP 568993, JP 5005005-A, JP 5027432-A, JP 5301910-A, JP 4014083-A, JP 4294148-A, EP 359431, EP 103294, U.S. Pat. No. 4,282,309, EP 39025, EP 5274, EP 727713, EP 726497 or DE 2027467.

Other customary additives are—depending on the intended use—optical brighteners, fillers, pigments, colourants, wetting agents or flow improvers and adhesion promoters For curing thick and pigmented coatings, the addition of micro glass beads or powdered glass fibres, as described in U.S. Pat. No. 5,013,768, is suitable.

Onium salts can also be used, for example, in hybrid systems. These systems are based on formulations that are fully cured by two different reaction mechanisms. Examples thereof are systems that comprise components that are capable of undergoing an acid-catalysed crosslinking reaction or polymerisation reaction, but that also comprise further components that crosslink by a second mechanism. Examples of the second mechanism are radical full cure, oxidative crosslinking or humidity-initiated crosslinking. The second curing mechanism may be initiated purely thermally, if necessary with a suitable catalyst, or also by means of light using a second photoinitiator. Suitable additional photoinitiators are described above.

If the composition comprises a radically crosslinkable component, the curing process, especially of compositions that are pigmented (for example with titanium dioxide), can also be assisted by the addition of a component that is radical-forming under thermal conditions, such as an azo compound, for example 2,2'-azobis(4-methoxy-2,4-dimethylvaleronitrile), a triazene, a diazosulfide, a pentazadiene or a peroxy compound, such as, for example, a hydroperoxide or peroxycarbonate, for example tert-butyl hydroperoxide, as described, for example, in EP 245639. The addition of redox initiators, such as cobalt salts, enables the curing to be assisted by oxidative crosslinking with oxygen from the air.

The surface coating can be applied by one of the methods customary in the art, for example by spraying, painting or immersion. When suitable surface coatings are used, electrical application, for example by anodic electrophoretic deposition, is also possible. After drying, the surface coating film is irradiated. If necessary, the surface coating film is then fully cured by means of heat treatment.

The compounds of formulae Ia, Ib, Ic, IIa, IIb or IIc can also be used for curing mouldings made from composites. A composite consists of a self-supporting matrix material, for example a glass fibre fabric, impregnated with the photo-curing formulation.

It is known from EP 592139 that onium salts can be used as acid generators, which can be activated by light in compositions that are suitable for the surface treatment and cleaning of glass, aluminium and steel surfaces. The use of such compounds in organosilane systems results in compositions that have significantly better storage stability than those obtained when the free acid is used. The compounds of formula Ia, Ib, Ic, IIa, IIb or IIc are also suitable for this application.

The onium salts of the present invention can also be used to shape polymers that undergo an acid induced transition into a state where they have the required properties using photolithography. For instance the onium salts can be used to pattern conjugated emissive polymers as described, for example, in M. L. Renak; C. Bazan; D. Roitman; Advanced materials 1997, 9, 392. Such patterend emissive polymers can be used to manufacture micro-scalar patterned Light Emitting Diodes (LED) which can be used to manufacture displays and data storage media. In a similar way precursors for polyimides (e.g. polyimid precursors with acid labile protecting groups that change solubility in the developer) can be irradiated to form patterned polyimide layers which can serve as protective coatings, insulating layers and buffer layers in the production of microchips and printed circuit boards.

The formulations of the invention may also be used as conformal coatings, photoimagable insulating layers and dielectrics as they are used in sequential build up systems for printed circuit boards, stress buffer layers and in the manufacturing of integrated circuits.

It is known that conjugated polymers like, e.g. polyanilines can be converted from semiconductive to conductive state by means of proton doping. The onium salts of the present invention can also be used to imagewise irradiate compositions comprising such conjugated polymers in order to form conducting structures (exposed areas) embedded in insulating material (non exposed areas). These materials can be used as wiring and connecting parts for the production of electric and electronic devices.

Suitable radiation sources for the compositions comprising compounds of formula Ia, Ib, Ic, Ia, IIb or IIc are radiation sources that emit radiation of a wavelength of approximately from 150 to 1500, for example from 180 to 1000, or preferably from 190 to 700 nanometers as well as e-beam radiation and high-energy electromagnetic radiation such as X-rays. Both, point sources and planlform projectors (lamp carpets) are suitable. Examples are: carbon arc lamps, xenon arc lamps, medium pressure, high pressure and low pressure mercury lamps, optionally doped with metal halides (metal halide lamps), microwave-excited metal vapour lamps, excimer lamps, superactinic fluorescent tubes, fluorescent lamps, argon filament lamps, electronic flash lamps, photographic flood lights, electron beams and X-ray beams generated by means of synchrotrons or laser plasma. The distance between the radiation source and the substrate according to the invention to be irradiated can vary, for example, from 2 cm to 150 cm, according to the intended use and the type and/or strength of the radiation source. Suitable radiaiton sources are especially mercury vapour lamps, especially medium and high pressure mercury lamps, from the radiation of which emission lines at other wavelengths can, if desired, be filtered out. That is especially the case for relatively short wavelength radiation. It is, however, also possible to use low energy lamps (for example fluorescent tubes) that are capable of emitting in the appropriate wavelength range. An example thereof is the Philips TL03 lamp. Another type of radiation source that can be used are the light emitting diodes (LED) that emit at different wavelengths throughout the whole spectrum either as small band emitting source or as broad band (white light) source. Also suitable are laser radiation sources, for example excimer lasers, such as Kr-F lasers for irradiation at 248 nm, Ar—F lasers at 193 nm, or $F_2$ laser at 157 nm. Lasers in the visible range and in the infrared range can also be used. Especially suitable is radiation of the mercury i, h and g lines at wavelengths of 365, 436 and 405 nanometers. A suitable laser-beam source is, for example, the argon-ion laser, which emits radiation at wavelengths of 454, 458, 466, 472, 478, 488 and 514 nanometers. Nd-YAG-lasers emitting light at 1064 nm and its second and third harmonic (532 nm and 355 nm respectively) can also be used. Also suitable is, for example, a helium/cadmium laser having an emission at 442 nm or lasers that emit in the UV range. With that type of irradiation, it is not absolutely essential to use a photomask in contact with the photopolymeric coating to produce a positive or negative resist; the controlled laser beam is capable of writing directly onto the coating. For that purpose the high sensitivity of the materials according to the invention is very advantageous, allowing high writing speeds at relatively low intensities. On irradiation, the onium salts in the composition in the irradiated sections of the surface coating decompose to form the acids.

In contrast to customary UV curing with high-intensity radiation, with the compounds according to the invention activation is achieved under the action of radiation of relatively low intensity. Such radiation includes, for example, daylight (sunlight), and radiation sources equivalent to daylight. Sunlight differs in spectral composition and intensity from the light of the artificial radiation sources customarily used in UV curing. The absorption characteristics of the compounds according to the invention are as well suitable for exploiting sunlight as a natural source of radiation for curing. Daylight-equivalent artificial light sources that can be used to activate the compounds according to the invention are to be understood as being projectors of low intensity, such as certain fluorescent lamps, for example the Philips TL05 special fluorescent lamp or the Philips TL09 special fluorescent lamp. Lamps having a high daylight content and daylight itself are especially capable of curing the surface of a surface-coating layer satisfactorily in a tack-free manner. In that case expensive curing apparatus is superfluous and the compositions can be used especially for exterior finishes. Curing with daylight or daylight-equivalent light sources is an energy-saving method and prevents emissions of volatile organic components in exterior applications. In contrast to the conveyor belt method, which is suitable for flat components, daylight curing can also be used for exterior finishes on static or fixed articles and structures.

The surface coating to be cured can be exposed directly to sunlight or daylight-equivalent light sources. The curing can, however, also take place behind a transparent layer (e.g. a pane of glass or a sheet of plastics).

The examples which follow illustrate the invention in more detail. Parts and percentages are, as in the remainder of the description and in the claims, by weight, unless stated otherwise. Where alkyl radicals having more than three carbon atoms are referred to without any mention of specific isomers, the n-isomers are meant in each case.

EXAMPLE 1

Diphenyliodonium Phenylsulfate 1.1: Diphenyliodonium Hydrogensulfate 55.5 ml (0.625 mol) of benzene and 53.5 g (0.25 mol) of potassium iodate are added to 50 ml of acetic anhydride and the reaction mixture is stirred while cooling by an ice-salt bath. To the suspension is added dropwise a cold solution of 35 ml of conc sulfuric acid and 50 ml of acetic anhydride with keeping the temperature below 5° C. for a period of 3 hours. The reaction mixture is stirred overnight and the temperature is gradually raised to room temperature during the course of the reaction. After the reaction mixture is cooled by an ice bath, 300 ml of diethyl ether are added and stirred for 1 hour at 0° C. and for additional 4 hours at room temperature. The precipitate is filtered off and washed with diethyl ether. The crude diphenyliodonium hydrogensulfate is obtained as a pale pink solid, and used in the next step without further purification.

1.2: Tetramethylammonium Phenylsulfate 25 g (0.266 mol) of phenol are dissolved in 100 ml of dimethylformamide (DMF), and 46.5 g (0.292 mol) of a pyridine/sulfur trioxide complex are added to the solution. The reaction mixture is stirred for 3 hours at 50° C. and for additional 15 hours at room temperature. 100 ml of 26% aqueous tetramethylammonium hydroxide (TMAH) solution are added to the mixture and stirred for 30 min at room temperature. After removing the solvent by a rotary evaporator, 50 ml of ethanol are added to the residue and stirred for 30 min at room temperature. The solid is filtered off and washed with ethanol. The crude tetramethylammonium phenylsulfate is obtained as a white solid, and used in the next step without further purification.

1.3: Diphenyliodonium Phenylsulfate 3 g of the crude diphenyliodonium hydrogensulfate are dissolved in 50 ml of water. To the solution is added a solution of 2.35 g of the crude tetramethylammonium phenylsulfate dissolved in 10 ml of water. The mixture is stirred for 7 hours at room temperature. The product is extracted with methylene chloride and the organic layer is washed with water, dried over $MgSO_4$, and concentrated. The residue is purified by recrystallization from 1,2-dichloroethane, yielding 1.29 g of diphenyliodonium phenylsulfate as a white solid, mp. 129–132° C. The structure is confirmed by the $^1$H-NMR spectrum ($CDCl_6$/DMSO-$d_6$). δ [ppm]: 7.08 (t, 1H), 7.22–7.30 (m, 4H), 7.42 (t, 4H), 7.58 (t, 2H), 7.92 (d, 4H).

EXAMPLE 2

Di(4-tert-butylphenyl)iodonium 4-tert-butylphenylsulfate 2.1: Ammonium 4-tert-butylphenylsulfate 25 g (0.166 mol) of 4-tert-butylphenol is dissolved in 50 ml of DMF, and 31.7 g (0.199 mol) of a pyridine/sulfur trioxide complex, dissolved in 100 ml of DMF, are added to the solution. The reaction mixture is stirred for 3 hours at 50° C. and for additional 15 hours at room temperature. 13 ml of ammonia solution are added to the mixture and stirred for 30 min at room temperature. The solvent is removed by a rotary evaporator, yielding crude ammonium 4-tert-butylphenylsulfate as a beige solid, which is used in the next step without further purification.

2.2: Di(4-tert-butylphenyl)iodonium 4-tert-butylphenylsulfate 10 g (74.5 mmol) of tert-butylbenzene and 8.6 g (40.2 mmol) of potassium iodate are added to 10 ml of acetic anhydride and stirred under cooling by an ice-salt bath. To the suspension a cold solution of 6 ml of conc. sulfuric acid and 10 ml of acetic anhydride is added dropwise while the temperature is kept below 5° C. over a period of 1 hour. The reaction mixture is stirred overnight and the temperature is gradually raised to room temperature during the course of the reaction. After the reaction mixture is cooled by an ice bath, 30 ml of water are added. To the solution are added 9.2 g of the crude ammonium 4-tert-butyiphenyl sulfate, dissolved in 20 ml of water, followed by the addition of 40 ml of ammonia solution to neutralize the mixture. After the mixture is stirred for 4 hours at room temperature, the product is extracted with methylene chloride and the organic layer is washed with water, dried over $MgSO_4$, and concentrated. The residue is purified by recrystallization from toluene/hexane, yielding 5.59 g of di(4-tert-butylphenyl) iodonium 4-tert-butylphenylsulfate as a white solid, mp. 159–163° C. The structure is confirmed by the $^1$H-NMR spectrum ($CDCl_3$). δ [ppm]: 1.25 (s, 9H), 1.28 (s, 18H), 7.19 (d, 2H), 7.26 (d, 2H), 7.41 (d, 4H), 7.84 (d, 4H).

EXAMPLE 3

Di(4-tert-amylphenyl)iodonium phenylsulfate 3.1: Di(4-tert-amylphenyl)iodonium hydrogensulfate 111.2 g (0.75 mol) of tert-amylbenzene and 86.7 g (0.405 mol) of potassium iodate are added to 86 ml of acetic anhydride and the reaction mixture is stirred under cooling with an ice-salt bath. To the suspension a cold solution of 60.3 ml of conc. sulfuric acid and 86 ml of acetic anhydride is added dropwise while keeping the temperature below 5° C. for 4 hours. The reaction mixture is stirred overnight and the temperature is gradually raised to room temperature during the course of the reaction. After the reaction mixture is cooled by an ice bath, 100 ml of water are added. The product is extracted with methylene chloride, and the organic layer is washed with water, dried over $MgSO_4$, and concentrated, yielding crude di(4-tert-amylphenyl)iodonium hydrogensulfate as a brown solid. The crude di(4-tert-amylphenyl)iodonium hydrogensulfate is used in the next step without further purification.

3.2: Di(4-tert-amylphenyl)iodonium phenylsulfate 3.9 g of crude tetramethylammonium phenylsulfate prepared according to the method of Example 1.2 are dissolved in 10 ml of water. To the solution 6.8 g of the crude di(4-tert-amylphenyl)iodonium hydrogensulfate, dissolved in 5 ml of methanol, are added. The mixture is stirred for 3 hours at room temperature. 10 ml of methylene chloride are added to the solution and stirred for additonal 2 hours at room temperature. The product is extracted with methylene chloride and the organic layer is washed with water, dried over $MgSO_4$, and concentrated. 200 ml of tert-butyl methyl ether are added to the residue, affording a white solid. After the suspension is stirred at 60° C. for 15 min, the precipitate is filtered off and washed with tert-butyl methyl ether, yielding 4.37 g of di(4-tert-amylphenyl)iodonium phenylsulfate as a white solid, mp. 122–125° C. The structure is confirmed by the $^1$H-NMR spectrum ($CDCl_3$). δ [ppm]: 0.64 (t, 6H), 1.23 (s, 12H), 1.61 (q, 4H), 7.07 (t, 1H), 7.21–7.29 (m, 4H), 7.34 (d, 4H), 7.82 (d, 4H).

EXAMPLE 4

Di(4-tert-amylphenyl)iodonium propylsulfate 4.1: Tetramethylammonium Propylsulfate 10 ml (0.134 mol) of 1-propanol are dissolved in 40 ml of DMF, and 23.4 g (0.147 mol) of a pyridine/sulfur trioxide complex are added to the solution. The reaction mixture is stirred for 3 hours at 50° C. and for additional 15 hours at room temperature. 51.5 g of 26% aqueous TMAH solution are added to the mixture which then is stirred for 30 min at room temperature. After removing the solvent by a rotary evaporator, 50 ml of acetone are added to the residue and stirred for 30 min at room temperature. The solid is filtered off and washed with acetone. The crude tetramethylammonium propylsulfate is obtained as a white solid, and used in the next step without further purification.

4.2: Di(4-tert-amylphenyl)iodonium propylsulfate 3.4 g of the crude tetramethylammonium propylsulfate are dissolved in 10 ml of water. To the solution are added 6.8 g of the crude di(4-tert-amylphenyl)iodonium hydrogensulfate prepared according to the method of example 3.1, dissolved in 5 ml of methanol. The mixture is stirred for 4 hours at room temperature. 10 ml of methylene chloride are added to the solution and stirred for additonal 2 hours at room temperature. The product is extracted with methylene chloride and the organic layer is washed with water, dried over $MgSO_4$, and concentrated. The residue is purified by flash chromatography on silica gel with methylene chloride, followed by methylene chloride and ethanol (95:5) as an eluent, yielding 3.86 g of di(4-tert-amylphenyl)iodonium propylsulfate as a brownish solid, mp. 48–53° C. The structure is confirmed by the $^1$H-NMR spectrum ($CDCl_3$). δ [ppm]: 0.65 (t, 6H), 0.88 (t, 3H), 1.24 (s, 12H), 1.56–1.66 (m, 6H), 3.89 (t, 2H), 7.37 (d, 4H), 7.88 (d, 4H).

EXAMPLE 5

Di(4-tert-amylphenyl)iodonium 4-tert-butylphenylsulfate 7.5 g of the crude ammonium 4-tert-butylphenylsulfate, prepared according to the method of example 2.1, are dissolved in 10 ml of water. 15.6 g of the crude di(4-tert-amylphenyl)iodonium hydrogensulfate (according to example 3.1), dissolved in 5 ml of methanol, are added to the solution. The mixture is stirred for 2 hours at room temperature. 10 ml of methylene chloride are added to the solution and stirred for additonal 2 hours at room temperature. The product is extracted with methylene chloride and the organic layer is washed with water, dried over $MgSO_4$, and concentrated. The residue is purified by recrystallization from cyclohexane, yielding 6.96 g of di(4-tert-amylphenyl) iodonium 4-tert-butylphenylsulfate as a white solid, mp. 129–133° C. The structure is confirmed by the $^1$H-NMR spectrum ($CDCl_3$). δ [ppm]: 0.65 (t, 6H), 1.24 (m, 21H), 1.62 (q, 4H), 7.21 (d, 2H), 7.27 (d, 2H), 7.37 (d, 4H), 7.83 (d, 4H).

EXAMPLE 6

Bis[di(4-tert-amylphenyl)iodonium]para-phenylenedisulfate 6.1: Bis(tetramethylammonium) para-phenylenedisulfate 15 g (136 mmol) of para-hydroquinone are dissolved in 143 ml of DMF, and 47.7 g (300 mmol) of a pyridine/sulfur trioxide complex are added to the solution. The reaction mixture is stirred for 3 hours at 50° C. and for additional 15 hours at room temperature. 105 g of 26% aqueous TMAH solution are added to the mixture and stirred for 30 min at room temperature. After the solvent is removed by a rotary evaporator, 100 ml of ethanol are added to the residue and stirred for 30 min at room temperature. The solid is filtered off and washed with ethanol. The crude bis (tetramethylammonium) para-phenylenedisulfate is obtained as a white solid, and is used in the next step without further purification.

6.2: Bis[di(4-tert-amylphenyl)iodonium]para-phenylenedisulfate 1.9 g of the crude bis(tetramethylammonium) para-phenylenedisulfate are dissolved in 10 ml of water. 3.4 g of the crude di(4-tert-amylphenyl)iodonium hydrogensulfate (obtained according to example 3.1), dissolved in 2 ml of methanol, are added to the solution. The mixture is stirred for 1 hour at room temperature. 10 ml of methylene chloride are added to the solution and stirred for additonal 3 hours at room temperature. The product is extracted with methylene chloride and the organic layer is washed with water, dried over $MgSO_4$, and concentrated. The residue is purified by recrystallization from toluene, yielding 1.92 g of bis[di(4-tert-amylphenyl)iodonium]para-phenylenedisulfate as a white solid, mp. 111–115° C. The structure is confirmed by the $^1$H-NMR spectrum ($CDCl_3$). δ [ppm]: 0.63 (t, 12H), 1.23 (s, 24H), 1.60 (q, 8H), 7.18 (s, 4H), 7.36 (d, 8H), 7.82 (d, 8H).

EXAMPLE 7

(4-Methylphenyl)(4'-isobutylphenyl)iodonium phenylsulfate 7.1: (4-Methylphenyl)(4'-isobutylphenyl)iodonium hydrogensulfate 11.9 g (54.8 mmol) of 4-iodotoluene and 9.2 g (68.5 mmol) of isobutylbenzene are added dropwise to a solution of 35 ml of conc. sulfuric acid and 22 ml of water under cooling by an ice bath. 25 g of ammonium peroxodisulfate are added by portions to the solution under cooling by an ice-salt bath, keeping the temperature below 0° C. for 1 hour. The reaction mixture is stirred overnight and the temperature is gradually raised to room temperature during the course of the reaction. After cooling the reaction mixture by ice an bath, 118 ml of water are added. The product is extracted with methylene chloride, and the organic layer is washed with water, dried over $MgSO_4$, and concentrated, yielding (4-methylphenyl)(4'-isobutylphenyl)iodonium hydrogensulfate as a brown solid. The crude (4-methylphenyl)(4'-isobutylphenyl)iodonium hydrogensulfate is used in the next step without further purification.

7.2: (4-Methylphenyl)(4'-isobutylphenyl)iodonium phenylsulfate 0.98 g of the crude tetramethylammonium phenylsulfate, prepared according to the method of Example 1.2, are dissolved in 10 ml of water. 1.48 g of the crude (4-methylphenyl)(4'-isobutylphenyl)iodonium hydrogensulfate, dissolved in 10 ml of methanol, are added to the solution. The mixture is stirred for 1 hour at room temperature. 10 ml of methylene chloride are added to the solution and stirred for additional 3 hours at room temperature. The product is extracted with methylene chloride and the organic layer is washed with water, dried over $MgSO_4$, and concentrated. The residue is purified by flash chromatography on silica gel with methylene chloride, followed by methylene chloride and ethanol (95:5) as an eluent, yielding 1.54 g of (4-methylphenyl)(4'-isobutylphenyl)iodonium phenylsulfate as a pale yellow resin. The structure is confirmed by the $^1$H-NMR spectrum ($CDCl_3$). δ [ppm]: 0.87 (d, 6H), 1.78–1.87 (m, 11H), 2.37 (s, 3H), 2.47 (d, 2H), 7.08 (t, 1H), 7.13–7.31 (m, 8H), 7.77 (d, 4H).

EXAMPLE 8

(4-Methylphenyl)(4'-isobutylphenyl)iodonium 4-fluorophenylsulfate 8.1: Tetramethylammonium 4-fluorophenylsulfate 10 g (89 mmol) of 4-fluorophenol are dissolved in 47 ml of DMF, and 15.6 g (98 mmol) of a pyridine/sulfur trioxide complex are added to the solution. The reaction mixture is stirred for 3 hours at 50° C. and for additional 15 hours at room temperature. 34.4 g of 26% aqueous TMAH solution are added to the mixture and stirred for 30 min at room temperature. After removing the solvent by a rotary evaporator, 50 ml of ethanol are added to the residue and stirred for 30 min at room temperature. The solid is filtered off and washed with ethanol. The crude tetramethylammonium 4-fluorophenylsulfate is obtained as a beige solid, and used in the next step without further purification.

8.2: (4-Methylphenyl)(4'-isobutylphenyl)iodonium 4-fluorophenylsulfate 1.05 g of the crude tetramethylammonium 4-fluorophenylsulfate are dissolved in 10 ml of water. 1.48 g of the crude (4-methylphenyl)(4'-isobutylphenyl) iodonium hydrogensulfate (obtained according to example 7.1), dissolved in 10 ml of methanol, are added to the solution. The mixture is stirred for 1 hour at room temperature. 10 ml of methylene chloride are added to the solution and stirred for additonal 3 hours at room temperature. The product is extracted with methylene chloride and the organic layer is washed with water, dried over $MgSO_4$, and concentrated. The residue is purified by flash chromatography on silica gel with methylene chloride, followed by methylene chloride and ethanol (95:5) as an eluent, yielding 1.46 g of (4-methylphenyl)(4'-isobutylphenyl)iodonium 4-fluorophenylsulfate as a brown resin. The structure is confirmed by the $^1$H-NMR spectrum ($CDCl_3$). δ [ppm]: 0.87 (d, 6H), 1.79–1.86 (m, 1H), 2.38 (s, 3H), 2.47 (d, 2H), 6.87 (t, 2H), 7.13–7.22 (m, 6H), 7.78 (d, 4H).

EXAMPLE 9

(4-Methylphenyl)(4'-isobutylphenyl)iodonium phenylmethylsulfate 9.1: Tetramethylammonium Phenylmethylsulfate 10 g (92.5 mmol) of benzylalcohol are dissolved in 50 ml of DMF, and 16.2 g (102 mmol) of a pyridine/sulfur trioxide complex are added to the solution. The reaction mixture is stirred for 3 hours at 50° C. and for additional 15 hours at room temperature. 35.8 g of 26% aqueous TMAH solution are added to the mixture and stirred for 30 min at room temperature. After removing the solvent by a rotary evaporator, 200 ml of acetone are added to the residue and stirred for 30 min at room temperature. The solid is filtered off and washed with acetone. The crude tetramethylammonium phenylmethylsulfate is obtained as a white solid, and used in the next step without further purification.

9.2: (4-Methylphenyl)(4'-isobutylphenyl)iodonium phenylmethylsulfate 1.03 g of the crude tetramethylammonium phenylmethylsulfate are dissolved in 10 ml of water. 1.48 g of the crude (4-methylphenyl)(4'-isobutylphenyl)iodonium hydrogensulfate (obtained according to example 7.1), dissolved in 10 ml of methanol, are added to the solution. The mixture is stirred for 1 hour at room temperature. 10 ml of methylene chloride are added to the solution and stirred for additonal 3 hours at room temperature. The product is extracted with methylene chloride and the organic layer is washed with water, dried over MgSO$_4$, and concentrated. The residue is purified by flash chromatography on silica gel with methylene chloride, followed by methylene chloride and ethanol (95:5) as an eluent, yielding 1.31 g of (4-methylphenyl)(4'-isobutylphenyl)iodonium phenylmethylsulfate as a pale brown resin. The structure is confirmed by the $^1$H-NMR spectrum (CDCl$_3$). δ [ppm]: 0.86 (d, 6H), 1.80–1.85 (m, 1H), 2.36 (s, 3H), 2.45 (d, 2H), 4.97 (s, 2H), 7.12–7.37 (m, 9H), 7.77–7.81 (m, 4H).

EXAMPLE 10

Bis[(4-methylphenyl)(4'-isobutylphenyl)iodonium] para-phenylenedisulfate 0.69 g of crude bis(tetramethylammonium) para-phenylenedisulfate are dissolved in 10 ml of water. 1.48 g of crude (4-methylphenyl)(4'-isobutylphenyl)iodonium hydrogensulfate (obtained according to example 7.1), dissolved in 10 ml of methanol, are added to the solution. The mixture is stirred for 1 hour at room temperature. 10 ml of methylene chloride are added to the solution and stirred for additonal 3 hours at room temperature. The product is extracted with methylene chloride and the organic layer is washed with water, dried over MgSO$_4$, and concentrated. The residue is purified by flash chromatography on silica gel with methylene chloride, followed by methylene chloride and ethanol (95:5) as an eluent, yielding 1.06 g of bis[(4-methylphenyl)(4'-isobutylphenyl)iodonium]para-phenylenedisulfate as a white solid. The structure is confirmed by the $^1$H-NMR spectrum (CDCl$_3$). δ [ppm]: 0.85 (d, 12H), 1.74–1.85 (m, 2H), 2.34 (d, 6H), 2.43 (d, 4H), 7.12–7.19 (m, 12H), 7.77–7.82 (m, 8H).

EXAMPLE 11

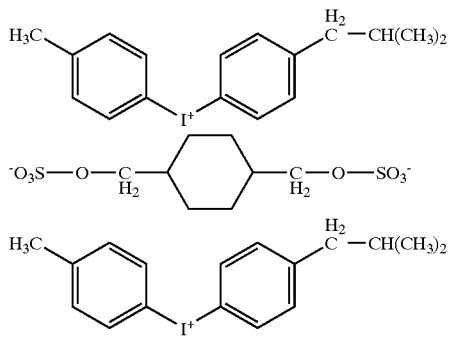

11.1: Diammonium Cyclohexane-1,4-di(methylenesulfate)

10 g (69.3 mmol) of 1,4-cyclohexanedimethanol are dissolved in 73 ml of DMF, and 24.3 g (152.6 mmol) of a pyridine/sulfur trioxide complex are added to the solution. The reaction mixture is stirred for 3 hours at 50° C. and for additional 15 hours at room temperature. 53.5 g of 26% aqueous TMAH solution are added to the mixture and stirred for 30 min at room temperature. After removing the solvent by a rotary evaporator, 50 ml of ethanol are added to the residue and stirred for 30 min at room temperature. The solid is filtered off and washed with ethanol. The crude product is obtained as a white solid, and used in the next step without further purification.

11.2: Bis[(4-methylphenyl)(4'-isobutylphenyl)iodonium] cyclohexane-1,4-di(methylenesulfate)

0.74 g of the crude compound obtained as described in Example 11.1 are dissolved in 10 ml of water. 1.48 g of crude (4-methylphenyl)(4'-isobutylphenyl)iodonium hydrogensulfate (obtained according to example 7.1), dissolved in 10 ml of methanol, are added to the solution. The mixture is stirred for 1 hour at room temperature. 10 ml of methylene chloride are added to the solution and stirred for additonal 3 hours at room temperature. The product is extracted with methylene chloride and the organic layer is washed with water, dried over MgSO$_4$, and concentrated. The residue is purified by flash chromatography on silica gel with methylene chloride, followed by methylene chloride and ethanol (2:1) as an eluent, yielding the product as a pale brown solid, mp. 81–85° C. The structure is confirmed by the $^1$H-NMR spectrum (CDCl$_3$). δ [ppm]: 0.87 (d, 12H), 1.35–1.90 (m, 10H), 2.38 (s, 6H), 2.47 (d, 4H), 3.70/3.82 (d, 4H), 7.16–7.24 (m, 8H), 7.82–7.88 (m, 8H).

EXAMPLE 12

Triphenylsulfonium 4-tert-butylphenylsulfate 1.0 g of triphenylsulfonium tetrafluoroborate is dissolved in 50 ml of water at 80° C. To this solution a solution of 0.8,5 g of crude ammonium 4-tert-butylphenylsulfate (prepared as described in Example 2.1) in 10 ml of water is added and stirred at 80° C. for 1 hour. The product is extracted with methylene chloride and the organic layer is washed with 2.5% ammonia solution and water, dried over MgSO$_4$, and concentrated. The residue is purified by recrystallization from ethyl acetate, yielding 0.72 g of triphenylsulfonium 4-tert-butylphenylsulfate as a white solid, mp. 129–132° C. The structure is confirmed by the $^1$H-NMR spectrum (CDCl$_3$). δ [ppm]: 1.24 (s, 9H), 7.21 (d, 2H), 7.28 (d, 2H), 7.60–7.79 (m, 15H).

EXAMPLES 13–53

The compounds of examples 13 to 53 are obtained according to the method described in example 1.3, using the corresponding educts. The structures and physical data are listed in table 1.

TABLE 1

| Ex. | Structure | Purification | State/mp(° C.)/ ¹H-NMR [δ(ppm)] |
|---|---|---|---|
| 13 | [H5C2-C(CH3)2-C6H4-I]+2 ; tetrahydropyran-2-yl-CH2-O-SO3⁻ | chromatography (CH2Cl2, followed by CH2Cl2:ethanol = 95:5) | pale yellow resin, 0.66 (t, 6H), 1.20–1.66 (m, 22H), 3.28–3.37 (m, 1H), 3.57–3.75 (m, 2H), 4.00 (d, 2H), 7.39 (d, 4H), 7.87 (d, 4H) |
| 14 | [H5C2-C(CH3)2-C6H4-I]+2 ; H5C2-C(=O)-CH2-O-SO3⁻ | chromatography (CH2Cl2, followed by CH2Cl2:ethanol = 95:5) | yellow resin, 0.67 (t, 6H), 1.23–1.27 (m, 15H), 1.64 (q, 4H), 4.17 (q, 2H), 4.62 (s, 2H), 7.43 (d, 4H), 7.86 (d, 4H) |
| 15 | [H5C2-C(CH3)2-C6H4-I]+2 ; diacetone-galactose-CH2-O-SO3⁻ | chromatography (CH2Cl2, followed by CH2Cl2:ethanol = 95:5) | pale yellow solid, 45–51° C. 0.66 (t, 6H), 1.16 (s, 3H), 1.22–1.30 (m, 15H), 1.42 (s, 3H), 1.45 (s, 3H), 1.63 (q, 4H), 4.21–4.32 (m, 5H), 4.57 (d, 1H), 5.41 (d, 1H), 7.41 (d, 4H), 7.87 (d, 4H) |
| 16 | [H5C2-C(CH3)2-C6H4-I]+2 ; menthyl-OSO3⁻ | recrystallization from mixture of tert-butyl methyl ether and hexane | white solid, 162–164° C. 0.66 (t, 6H), 0.77 (d, 3H), 0.78–0.87 (m, 7H), 0.92–1.10 (m, 2H), 1.20–1.42 (m, 14H), 1.57–1.70 (m, 6H), 2.23–2.35 (m, 1H), 2.40–2.47 (m, 1H), 4.10–4.19 (m, 1H), 7.40 (d, 4H), 7.85 (d, 4H) |
| 17 | [H5C2-C(CH3)2-C6H4-I]+2 ; PhCH2-O-SO3⁻ | recrystallization from mixture of tert-butyl methyl ether and hexane | white solid, 151–153° C. 0.63 (t, 6H), 1.23 (s, 12H), 1.60 (q, 4H), 4.97 (s, 2H), 7.23–7.39 (m, 9H), 7.84 (d, 4H) |

TABLE 1-continued

| Ex. | Structure | Purification | State/mp(° C.)/ $^1$H-NMR [δ(ppm)] |
|---|---|---|---|
| 18 | [H$_5$C$_2$-C(CH$_3$)$_2$-C$_6$H$_4$-I]$_2^+$  cyclohexyl-O-SO$_3^-$ | chromatography (CH$_2$Cl$_2$, followed by CH$_2$Cl$_2$:ethanol = 95:5) | pale yellow resin, 0.66 (t, 6H), 1.10–1.42 (m, 18H), 1.55–1.70 (m, 6H), 1.88–1.98 (m, 2H), 4.25–4.29 (m, 1H), 7.38 (d, 4H), 7.89 (d, 4H). |
| 19 | [H$_5$C$_2$-C(CH$_3$)$_2$-C$_6$H$_4$-I]$_2^+$  naphthalen-1-yl-O-SO$_3^-$ | chromatography (CH$_2$Cl$_2$, followed by CH$_2$Cl$_2$:ethanol = 95:5) | orange resin, 0.62 (t, 6H), 1.23 (s, 12H), 1.58 (q, 4H), 7.23–7.27 (m, 4H), 7.35–7.45 (m, 3H), 7.57–7.66 (m, 6H), 7.72–7.78 (m, 1H), 7.37–7.42 (m, 1H). |
| 20 | [H$_5$C$_2$-C(CH$_3$)$_2$-C$_6$H$_4$-I]$_2^+$  2-O$_2$N-C$_6$H$_4$-CH$_2$-O-SO$_3^-$ | recrystallization from mixture of tert-butyl methyl ether and toluene | white solid, 155–156° C., 0.65 (t, 6H), 1.25 (s, 12H), 1.62 (q, 4H), 5.44 (s, 2H), 7.40 (d, 5H), 7.63 (t, 1H), 7.85 (d, 4H), 7.95 (d, 1H), 8.04 (d, 1H). |
| 21 | [H$_5$C$_2$-C(CH$_3$)$_2$-C$_6$H$_4$-I]$_2^+$  H$_5$C$_2$-C(CH$_3$)$_2$-C$_6$H$_4$-O-SO$_3^-$ | recrystallization from tert-butyl methyl ether | white solid, 111–119° C., 0.60–0.67 (m, 9H), 1.19 (s, 6H), 1.23 (s, 12H), 1.53–1.67 (m, 6H), 7.18–7.25 (m, 4H), 7.37 (d, 4H), 7.81 (d, 4H). |
| 22 | [H$_5$C$_2$-C(CH$_3$)$_2$-C$_6$H$_4$-I]$_2^+$  CH$_3$O-C$_6$H$_4$-O-SO$_3^-$ | recrystallization from mixture of tert-butyl methyl ether and toluene | white solid, 120–121° C., 0.65 (t, 6H), 1.25 (s, 12H), 1.62 (q, 4H), 6.77 (d, 2H), 7.22 (d, 2H), 7.36 (d, 4H), 7.80 (d, 4H). |

TABLE 1-continued

| Ex. | Structure | Purification | State/mp(° C.)/ $^1$H-NMR [δ(ppm)] |
|---|---|---|---|
| 23 | 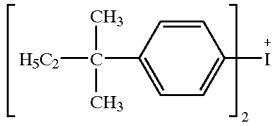 | recrystallization from mixture of tert-butyl methyl ether and toluene | white solid, 135–137° C., 0.65 (t, 6H), 1.25 (s, 12H), 1.62 (q, 4H), 2.25 (s, 3H), 7.03 (d, 2H), 7.20 (d, 2H), 7.36 (d, 4H), 7.80 (d, 4H). |
| 24 | 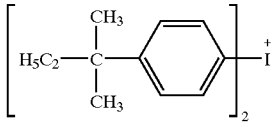 | chromatography (CH$_2$Cl$_2$, followed by CH$_2$Cl$_2$:ethanol = 95:5) | pale yellow solid, 130–134° C., 0.65 (t, 6H), 1.25 (s, 12H), 1.62 (q, 4H), 4.14 (q, 2H), 7.40 (d, 4H), 7.90 (d, 4H). |
| 25 | 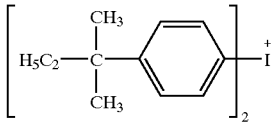 | chromatography (CH$_2$Cl$_2$, followed by CH$_2$Cl$_2$:ethanol = 95:5) | yellow resin, 0.65 (t, 6H), 1.25 (s, 12H), 1.62 (q, 4H), 6.49 (s, 1H), 7.17–7.35 (m, 10H), 7.44 (d, 4H), 7.68 (d, 4H). |
| 26 | 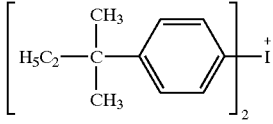 | chromatography (CH$_2$Cl$_2$, followed by CH$_2$Cl$_2$:ethanol = 95:5) | pale yellow resin, 0.65 (t, 6H), 1.24 (s, 12H), 1.55 (d, 3H), 1.61 (q, 4H), 5.46 (q, 1H), 7.19 (t, 1H), 7.27 (t, 2H), 7.32 (d, 4H), 7.43 (d, 2H), 7.75 (d, 4H). |
| 27 | 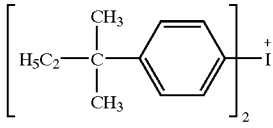 | chromatography (CH$_2$Cl$_2$, followed by CH$_2$Cl$_2$:ethanol = 95:5) | pale yellow resin, 0.65 (t, 6H), 1.23 (s, 12H), 1.61 (q, 4H), 6.67 (s, 1H), 7.21–7.38 (m, 12H), 7.82 (d, 4H), 8.00 (d, 2H). |

| Ex. | Structure | Purification | State/mp(° C.)/ ¹H-NMR [δ(ppm)] |
|---|---|---|---|
| 28 | [H₅C₂-C(CH₃)(CH₃)-C₆H₄-I]₂⁺  C₂H₅-C₆H₄-O-SO₃⁻ | chromatography (CH₂Cl₂, followed by CH₂Cl₂:ethanol = 95:5) | yellow resin, 0.65 (t, 6H), 1.15 (t, 3H), 1.25 (s, 12H), 1.62 (q, 4H), 2.55 (q, 2H), 7.07 (d, 2H), 7.23 (d, 2H), 7.37 (d, 4H), 7.80 (d, 4H). |
| 29 | [H₅C₂-C(CH₃)(CH₃)-C₆H₄-I]₂⁺  (CH₃)₂CH-C₆H₄-O-SO₃⁻ | recrystallization from mixture of tert butyl methyl ester and toluene | white solid, 113–116° C., 0.65 (t, 6H), 1.16 (d, 6H), 1.24 (s, 12H), 1.61 (q, 4H), 2.78–2.87 (m, 1H), 7.09 (d, 2H), 7.22 (d, 2H), 7.36 (d, 4H), 7.82 (d, 4H). |
| 30 | [H₃C-C(CH₃)(CH₃)-C₆H₄-I]₂⁺  H₅C₂-C(CH₃)(CH₃)-C₆H₄-O-SO₃⁻ | chromatography (CH₂Cl₂, followed by CH₂Cl₂:ethanol = 95:5) | yellow resin, 0.64 (t, 3H), 1.20 (s, 6H), 1.27 (s, 18H), 1.56 (q, 2H), 7.20 (s, 4H), 7.41 (d, 4H), 7.83 (d, 4H). |
| 31 | [H₃C-C(CH₃)(CH₃)-C₆H₄-I]₂⁺  C₆H₅-CH₂-O-SO₃⁻ | recrystallization from tert-butyl methyl ester | white solid, 161–164° C., 1.27 (s, 18H), 5.76 (s, 2H), 7.22–7.43 (m, 9H), 7.83 (d, 4H). |
| 32 | [H₃C-C(CH₃)(CH₃)-C₆H₄-I]₂⁺  menthyl-O-SO₃⁻ | recrystallization from mixture of tert-butyl methyl ether and toluene | white solid, 184–185° C., 0.72–1.02 (m, 12H), 1.12–1.37 (m, 20H), 1.55–1.62 (m, 2H), 2.20–2.28 (m, 1H), 2.32–2.42 (m, 1H), 4.03–4.10 (m, 1H), 7.44 (d, 4H), 7.88 (d, 4H). |

TABLE 1-continued

| Ex. | Structure | Purification | State/mp(° C.)/ ¹H-NMR [δ(ppm)] |
|---|---|---|---|
| 33 | 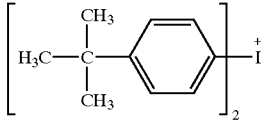 | recrystallization from mixture of tert butyl methyl ether and $CH_2Cl_2$ | white solid, 167–168° C., 1.28 (s, 18H), 2.30 (s, 3H), 4.97 (s, 2H), 7.09 (d, 2H), 7.28 (d, 2H), 7.40 (d, 4H), 7.82 (d, 4H). |
| 34 | 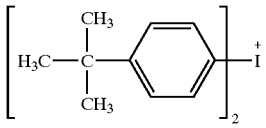 | chromatography ($CH_2Cl_2$, followed by $CH_2Cl_2$:ethanol = 95:5) | white solid, 93–105° C. 1.17 (s, 3H), 1.28–1.32 (m, 21H), 1.42 (s, 3H), 1.49 (s, 3H), 4.16–4.32 (m, 5H), 4.57 (d, 1H), 5.23 (d, 1H), 7.44 (d, 4H), 7.89 (d, 4H). |
| 35 | 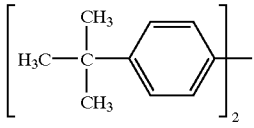 | recrystallization from mixture of tert-butyl methyl ethyl and toluene | white solid, 176–181° C., 1.27 (s, 18H), 2.30 (s, 3H), 4.99 (s, 2H), 7.09–7.20 (m, 3H), 7.35–7.41 (m, 5H), 7.83 (d, 4H). |
| 36 | 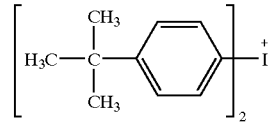 | recrystallization from mixture of tert-butyl methyl ether and toluene | white solid, 158–160° C., 1.27 (s, 18H), 2.29 (s, 3H), 4.94 (s, 2H), 7.03–7.23 (m, 4H), 7.38 (d, 4H), 7.84 (d, 4H). |
| 37 | 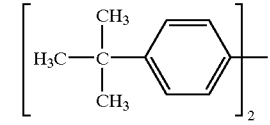 | recrystallization from mixture of tert-butyl methyl ether and toluene | white solid, 181–183° C., 1.22 (s, 18H), 5.43 (s, 2H), 7.28 (d, 4H), 7.37–7.57 (m, 4H), 7.70 (d, 4H), 7.79 (t, 2H), 8.26 (d, 1H). |

TABLE 1-continued

| Ex. | Structure | Purification | State/mp(° C.)/ $^1$H-NMR [δ(ppm)] |
|---|---|---|---|
| 38 | [structure: bis(4-tert-butylphenyl)iodonium with 9-anthracenylmethyl sulfonate] | recrystallization from mixture of hexane and toluene | white solid, 168–169° C., 1.19 (s, 18H), 6.06 (s, 2H), 7.21 (d, 4H), 7.44 (t, 2H), 7.52 (t, 2H), 7.56 (d, 4H), 7.97 (d, 2H), 8.43 (s, 1H), 8.59 (d, 2H). |
| 39 | [structure: bis(4-tert-butylphenyl)iodonium with 3,4-methylenedioxybenzyl sulfonate] | recrystallization from mixture of tert-butyl methyl ether and toluene | white solid, 151–152° C., 1.28 (s, 18H), 4.87 (s, 2H), 5.91 (s, 2H), 6.72 (d, 1H), 6.82 (d, 1H), 6.88 (s, 1H), 7.41 (d, 4H), 7.83 (d, 4H). |
| 40 | [structure: bis(4-tert-butylphenyl)iodonium with 2-thienylmethyl sulfonate] | recrystallization from tert-butyl methyl ether | white solid, 139–142° C., 1.28 (s, 18H), 5.11 (s, 2H), 6.91–6.94 (m, 1H), 7.05 (s, 1H), 7.24 (d, 1H), 7.41 (d, 4H), 7.86 (d, 4H). |
| 41 | [structure: bis(4-tert-butylphenyl)iodonium with 1-naphthyl sulfonate] | recrystallization from toluene | white solid, 158–162° C., 1.24 (s, 18H), 7.30 (d, 4H), 7.35–7.46 (m, 3H), 7.57–7.65 (m, 6H), 7.75–7.79 (m, 1H), 8.34–8.38 (m, 1H). |
| 42 | [structure: bis(4-tert-butylphenyl)iodonium with cyclohexyl sulfonate] | recrystallization from toluene | white solid, 189–190° C., 1.10–1.49 (m, 24H), 1.62–1.70 (m, 2H), 1.87–1.96 (m, 2H), 4.17–4.28 (m, 1H), 7.43 (d, 4H), 7.90 (d, 4H). |

TABLE 1-continued

| Ex. | Structure | Purification | State/mp(° C.)/ $^1$H-NMR [δ(ppm)] |
|---|---|---|---|
| 43 | 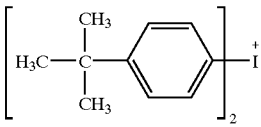 | recrystallization from mixture of tert-butyl methyl ether and toluene | white solid, 150–153° C., 1.28 (s, 18H), 1.35 (t, 3H), 3.91 (q, 2H), 6.76 (d, 2H), 7.21 (d, 2H), 7.41 (d, 4H), 7.81 (d, 4H). |
| 44 | 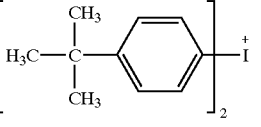 | recrystallization from tert-butyl methyl ether | white solid, 109–111° C., 1.26–1.34 (m, 21H), 4.06 (q, 2H), 6.82–6.91 (m, 2H), 7.01 (t, 1H), 7.40 (d, 4H), 7.57 (d, 1H), 7.84 (m, 4H). |
| 45 | 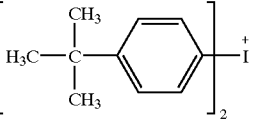 | recrystallization from mixture of tert-butyl methyl ether and toluene | white solid, 199–200° C., 0.85–0.95 (m, 2H), 1.09–1.33 (m, 21H), 1.55–1.76 (m, 6H), 3.72 (d, 2H), 7.43 (d, 4H), 7.89 (d, 4H). |
| 46 | 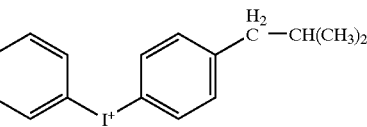 | recrystallization from toluene | white solid, 141–144° C., 0.88 (d, 6H), 1.24 (s, 9H), 1.80–1.88 (m, 1H), 2.48 (d, 2H), 7.15–7.27 (m, 6H), 7.38 (t, 2H), 7.55 (t, 1H), 7.80 (d, 2H), 7.90 (d, 2H). |
| 47 | 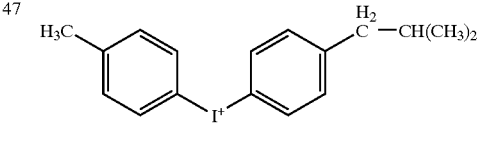 | recrystallization from toluene | white solid, 191–192° C., 0.72 (d, 3H), 0.75–1.00 (m, 15H), 1.15–1.23 (m, 1H), 1.27–1.37 (m, 1H), 1.54–1.63 (m, 2H), 1.78–1.90 (m, 1H), 2.12–2.23 (m, 1H), 2.28–2.38 (m, 1H), 2.39 (s, 3H), 2.48 (d, 2H), 4.01–4.09 (m, 1H), 7.17 (d, 2H), 7.22 (d, 2H), 7.82–7.88 (m, 4H). |

TABLE 1-continued

| Ex. | Structure | Purification | State/mp(° C.)/ ¹H-NMR [δ(ppm)] |
|---|---|---|---|
| 48 | (structure) | chromatography (CH$_2$Cl$_2$, followed by CH$_2$Cl$_2$:ethanol = 95:5) | yellow resin, 0.86 (d, 6H), 1.20 (s, 9H), 1.76–1.86 (m, 1H), 2.36 (s, 3H), 2.46 (d, 2H), 7.12–7.27 (m, 8H), 7.79 (d, 4H). |
| 49 | (structure) | chromatography (CH$_2$Cl$_2$, followed by CH$_2$Cl$_2$:ethanol = 95:5) | brown resin, 0.87 (d, 6H), 1.76–1.86 (m, 1H), 2.37 (s, 3H), 2.46 (d, 2H), 3.72 (s, 3H), 6.76 (d, 2H), 7.12–7.20 (m, 6H), 7.79 (d, 4H). |
| 50 | (structure) | chromatography (CH$_2$Cl$_2$, followed by CH$_2$Cl$_2$:ethanol = 95:5) | pale yellow resin, 0.87 (d, 6H), 1.79–1.86 (m, 1H), 2.38 (s, 3H), 2.47 (d, 2H), 5.37 (s, 2H), 7.18–7.24 (m, 4H), 7.40 (t, 1H), 7.62 (t, 1H), 7.83 (d, 4H), 7.91 (d, 1H), 8.05 (d, 1H). |
| 51 | (structure) | chromatography (CH$_2$Cl$_2$, followed by CH$_2$Cl$_2$:ethanol = 95:5) | yellow resin, 0.86 (d, 6H), 1.73–1.85 (m, 1H), 2.37 (s, 3H), 2.46 (d, 2H), 3.76 (s, 3H), 7.11–7.40 (m, 5H), 7.76 (d, 2H), 7.84 (d, 4H), 9.86 (s, 1H). |
| 52 | (structure) | chromatography (CH$_2$Cl$_2$:acetone = 3:1) | white solid, 102–106° C., 5.10 (s, 2H), 7.17–7.25 (m, 3H), 7.36 (d, 2H), 7.58–7.75 (m, 15H). |

TABLE 1-continued

| Ex. | Structure | Purification | State/mp(° C.)/ $^1$H-NMR [δ(ppm)] |
|---|---|---|---|
| 53 | (triphenylsulfonium cation with 4-methyl-2-isopropylcyclohexyl sulfonate anion) | chromatography (CH$_2$Cl$_2$:acetone = 3:1) | white solid, 116–124° C., 0.77–0.87 (m, 10H), 0.95–1.10 (m, 2H), 1.20–1.28 (m, 1H), 1.35–1.50 (m, 1H), 1.56–1.63 (m, 2H), 2.33–2.42 (m, 1H), 2.53–2.60 (m, 1H), 4.18–4.27 (m, 1H), 7.64–7.84 (m, 15H). |

EXAMPLE 54

A chemically amplified positive resist formulation is prepared by mixing the following components:

100.0 parts of a resin binder (a copolymer of 22 mol % styrene, 69 mol % p-hydroxystyrene and 9 mol % t-butyl acrylate, having a Mw of 9850; $^{RTM}$Maruzen MARUKA LYNCUR PHS/STY/TBA, provided by Maruzen Oil Company, Japan)

0.5 parts of a leveling agent (FC-430, provided by 3M)

475.0 parts of propylene glycol methyl ether acetate (PGMEA) (provided by Tokyo Kasei, Japan)

4.0 parts of the photoacid generator to be tested.

The resist formulation is spin coated onto a hexamethyl dimethylsilane-treated silicone wafer at around 1700 rpm for 45 seconds and softbaked for 90 seconds at 140° C. on a hotplate to obtain a film thickness of 800 nm. The resist film is exposed to 254 nm wavelength deep UV radiation through a narrow band interference filter and a multidensity quartz mask using an Ushio's high pressure mercury lamp, UXM-501 MD, and a mask aligner Canon PLA-521. After a post exposure bake for 90 seconds at 140° C. on a hotplate the film is developed. The exposure intensity is measured with a Unimeter UIT-150 from Ushio. The "Dose to Clear" (E$_0$), which is the dose just sufficient to completely remove the resist film with 60 seconds immersion development in 1.79% aqueous tetramethyl ammonium hydroxide developer, is determined from the measured contrast curve (characteristic curve) as described in R. Dammel, Diazonaphthoquinone-based Resists, SPIE Tutorial Text Series Vol. TT 11, Optical Engineering Press, p. 10–11 (1993). The smaller the required dose, the more sensitive is the resist formation. The results are collected in table 2 and demonstrate that the compositions according to the invention are suitable for the preparation of positive photoresists.

TABLE 2

| Compound of example | Dose to Clear (E$_0$) [mJ/cm$^2$] |
|---|---|
| 1 | 1.05 |
| 2 | 0.68 |
| 3 | 0.91 |
| 4 | 1.43 |
| 5 | 0.62 |
| 6 | 1.06 |
| 7 | 1.24 |
| 8 | 1.23 |
| 9 | 1.18 |
| 10 | 1.55 |
| 11 | 2.14 |
| 12 | 0.69 |
| 13 | 1.05 |
| 14 | 0.98 |
| 15 | 1.05 |
| 16 | 0.81 |
| 17 | 0.58 |
| 18 | 0.82 |
| 19 | 0.82 |
| 20 | 0.89 |
| 21 | 0.73 |
| 22 | 0.74 |
| 23 | 0.74 |
| 24 | 1.02 |
| 25 | 1.57 |
| 26 | 1.09 |
| 27 | 1.08 |
| 28 | 1.06 |
| 29 | 0.72 |
| 30 | 1.14 |
| 31 | 0.86 |
| 32 | 0.94 |
| 33 | 1.12 |
| 34 | 1.85 |
| 35 | 0.98 |
| 36 | 0.82 |
| 37 | 1.20 |
| 46 | 0.89 |
| 47 | 0.99 |
| 48 | 0.94 |
| 49 | 1.37 |
| 50 | 1.59 |
| 51 | 1.62 |

EXAMPLE 55

A chemically amplified positive resist formulation is prepared by mixing the following components:

- 100.0 parts of a resin binder (a copolymer of 39 mol % p-(t-butoxycarbonyloxy)styrene, and 61 mol % p-hydroxyrene, derived from VP-8000 having a Mw of 11900, provided by Nippon Soda Co., Ltd, Japan)
- 0.5 parts of a leveling agent (FC-430, provided by 3M)
- 475.0 parts of propylene glycol methyl ether acetate (PGMEA) (provided by Tokyo Kasei, Japan)
- 4.0 parts of the photoacid generator to be tested The resist formulation is spin coated onto a hexamethyl dimethylsilane-treated silicone wafer at around 1800 rpm for 45 seconds and softbaked for 60 seconds at 85° C. on a hotplate to obtain a film thickness of 800 nm. The resist film is then exposed to 254 nm wavelength deep UV radiation through a narrow band interference filter and a multidensity quartz mask using and Ushio's high pressure mercury lamp, UXM-501MD, and a mask aligner Canon PLA-521, After a post exposure bake for 60 seconds at 85° C. on a hotplate the resist is developed. The exposure intensity is measured with Unimeter UIT-150 from Ushio. The "Dose to Clear" ($E_0$), which is the dose just sufficient to completely remove the resist film with 60 seconds immersion development in 2.38% aqueous tetramethyl ammonium hydroxide developer, is determined from the measured contrast curve (characteristic curve). The smaller the required dose the more sensitive is the resist formulation. The results are collected in table 3 and demonstrate that the compositions are suitable for the preparation of positive photoresists.

TABLE 3

| Compound of example | Dose to Clear ($E_0$) [mJ/cm²] |
|---|---|
| 3 | 21 |
| 4 | 18 |

What is claimed is:

1. A chemically amplified photoresist composition comprising, (a) a compound which cures upon the action of an acid or a compound whose solubility is increased upon the action of an acid; and (b) as photosensitive acid donor, at least one compound of the formula Ia, Ib, Ic, IIa, IIb or IIc

  (Ia)

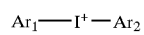

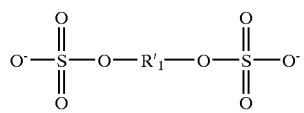  (Ib)

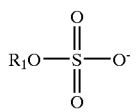

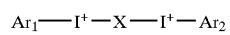  (Ic)

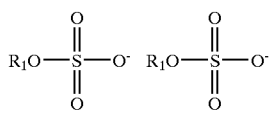

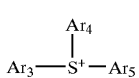  (IIa)

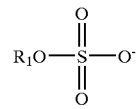

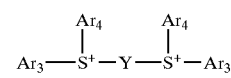  (IIb)

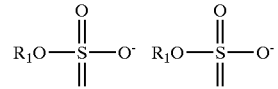

  (IIc)

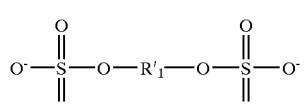

wherein $R_1$ is $C_2$–$C_{12}$alkyl which is interrupted by one or more —O— or —(CO)—, or is $C_3$–$C_{30}$cycloalkyl, or is $C_3$–$C_{30}$cycloalkyl which is interrupted by one or more —O—, —S—, —NR$_6$—, —(CO)—, —O(CO)— or —NR$_6$(CO)—, or is $C_2$–$C_{12}$alkenyl, or is $C_4$–$C_8$cycloalkenyl, or is $C_6$–$C_{12}$bicycloalkenyl, all of which are unsubstituted or substituted by one or more $C_1$–$C_5$alkyl, $C_1$–$C_5$haloalkyl; $C_3$–$C_{30}$cycloalkyl which optionally is interrupted by one or more —O—, —S—, —NR$_6$—, —(CO)—, —O(CO)— or —NR$_6$(CO)—; or are substituted by halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or $R_1$ is benzyl;

or $R_1$ is phenyl, or is naphthyl, or is anthracyl or is phenanthryl, or is a heteroaryl radical, all of which are unsubstituted or substituted by one or more $C_1$–$C_5$alkyl; $C_2$–$C_{12}$alkyl which is interrupted by one or more —O—; or are substituted by $C_1$–$C_5$haloalkyl, $C_3$–$C_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$; optionally the substituents —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$ form 5- or 6-membered rings, via the radicals R$_2$, R$_3$, R$_4$ R$_5$ and/or R$_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

wherein all radicals $R_1$ optionally additionally are substituted by a group having a —O—C-bond or a —O—Si-bond which cleaves upon the action of an acid;

$R'_1$ is $C_1$–$C_{12}$alkylene; or is $C_2$–$C_{12}$alkylene which is interrupted by one or more $C_3$–$C_{30}$-cycloalkylene, —O—, —S—, —NR$_6$—, —(CO)—, —O(CO)—, —S(CO)—, —NR$_6$(CO)—, —SO—, —SO$_2$—, or —OSO$_2$—; optionally the radicals $C_1$–$C_{12}$alkylene and $C_2$–$C_{12}$alkylene are substituted by one or more $C_1$–$C_5$haloalkyl, $C_3$–$C_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or $R'_1$ is $C_3$–$C_{30}$cycloalkylene, optionally interrupted by one or more —O—, —S—, —NR$_6$—, —(CO)—, —O(CO)—, or —NR$_6$(CO)—, and which is unsubstituted or substituted by one or more $C_1$–$C_5$alkyl, $C_1$–$C_5$haloalkyl, $C_3$–$C_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_4$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or $R'_1$ is phenylene, naphthylene,

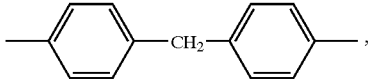

diphenylene, oxydiphenylene or

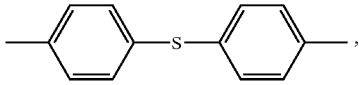

wherein these radicals are unsubstituted or substituted by one or more $C_1$–$C_5$alkyl, $C_3$–$C_5$haloalkyl, $C_3$–$C_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_5$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or $R'_1$ is

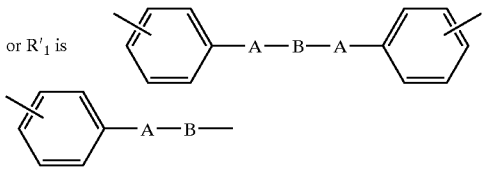

or

A is a direct bond, —O—, —S—, —NR$_6$—, —O(CO)—, —S(CO)—, —NR$_6$(CO)—, —SO—, —SO$_2$— or —OSO$_2$—, B is a direct bond, $C_1$–$C_{12}$alkylene or $C_2$–$C_{12}$alkylene which is interrupted by one or more —O—, —S—, —NR$_6$—, —O(CO)—, —S(CO)—, —NR$_6$(CO)—, —SO—, —SO$_2$— or —OSO$_2$—, and optionally the radicals $C_1$–$C_{12}$alkylene and $C_2$–$C_{12}$alkylene are substituted by one or more $C_1$–$C_5$alkyl, $C_1$–$C_5$haloalkyl, $C_3$–$C_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

$R_2$ is phenyl, or is $C_3$–$C_{30}$cycloalkyl, or is $C_1$–$C_5$alkyl; or is $C_2$–$C_5$alkyl which is interrupted by one or more —O—, or is $C_3$–$C_{30}$cycloalkyl which is interrupted by one or more —O—, —S—, —NR$_6$—, —O(CO)—, or —NR$_6$(CO)—;

all of which are unsubstituted or substituted by phenyl, OH, $C_1$–$C_5$alkyl, $C_1$–$C_5$haloalkyl, $C_3$–$C_{30}$cycloalkyl, halogen, —NO$_2$, —CN, $C_1$–$C_4$alkoxy, phenoxy, phenoxycarbonyl, phenylthio, phenylthiocarbonyl, —NR$_4$R$_5$, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;

or $R_2$ is hydrogen;

$R_3$ is phenyl, or is $C_3$–$C_{30}$cycloalkyl, or is $C_1$–$C_5$alkyl; or is $C_2$–$C_5$alkyl which is interrupted by one or more —O—; or is $C_3$–$C_{30}$cycloalkyl which is interrupted by one or more —O—, —S—, —NR$_6$—, —O(CO)—, or —NR$_6$(CO)—; or is $C_2$–$C_{18}$alkanoyl, or is benzoyl, or is $C_1$–$C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, —NO$_2$, —CN, $C_1$–$C_4$alkoxy, phenoxy, phenoxycarbonyl, phenylthio, phenylthiocarbonyl, —NR$_4$R$_5$, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;

or $R_3$ is hydrogen, phenylsulfonyl, (4-methylphenyl)sulfonyl, naphthylsulfonyl, anthracylsulfonyl or phenanthrylsulfonyl;

$R_4$, $R_5$ and $R_6$ independently of each other are phenyl, or are $C_3$–$C_{30}$cycloalkyl, or are $C_1$–$C_5$alkyl; or are $C_2$–$C_5$alkyl which is interrupted by one or more —O—; or are $C_3$–$C_{30}$cycloalkyl which is interrupted by one or more —O—, —S—, —NR$_6$—, —O(CO)—, or —NR$_6$(CO)—; or are $C_2$–$C_{18}$alkanoyl, or are benzoyl, or are $C_2$–$C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, —NO$_2$, —CN, $C_1$–$C_4$alkoxy, phenoxy, phenoxycarbonyl, phenylthio, phenylthiocarbonyl, $C_1$–$C_4$alkylthio, $C_2$–$C_4$alkoxycarbonyl, $C_2$–$C_4$haloalkanoyl, halobenzoyl, $C_1$–$C_4$alkylsulfonyl, phenylsulfonyl, (4-methylphenyl)sulfonyl, $C_1$–$C_4$alkylsulfonyloxy, phenylsulfonyloxy, (4-methylphenyl)sulfonyloxy and/or by $C_1$–$C_4$alkanoyl;

or $R_4$, $R_5$ and $R_6$ independently of each other are hydrogen, phenylsulfonyl, (4-methylphenyl)sulfonyl, naphthylsulfonyl, anthracylsulfonyl or phenanthrylsulfonyl;

or $R_4$ and $R_5$, together with the nitrogen atom to which they are attached, form a 5-, 6- or 7-membered ring which optionally is interrupted by —O— or by —NR$_6$—;

$Ar_1$ and $Ar_2$ independently of each other are phenyl, or are naphthyl, or are anthracyl, or are phenanthryl, or are heteroaryl, all of which are unsubstituted or are substituted by one or more $C_1$–$C_{12}$alkyl, $C_1$–$C_5$haloalkyl, $C_3$–$C_{30}$cycloalkyl; $C_3$–$C_{30}$cycloalkyl which is interrupted by one or more —O—, —S—, —$NR_6$—, —O(CO)—, or —$NR_6$(CO)—; or are substituted by halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$, optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$ $R_5$ and/or $R_5$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

or $Ar_1$ and $Ar_2$, if appropriate together with $C_1$–$C_2$alkylene, —O—, —S—, —$NR_6$—, or —(CO)—, form a fused ring;

wherein all radicals $Ar_1$ and $Ar_2$ optionally additionally are substituted by a group having a —O—C-bond or a —O—Si-bond which cleaves upon the action of an acid;

$Ar_3$, $Ar_4$ and $Ar_5$ have one of the meanings given for $Ar_1$ and $Ar_2$ or are or $Ar_3$, $Ar_4$ and $Ar_5$ independently of each other are $C_1$–$C_{12}$alkyl; or are $C_2$–$C_{12}$alkyl which is interrupted by one or more —O—; or are $C_1$–$C_5$haloalkyl; or are $C_3$–$C_{30}$cycloalkyl which optionally is interrupted by one or more —O—, —S—, —$NR_6$—, —O(CO)—, -or —$NR_6$(CO)—;

all of which are unsubstituted or substituted by one or more $C_1$–$C_{12}$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_6$, —O(CO)$R_2$, —O(CO)$OR_3$, —O(CO)$NR_4R_5$, —$NR_6$(CO)$R_2$, —$NR_6$(CO)$OR_3$, —$OR_5$, —$NR_4R_5$, —$SR_6$, —$SOR_2$, —$SO_2R_2$ and/or —$OSO_2R_2$;

or $Ar_3$ and $Ar_4$, if appropriate together with $C_1$–$C_2$alkylene, —O—, —S—, —$NR_6$—, —(CO)—, form a fused ring;

or $Ar_3$ and $Ar_4$, if appropriate together with $C_1$–$C_2$alkylene, —O—, —S—, —$NR_6$—, —(CO)—, form a 5-, 6-, or 7-membered ring;

wherein all radicals $Ar_3$, $Ar_4$ and $Ar_5$ optionally additionally are substituted by a group having a —O—C-bond or a —O—Si-bond which cleaves upon the action of an acid;

$Ar_6$ is phenyl, or is naphthyl, or is anthracyl, or is phenanthryl or is heteroaryl, all of which are unsubstituted or substituted by one or more $C_1$–$C_5$ alkyl; $C_2$–$C_{12}$alkyl which is interrupted by one or more —O—; or by $C_1$–$C_5$haloalkyl, $C_3$–$C_{30}$cycloalkyl, halogen, —$NO_2$, —CN, phenyl, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$, optionally the substituents —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl, naphthyl, anthracyl, phenanthryl or heteroaryl ring or with one of the carbon atoms of the phenyl, naphthyl, anthracyl, phenanthryl or heteroaryl ring;

X is phenylene, or is naphthylene, or is

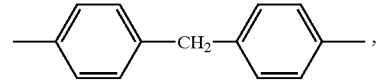

or is diphenylene, or is oxydiphenylene or is

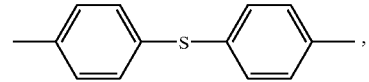

all of which are unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or X is —⟨phenyl⟩—A—B—A—⟨phenyl⟩—; and

Y has one of the meanings given for X, or is $C_1$–$C_{12}$alkylene; or $C_2$–$C_{12}$alkylene which is interrupted by one or more $C_3$–$C_{30}$cycloalkylene, —O—, —S—, —$NR_6$—, —(CO)—, —O(CO)—, —S(CO)—, —$NR_6$(CO)—, —SO—, —$SO_2$—, or —$OSO_2$—; wherein the $C_1$–$C_{12}$alkylene and $C_2$–$C_{12}$alkylene are unsubstituted or substituted by one or more $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$;

or Y is $C_3$–$C_{30}$cycloalkylene which optionally is interrupted by one or more —O—, —S—, —$NR_6$—, —(CO)—, —O(CO)—, or —$NR_6$(CO)—, and which is unsubstituted or substituted by one or more $C_1$–$C_5$alkyl, $C_1$–$C_5$haloalkyl, $C_3$–$C_{30}$cycloalkyl, halogen, —$NO_2$, —CN, —$Ar_6$, —(CO)$R_2$, —(CO)$OR_3$, —(CO)$NR_4R_5$, —O(CO)$R_2$, —O(CO)$OR_3$, —O(CO)$NR_4R_5$, —$NR_6$(CO)$R_2$, —$NR_6$(CO)$OR_3$, —$OR_3$, —$NR_4R_5$, —$SR_6$, —$SOR_2$, —$SO_2R_2$ and/or —$OSO_2R_2$.

2. A chemically amplified photoresist composition according to claim 1, comprising compounds of the formula Ia, Ib, Ic, IIa, IIb and/or IIc, wherein $R_1$ is benzyl;

or $R_1$ is phenyl, which is unsubstituted or substituted by one or more $C_1$–$C_5$ alkyl, $C_1$–$C_5$haloalkyl, halogen, —$NO_2$, —CN, —$Ar_6$,—(CO)$R_2$, —O(CO)$R_2$, —$NR_6$(CO)$R_2$, —$OR_3$, —$NR_4R_5$, —$SR_6$, —$SO_2R_2$ and/or —$OSO_2R_2$; optionally the substituents, —(CO)$R_2$, —O(CO)$R_2$,—$NR_6$(CO)$R_2$, —$OR_3$,—$NR_4R_5$, —$SR_6$, —$SO_2R_2$ and/or —$OSO_2R_2$ form 5- or 6-membered rings, via the radicals $R_2$, $R_3$, $R_4$ $R_5$ and/or $R_6$, with further substituents on the phenyl ring or with one of the carbon atoms of the phenyl ring;

or $R_1$ is naphthyl, which is unsubstituted or substituted by one or more $C_1$–$C_6$alkyl, $C_1$–$C_5$haloalkyl, halogen, and/or —$OR_3$;

wherein all radicals $R_1$ optionally additionally are substituted by a group having a —O—C-bond or a —O—Si-bond which cleaves upon the action of an acid;

$R'_1$ is $C_1$–$C_{12}$alkylene or $C_2$–$C_{12}$alkylene which is interrupted by one or more $C_3$–$C_{30}$cycloalkylene, —O—, —O(CO)—, or —$NR_6$(CO)—;

or $R'_1$ is $C_3$–$C_{30}$cycloalkylene which optionally is interrupted by one or more —O—, —O(CO)— or —$NR_6$(CO)—;

or $R'_1$ is phenylene, naphthylene;

$R_2$ is phenyl, or is $C_3$–$C_{30}$cycloalkyl, or is $C_1$–$C_5$alkyl, all of which are unsubstituted or substituted by phenyl, OH, $C_1$–$C_5$alkyl, $C_1$–$C_5$haloalkyl, $C_3$–$C_{30}$cycloalkyl, halogen, $C_1$–$C_4$alkoxy and/or phenoxy;

$R_3$ is phenyl, or is $C_3$–$C_{30}$cycloalkyl, or is $C_1$–$C_5$alkyl; or is $C_2$–$C_6$alkyl which is interrupted by one or more —O—; or is $C_3$–$C_{30}$cycloalkyl which is interrupted by one or more —O—, —O(CO)—, or —$NR_6$(CO)—; or is $C_2$–$C_{18}$alkanoyl, or is benzoyl, or is $C_1$–$C_{18}$alkylsulfonyl;

all of which are unsubstituted or substituted by phenyl, OH, $C_1$–$C_5$alkyl, $C_1$–$C_5$haloalkyl, $C_3$–$C_{30}$cycloalkyl, halogen and/or $C_1$–$C_4$alkoxy;

or $R_3$ is hydrogen, phenylsulfonyl, (4-methylphenyl) sulfonyl or naphthylsulfonyl;

$R_4$, $R_5$ and $R_6$ independently of each other are phenyl, or are $C_3$–$C_{30}$cycloalkyl, or are $C_1$–$C_5$alkyl; or are $C_2$–$C_5$alkyl which is interrupted by one or more —O—; or are $C_3$–$C_{30}$cycloalkyl which is interrupted by one or more —O—, —O(CO)—, or —$NR_6$(CO)—; or are $C_2$–$C_{18}$alkanoyl, or are benzoyl, or are $C_1$–$C_{18}$alkylsulfonyl, all of which are unsubstituted or substituted by phenyl, OH, $C_1$–$C_5$alkyl, $C_1$–$C_5$haloalkyl, $C_3$–$C_{30}$cycloalkyl, halogen, and/or $C_1$–$C_4$alkoxy;

or $R_4$ and $R_5$ independently of each other are hydrogen, phenylsulfonyl, (4-methylphenyl)sulfonyl or naphthylsulfonyl;

or $R_4$ and $R_5$, together with the nitrogen atom to which they are attached, form a 5-, 6- or 7-membered ring which optionally is interrupted by —O— or by —$NR_6$—;

$Ar_1$, $Ar_2$, $Ar_3$, $Ar_4$ and $Ar_5$ independently of each other are phenyl, which is unsubstituted or substituted by one or more $C_1$–$C_{12}$alkyl, $C_1$–$C_5$haloalkyl, $C_3$–$C_{30}$cycloalkyl, halogen, —O(CO)$R_2$, —O(CO)O$R_3$, —O(CO)$NR_4R_5$, —O$R_3$, and/or —S$R_6$;

wherein all radicals $Ar_1$, $Ar_2$, $Ar_3$, $Ar_4$ and $Ar_5$ optionally additionally are substituted by a group having a —O—C-bond or a —O—Si-bond which cleaves upon the action of an acid;

$Ar_6$ is phenyl, which is unsubstituted or substituted by one or more $C_1$–$C_{12}$alkyl, $C_1$–$C_5$haloalkyl, $C_3$–$C_{30}$cycloalkyl, halogen, —O(CO)$R_2$, —O(CO) O$R_3$, —O(CO)$NR_4R_5$, —O$R_3$, and/or —S$R_6$; and X and Y independently of one another are phenylene,

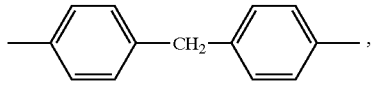

diphenylene, oxydiphenylene or

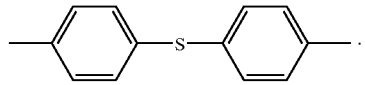

3. A chemically amplified photoresist composition according to claim 1, which is a positive resist.

4. A chemically amplified positive photoresist composition according to claim 3, comprising (a1) at least one polymer having an acid-labile group which decomposes in the presence of an acid to increase the solubility in aqueous alkaline developer solution; and/or (a2) at least one monomeric or oligomeric dissolution inhibitor having an acid-labile group which decomposes in the presence of an acid to increase the solubility in aqueous alkaline developer solution; and/or (a3) at least one alkali-soluble monomeric, oligomeric or polymeric compound; and (b) as photosensitive acid donor, at least one compound of formula Ia, Ib, Ic, IIa, IIb or IIc.

5. A chemically amplified photoresist composition according to claim 1, which is a negative resist.

6. A chemically amplified negative photoresist composition according to claim 5, comprising (a4) an alkali-soluble resin as binder;

(a5) a component which, when catalysed by an acid undergoes a crosslinking reaction with itself and/or with the binder; and (b) as photosensitive acid donor, at least one compound of formula Ia, Ib, Ic, IIa, IIb or IIc.

7. A chemically amplified photoresist composition according to claim 1, in addition to components (a) and (b), or components (a1), (a2), (a3) and (b), or components (a4), (a5) and (b) comprising further additives (c), further photosensitive acid donor compounds (b1), other photoinitiators (d), and/or sensitizers (e).

8. A process for the preparation of a photoresist by (1) applying to a substrate a composition as described above;

(2) post apply baking the composition at temperatures between 60° C. and 160° C.;

(3) image-wise irradiating with light of wavelengths between 150 nm and 1500 nm;

(4) optionally post exposure baking the composition at temperatures between 60° C. and 160° C.; and (5) developing with a solvent or with an aqueous alkaline developer.

9. A compound of the formula Ia, Ib, Ic, IIa, IIb or IIc

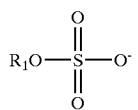 (Ia)

-continued

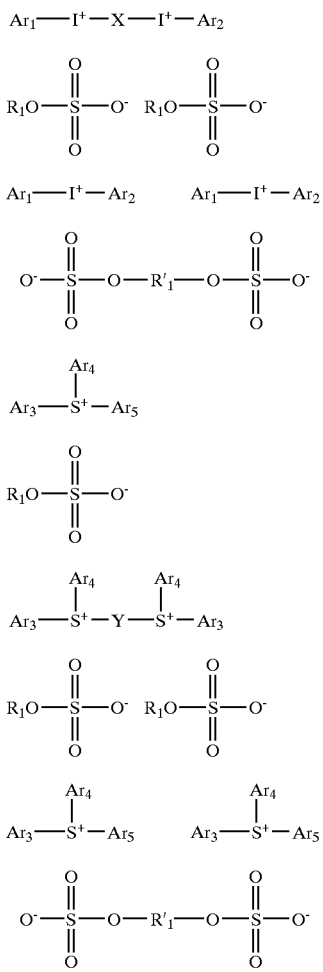

wherein
R$_1$ is C$_2$–C$_{12}$alkyl which is interrupted by one or more —O— or —(CO)—, or is C$_3$–C$_{30}$cycloalkyl, or is C$_3$–C$_{30}$cycloalkyl which is interrupted by one or more —O—, —S—, —NR$_6$—, —(CO)—, —O(CO)— or —NR$_6$(CO)—, or is C$_2$–C$_{12}$alkenyl, or is C$_4$–C$_8$cycloalkenyl, or is C$_6$–C$_{12}$bicycloalkenyl, all of which are unsubstituted or substituted by one or more C$_1$–C$_5$alkyl, C$_1$–C$_5$haloalkyl; C$_3$–C$_{30}$cycloalkyl which optionally is interrupted by one or more —O—, —S—, —NR$_6$—, —(CO)—, —O(CO)— or —NR$_6$(CO)—; or are substituted by halogen, —NO$_2$, —CN, —Ar$_6$, —(CO)R$_2$, —(CO)OR$_5$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R$_1$ is benzyl;

or R$_1$ is phenyl, or is naphthyl, or is anthracyl or is phenanthryl, or is a heteroaryl radical, all of which are unsubstituted or substituted by one or more C$_1$–C$_5$alkyl; C$_2$–C$_{12}$alkyl which is interrupted by one or more —O—; or are substituted by C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$; optionally the substituents —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_5$, —SOR$_2$, —SO$_2$R$_2$ and/or —OSO$_2$R$_2$ form 5- or 6-membered rings, via the radicals R$_2$, R$_3$, R$_4$ R$_5$ and/or R$_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

wherein all radicals R$_1$ optionally additionally are substituted by a group having a —O—C-bond or a —O—Si-bond which cleaves upon the action of an acid;

R'$_1$ is C$_1$–C$_{12}$alkylene; or is C$_2$–C$_{12}$alkylene which is interrupted by one or more C$_3$–C$_{30}$cycloalkylene, —O—, —S—, —NR$_6$—, —(CO)—, —O(CO)—, —S(CO)—, —NR$_6$(CO)—, —SO—, —SO$_2$—, or —OSO$_2$—; optionally the radicals C$_1$–C$_{12}$alkylene and C$_2$–C$_{12}$alkylene are substituted by one or more C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R'$_1$ is C$_1$–C$_{30}$cycloalkylene, optionally interrupted by one or more —O—, —S—, —NR$_6$—, —(CO)—, —O(CO)—, or —NR$_6$(CO)—, and which is unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R$_1$ is phenylene, naphthylene,

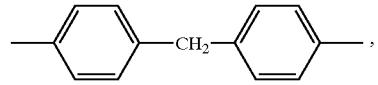

diphenylene, oxydiphenylene or

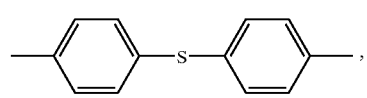

wherein these radicals are unsubstituted or substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or R'$_1$ is 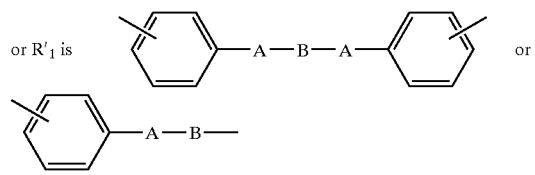 or

A is a direct bond, —O—, —S—, —NR$_6$—, —O(CO)—, —S(CO)—, —NR$_6$(CO)—, —SO—, —SO$_2$— or —OSO$_2$—;

B is a direct bond, C$_1$–C$_{12}$alkylene or C$_2$–C$_{12}$alkylene which is interrupted by one or more —O—, —S—, —NR$_6$—, —O(CO)—, —S(CO)—, —NR$_6$(CO)—, —SO—, —SO$_2$— or —OSO$_2$—, and optionally the radicals C$_1$–C$_{12}$alkylene and C$_2$–C$_{12}$alkylene are substituted by one or more C$_1$–C$_5$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

R$_2$ is phenyl, or is C$_3$–C$_{30}$cycloalkyl, or is C$_1$–C$_5$alkyl; or is C$_2$–C$_5$alkyl which is interrupted by one or more —O—, or is C$_3$–C$_{30}$cycloalkyl which is interrupted by one or more —O—, —S—, —NR$_6$—, —O(CO)—, or —NR$_6$(CO)—;

all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, —NR$_4$R$_5$, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and/or by C$_1$–C$_4$alkanoyl;

or R$_2$ is hydrogen;

R$_3$ is phenyl, or is C$_3$–C$_{30}$cycloalkyl, or is C$_1$–C$_5$alkyl; or is C$_2$–C$_5$alkyl which is interrupted by one or more —O—; or is C$_3$–C$_{30}$cycloalkyl which is interrupted by one or more —O—, —S—, —NR$_6$—, —O(CO)—, or —NR$_6$(CO)—; or is C$_2$–C$_{18}$alkanoyl, or is benzoyl, or is C$_1$–C$_{18}$alkylsulfonyl, all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, —NR$_4$R$_5$, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and/or by C$_1$–C$_4$alkanoyl;

or R$_3$ is hydrogen, phenylsulfonyl, (4-methylphenyl)sulfonyl, naphthylsulfonyl, anthracylsulfonyl or phenanthrylsulfonyl;

R$_4$, R$_5$ and R$_6$ independently of each other are phenyl, or are C$_3$–C$_{30}$cycloalkyl, or are C$_1$–C$_5$alkyl; or are C$_2$–C$_5$alkyl which is interrupted by one or more —O—; or are C$_3$–C$_{30}$cycloalkyl which is interrupted by one or more —O—, —S—, —NR$_6$—, —O(CO)—, or —NR$_6$(CO)—; or are C$_2$–C$_{18}$alkanoyl, or are benzoyl, or are C$_1$–C$_{18}$alkylsulfonyl, all of which are unsubstituted or substituted by phenyl, OH, C$_1$–C$_5$alkyl, C$_1$–C$_5$haloalkyl, C$_3$–C$_{30}$cycloalkyl, halogen, —NO$_2$, —CN, C$_1$–C$_4$alkoxy, phenoxy, phenoxycarbonyl, phenylthio, phenylthiocarbonyl, C$_1$–C$_4$alkylthio, C$_2$–C$_4$alkoxycarbonyl, C$_2$–C$_4$haloalkanoyl, halobenzoyl, C$_1$–C$_4$alkylsulfonyl, phenylsulfonyl, (4-methylphenyl)sulfonyl, C$_1$–C$_4$alkylsulfonyloxy, phenylsulfonyloxy, (4-methylphenyl)sulfonyloxy and/or by C$_1$–C$_4$alkanoyl;

or R$_4$, R$_5$ and R$_6$ independently of each other are hydrogen, phenylsulfonyl, (4-methylphenyl)sulfonyl, naphthylsulfonyl, anthracylsulfonyl or phenanthrylsulfonyl;

or R$_4$ and R$_5$, together with the nitrogen atom to which they are attached, form a 5-, 6- or 7-membered ring which optionally is interrupted by —O— or by —NR$_6$—;

Ar$_1$ and Ar$_2$ independently of each other are phenyl, or are naphthyl, or are anthracyl, or are phenanthryl, or are heteroaryl, all of which are unsubstituted or are substituted by one or more C$_1$–C$_{12}$alkyl, C$_1$–C$_5$haloalkyl, C$_3$–C$_{30}$cycloalkyl; C$_3$–C$_{30}$cycloalkyl which is interrupted by one or more —O—, —S—, —NR$_6$—, —O(CO)—, or —NR$_6$(CO)—; or are substituted by halogen, —NO$_2$, —CN, —Ar$_6$, —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$, optionally the substituents —(CO)R$_2$, —(CO)OR$_3$, —(CO)NR$_4$R$_5$, —O(CO)R$_2$, —O(CO)OR$_3$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$ form 5- or 6-membered rings, via the radicals R$_2$, R$_3$, R$_4$, R$_5$ and/or R$_6$, with further substituents on the phenyl, naphthyl, anthracyl, phenanthryl, or heteroaryl ring or with one of the carbon atoms of the phenyl, naphthyl, anthracyl, phenanthryl, or heteroaryl ring;

or Ar$_1$ and Ar$_2$, if appropriate together with C$_1$–C$_2$alkylene, —O—, —S—, —NR$_6$—, or —(CO)—, form a fused ring;

wherein all radicals Ar$_1$ and Ar$_2$ optionally additionally are substituted by a group having a —O—C-bond or a —O—Si-bond which cleaves upon the action of an acid;

Ar$_3$, Ar$_4$ and Ar$_5$ have one of the meanings given for Ar$_1$ and Ar$_2$ or are or Ar$_3$, Ar$_4$ and Ar$_5$ independently of each other are C$_1$–C$_{12}$alkyl; or are C$_2$–C$_{12}$alkyl which is interrupted by one or more —O—; or are C$_1$–C$_5$haloalkyl; or are C$_3$–C$_{30}$cycloalkyl which optionally is interrupted by one or more —O—, —S—, —NR$_6$—, —O(CO)—, -or —NR$_6$(CO)—;

all of which are unsubstituted or substituted by one or more C$_1$–C$_{12}$alkyl, C$_1$–C$_5$haloalkyl, C$_3$–C$_{30}$cycloalkyl, halogen, —NO$_2$, —CN, —Ar$_6$, —(CO)R$_2$, —(CO)OR$_3$, —(CO)NR$_4$R$_5$, —O(CO)R$_2$, —O(CO)OR$_9$, —O(CO)NR$_4$R$_5$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$;

or Ar$_3$ and Ar$_4$, if appropriate together with C$_1$–C$_2$alkylene, —O—, —S—, —NR$_6$—, —(CO)—, form a fused ring;

or Ar$_3$ and Ar$_4$, if appropriate together with C$_1$–C$_2$alkylene, —O—, —S—, —NR$_6$—, —(CO)—, form a 5-, 6-, or 7-membered ring;

wherein all radicals Ar$_3$, Ar$_4$ and Ar$_5$ optionally additionally are substituted by a group having a —O—C-bond or a —O—Si-bond which cleaves upon the action of an acid;

Ar$_6$ is phenyl, or is naphthyl, or is anthracyl, or is phenanthryl or is heteroaryl, all of which are unsubstituted or substituted by one or more C$_1$–C$_5$alkyl; C$_2$–C$_{12}$alkyl which is interrupted by one or more —O—; or by C$_1$–C$_5$haloalkyl, C$_3$–C$_{30}$cycloalkyl, halogen, —NO$_2$, —CN, phenyl, —(CO)R$_2$, —(CO)OR$_3$, —(CO)NR$_4$R$_5$, —O(CO)R$_2$, —O(CO)OR$_3$, —O(CO)NR$_4$R$_6$, —NR$_6$(CO)R$_2$, —NR$_6$(CO)OR$_3$, —OR$_3$, —NR$_4$R$_5$, —SR$_6$, —SOR$_2$, —SO$_2$R$_2$ and/or —OSO$_2$R$_2$, optionally the substituents —(CO)R$_2$, —(CO)OR$_3$, (CO)NR$_4$R$_5$, —O(CO)R$_2$, —O(CO)OR$_3$, —O(CO)NR$_4$R$_5$, —NR$_6$(CO)R$_2$, —NR₆(CO)OR₃, —OR₃, —NR₄R₅, —SR₆, —SOR₂, —SO₂R₂ and/or —OSO₂R₂ form 5- or 6-membered rings, via the radicals R₂, R₃, R₄ R₅ and/or R₆, with further substituents on the phenyl, naphthyl, anthracyl, phenanthryl or heteroaryl ring or with one of the carbon atoms of the phenyl, naphthyl, anthracyl, phenanthryl or heteroaryl ring;

X is phenylene, or is naphthylene, or is

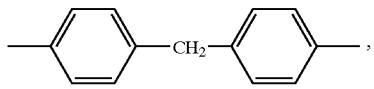

or is diphenylene, or is oxydiphenylene or is

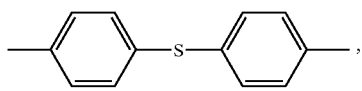

all of which are unsubstituted or substituted by one or more C₁–C₅alkyl, C₁–C₅haloalkyl, C₃–C₃₀cycloalkyl, halogen, —NO₂, —CN, —Ar₆, —(CO)R₂, —(CO)OR₃, —(CO)NR₄R₅, —O(CO)R₂, —O(CO)OR₃, —O(CO)NR₄R₅, —NR₆(CO)R₂, —NR₆(CO)OR₃, —OR₃, —NR₄R₅, —SR₆, —SOR₂, —SO₂R₂ and/or —OSO₂R₂;

or X is  ; and

Y has one of the menaings given for X, or is C₁–C₁₂alkylene; or C₂–C₁₂alkylene which is interrupted by one or more C₃–C₃₀cycloalkylene, —O—, —S—, —NR₆—, —(CO)—, —O(CO)—, —S(CO)—, —NR₆(CO)—, —SO—, —SO₂—, or —OSO₂—;

wherein the C₁–C₁₂alkylene and C₂–C₁₂alkylene are unsubstituted or substituted by one or more C₁–C₅haloalkyl, C₃–C₃₀cycloalkyl, halogen, —NO₂, —CN, —Ar₆, —(CO)R₂, —(CO)OR₃, —(CO)NR₄R₅, —O(CO)R₂, —O(CO)OR₃, —O(CO)NR₄R₅, —NR₆(CO)R₂, —NR₆(CO)OR₃, —OR₃, —NR₄R₅, —SR₆, —SOR₂, —SO₂R₂ and/or —OSO₂R₂;

or Y is C₃–C₃₀cycloalkylene which optionally is interrupted by one or more —O—, —S—, —NR₆—, —(CO)—, —O(CO)—, or —NR₆(CO)—, and which is unsubstituted or substituted by one or more C₁–C₅alkyl, C₁–C₅haloalkyl, C₃–C₃₀cycloalkyl, halogen, —NO₂, —CN, —Ar₆, —(CO)R₂, —(CO)OR₃, —(CO)NR₄R₅; —O(CO)R₂, —O(CO)OR₃, —O(CO)NR₄R₅, —NR₆(CO)R₂, —NR₆(CO)OR₃, —OR₃, —NR₄R₅, —SR₆, —SOR₂, —SO₂R₂ and/or —OSO₂R₂.

10. Compound of the formula Ia, Ic or IIa according to claim 9, wherein

R₁ is C₃–C₃₀cycloalkyl, which is unsubstituted or substituted by one or more C₁–C₅alkyl, —Ar₆, —(CO)R₂, or by C₃–C₃₀cycloalkyl, which optionally is interrupted by one or more —O—;

or R₁ is benzyl;

or R₁ is phenyl or naphthyl, unsubstituted or substituted by C₁–C₅alkyl, halogen, —(CO)R₂ or —OR₃;

R'₁ is C₃–C₃₀cycloalkylene or phenylene;

R₂ is phenyl, C₁–C₅alkyl or hydrogen;

R₃ is C₁–C₅alkyl;

Ar₁ and Ar₂ independently of each other are phenyl which is unsubstituted or substituted by C₁–C₁₂alkyl;

Ar₃, Ar₄ and Ar₅ have one of the meanings given for Ar₁ and Ar₂; and

Ar₆ is phenyl, naphthyl, anthracyl or heteroaryl, all of which are unsubstituted or substituted by NO₂, C₁–C₅alkyl, or C₂–C₁₂alkyl which is interrupted by one or more —O—.

11. A composition comprising (a) a compound which cures upon the action of an acid or a compound whose solubility is increased upon the action of an acid; and (b) as photosensitive acid donor, at least one compound of the formula Ia, Ib, Ic, IIa, IIb or IIc according to claim 9.

12. Process for crosslinking compounds that can be crosslinked under the action of an acid, which method comprises adding a compound of formula Ia, Ib, Ic, IIa, IIb and/or IIc according to claim 9 to the above-mentioned compounds and irradiating imagewise or over the whole area with light having a wavelength of 150–1500 nm.

13. Process according to claim 12 for the preparation of surface coatings, printing inks, printing plates, dental compositions, colour filters, resists or image-recording materials, or image-recording materials for recording holographic images.

* * * * *